(12) United States Patent
Benishti et al.

(10) Patent No.: US 9,814,433 B2
(45) Date of Patent: Nov. 14, 2017

(54) CREATING A VASCULAR TREE MODEL

(71) Applicant: CathWorks Ltd., RaAnana (IL)

(72) Inventors: Nessi Benishti, Kfar-Saba (IL); Ifat Lavi, Moshav Mishmeret (IL); Ran Kornowski, Ramat-HaSharon (IL); Idit Avrahami, Rosh HaAyin (IL); Guy Lavi, Moshav Mishmeret (IL)

(73) Assignee: CathWorks LTD. (IL)

( * ) Notice: Subject to any disclaimer, the term of this patent is extended or adjusted under 35 U.S.C. 154(b) by 0 days.

(21) Appl. No.: 14/761,079

(22) PCT Filed: Jan. 15, 2014

(86) PCT No.: PCT/IL2014/050044
§ 371 (c)(1),
(2) Date: Jul. 15, 2015

(87) PCT Pub. No.: WO2014/111930
PCT Pub. Date: Jul. 24, 2014

(65) Prior Publication Data
US 2015/0339847 A1    Nov. 26, 2015

Related U.S. Application Data

(63) Continuation-in-part of application No. PCT/IL2013/050869, filed on Oct. 24, 2013, and a
(Continued)

(51) Int. Cl.
G06T 17/00    (2006.01)
A61B 6/00    (2006.01)
(Continued)

(52) U.S. Cl.
CPC .............. A61B 6/466 (2013.01); A61B 5/026 (2013.01); A61B 5/02007 (2013.01);
(Continued)

(58) Field of Classification Search
CPC ..... A61B 6/504; A61B 5/02007; A61B 5/026; A61B 6/503; A61B 6/466; A61B 6/032;
(Continued)

(56) References Cited

U.S. PATENT DOCUMENTS 5,150,292 A * 9/1992 Hoffmann .............. A61B 6/481
250/303
6,047,080 A * 4/2000 Chen ..................... G06T 11/006
382/128
(Continued)

FOREIGN PATENT DOCUMENTS

EP          2633815        9/2013
WO    WO 2007/066249      6/2007
(Continued)

OTHER PUBLICATIONS

Sarwal et al. "3-D Reconstruction of Coronary Arteries." Proceedings of the 16th Annual International Conference of the IEEE Engineering in Medicine and Biology Society, Engineering Advances: New Opportunities for Biomedical Engineers, Nov. 3, 1994, pp. 504-505.*
(Continued)

*Primary Examiner* — Jon Chang
(74) *Attorney, Agent, or Firm* — K&L Gates LLP; Louis C. Cullman; Dennis A. Majewski

(57) ABSTRACT

A method for vascular modeling is disclosed. The method, in some embodiments, comprises receiving a plurality of 2-D angiographic images of a portion of a vasculature of a subject, and processing the images to automatically detect 2-D features, for example, paths along vascular extents, which are projected into 3-D to determine homologous features among blood vessels. In some embodiments, projection and/or image registration is iteratively altered to improve feature position matching. Based on 3-D vascular extents and their registration to 2-D images, additional
(Continued)

features such as vascular width are optionally determined and added to the model.

23 Claims, 25 Drawing Sheets

Related U.S. Application Data continuation-in-part of application No. 14/040,688, filed on Sep. 29, 2013.

(60) Provisional application No. 61/717,732, filed on Oct. 24, 2012, provisional application No. 61/752,526, filed on Jan. 15, 2013.

(51) Int. Cl.

| *G06F 19/00* | (2011.01) |
| *G06T 11/00* | (2006.01) |
| *G06T 7/00* | (2017.01) |
| *A61M 5/00* | (2006.01) |
| *A61B 5/02* | (2006.01) |
| *A61B 5/026* | (2006.01) |
| *G06T 7/55* | (2017.01) |
| *A61B 6/02* | (2006.01) |
| *A61B 6/03* | (2006.01) |
| *A61B 8/06* | (2006.01) |
| *A61B 5/021* | (2006.01) |
| *A61B 5/00* | (2006.01) |

(52) U.S. Cl.
CPC .............. *A61B 6/503* (2013.01); *A61B 6/504* (2013.01); *A61M 5/007* (2013.01); *G06F 19/321* (2013.01); *G06F 19/3431* (2013.01); *G06F 19/3437* (2013.01); *G06T 7/0012* (2013.01); *G06T 7/55* (2017.01); *G06T 11/008* (2013.01); *A61B 5/021* (2013.01); *A61B 5/0263* (2013.01); *A61B 5/7285* (2013.01); *A61B 6/02* (2013.01); *A61B 6/032* (2013.01); *A61B 6/037* (2013.01); *A61B 6/481* (2013.01); *A61B 6/507* (2013.01); *A61B 6/5217* (2013.01); *A61B 6/5258* (2013.01); *A61B 6/541* (2013.01); *A61B 8/06* (2013.01); *A61B 2576/023* (2013.01); *G06T 2200/04* (2013.01); *G06T 2207/10116* (2013.01); *G06T 2207/20044* (2013.01); *G06T 2207/20072* (2013.01); *G06T 2207/30101* (2013.01); *G06T 2207/30104* (2013.01); *G06T 2207/30172* (2013.01); *G06T 2210/41* (2013.01); *G06T 2211/404* (2013.01)

(58) Field of Classification Search
CPC ....... A61B 6/481; A61B 6/507; A61B 6/5217; A61B 6/541; A61B 8/06; A61B 5/021; A61B 2576/023; A61B 6/02; A61B 6/5258; A61B 5/7285; A61M 5/007; G06F 19/321; G06F 19/3431; G06F 19/3437; G06T 7/0012; G06T 11/008; G06T 7/0065; G06T 2207/20072; G06T 2200/04; G06T 2207/10072; G06T 2207/10116; G06T 2207/30101; G06T 2207/30104; G06T 2207/30172; G06T 2210/41; G06T 2207/20044; G06T 7/55; G06T 2211/404
USPC ........................................................ 382/131
See application file for complete search history.

(56) References Cited

U.S. PATENT DOCUMENTS

| 6,236,878 | B1 | 5/2001 | Taylor et al. |
| 7,657,299 | B2 | 2/2010 | Huizenga et al. |
| 7,738,626 | B2 | 6/2010 | Weese et al. |
| 8,090,164 | B2 | 1/2012 | Bullitt et al. |
| 8,311,748 | B2 | 11/2012 | Taylor et al. |
| 8,311,750 | B2 | 11/2012 | Taylor |
| 8,548,778 | B1 | 10/2013 | Hart et al. |
| 8,554,490 | B2 | 10/2013 | Tang et al. |
| 8,812,246 | B2 | 8/2014 | Taylor |
| 9,078,564 | B2 | 7/2015 | Taylor |
| 2004/0019264 | A1 | 1/2004 | Suurmond et al. |
| 2004/0066958 | A1* | 4/2004 | Chen ............... A61B 6/466 382/128 |
| 2005/0043614 | A1 | 2/2005 | Huizenga et al. |
| 2008/0020362 | A1 | 1/2008 | Cotin et al. |
| 2009/0312648 | A1 | 12/2009 | Zhang et al. |
| 2010/0160764 | A1 | 6/2010 | Steinberg et al. |
| 2010/0220917 | A1 | 9/2010 | Steinberg et al. |
| 2011/0096907 | A1 | 4/2011 | Mohamed |
| 2011/0142313 | A1 | 6/2011 | Pack et al. |
| 2012/0041318 | A1 | 2/2012 | Taylor |
| 2012/0041739 | A1 | 2/2012 | Taylor |
| 2012/0053918 | A1 | 3/2012 | Taylor |
| 2012/0053921 | A1 | 3/2012 | Taylor |
| 2012/0059246 | A1 | 3/2012 | Taylor |
| 2012/0072190 | A1 | 3/2012 | Sharma et al. |
| 2012/0150048 | A1 | 6/2012 | Kang et al. |
| 2012/0177275 | A1 | 7/2012 | Suri |
| 2012/0230565 | A1 | 9/2012 | Steinberg et al. |
| 2013/0060133 | A1 | 3/2013 | Kassab et al. |
| 2013/0094745 | A1* | 4/2013 | Sundar ............. G06T 3/0068 382/132 |
| 2013/0226003 | A1 | 8/2013 | Edic et al. |
| 2013/0324842 | A1 | 12/2013 | Mittal et al. |
| 2014/0094693 | A1 | 4/2014 | Cohen et al. |
| 2014/0200867 | A1 | 7/2014 | Lavi et al. |
| 2014/0303495 | A1 | 10/2014 | Fonte et al. |
| 2015/0265162 | A1 | 9/2015 | Lavi et al. |
| 2015/0335304 | A1 | 11/2015 | Lavi et al. |
| 2015/0342551 | A1 | 12/2015 | Lavi et al. |
| 2016/0007945 | A1 | 1/2016 | Taylor |
| 2016/0110866 | A1 | 4/2016 | Taylor |
| 2016/0110867 | A1 | 4/2016 | Taylor |
| 2016/0128661 | A1 | 5/2016 | Taylor |
| 2016/0247279 | A1 | 8/2016 | Lavi et al. |

FOREIGN PATENT DOCUMENTS

| WO | WO 2010/033971 | 3/2010 |
| WO | WO 2014/064702 | 5/2014 |
| WO | WO 2014/111927 | 7/2014 |
| WO | WO 2014/111929 | 7/2014 |
| WO | WO 2014/111930 | 7/2014 |
| WO | WO 2015/059706 | 4/2015 |

OTHER PUBLICATIONS

Yang et al. "Novel Approach for 3-D Reconstruction of Coronary Arteries From Two Uncalibrated Angiographic Images." IEEE Transactions on Image Processing, vol. 18, No. 7, Jul. 2009, pp. 1563-1572.*
Third-Party Submission filed on Feb. 2, 2016 From the US Patent and Trademark Office Re. U.S. Appl. No. 14/437,205.
Third-Party Submission filed on Jan. 28, 2016 From the US Patent and Trademark Office Re. U.S. Appl. No. 14/761,064.
Third-Party Submission filed on Jan. 28, 2016 From the US Patent and Trademark Office Re. U.S. Appl. No. 14/761,086.
USPTO Communication dated Feb. 8, 2016 Re Third-Party Submission From the US Patent and Trademark Office Re. U.S. Appl. No. 14/761,064.
USPTO Communication Dated Feb. 8, 2016 Re Third-Party Submission From the US Patent and Trademark Office Re. U.S. Appl. No. 14/761,086.

(56) References Cited

OTHER PUBLICATIONS

USPTO Communication Dated Feb. 19, 2016 Re Third-Party Submission From the US Patent and Trademark Office Re. U.S. Appl. No. 14/437,205.
Termeer et al. "Visualization of Myocardial Perfusion Derived From Coronary Anatomy", IEEE Transactions on Visualization and Computer Graphics, 14(6): 1595-1602, Nov./Dec. 2008.
Official Action Dated Aug. 15, 2016 From the US Patent and Trademark Office Re. U.S. Appl. No. 14/040,688.
Applicant-Initiated Interview Summary Dated Oct. 4, 2016 From the US Patent and Trademark Office Re. U.S. Appl. No. 14/040,688.
Third-Party Submission Under 37 CFR 1.290 filed on Jun. 14, 2016 From the US Patent and Trademark Office Re. U.S. Appl. No. 14/761,064.
Third-Party Submission Under 37 CFR 1.290 filed on Jun. 14, 2016 From the US Patent and Trademark Office Re. U.S. Appl. No. 14/761,086.
USPTO Communication Dated Jun. 22, 2016 Re Third-Party Submission From the US Patent and Trademark Office Re. U.S. Appl. No. 14/761,086.
USPTO Communication Dated Jun. 22, 2016 Re Third-Party Submission From the US Patent and Trademark Office Re. U.S. Appl. No. 14/7761,064.
Official Action Dated Dec. 24, 2015 From the US Patent and Trademark Office Re. U.S. Appl. No. 14/866,098.
Third-Party Submission filed on Feb. 1, 2016 From the US Patent and Trademark Office Re. U.S. Appl. No. 14/040,688.
USPTO Communication Dated Feb. 9, 2016 Re Third-Party Submission From the US Patent and Trademark Office Re. U.S. Appl. No. 14/040,688.
Third-Party Submission filed on Jun. 14, 2016 From the US Patent and Trademark Office Re. U.S. Appl. No. 14/437,205.
USPTO Communication Dated Jun. 22, 2016 Re Third-Party Submission From the US Patent and Trademark Office Re. U.S. Appl. No. 14/437,205.
International Preliminary Report on Patentability Dated May 6, 2016 From the International Bureau of WIPO Re. Application No. PCT/IL2014/050923.
Communication Relating to the Results of the Partial International Search Dated Feb. 6, 2015 From the International Searching Authority Re. Application No. PCT/IL2014/050923.
Communication Relating to the Results of the Partial International Search Dated Jan. 30, 2014 From the International Searching Authority Re. Application No. PCT/IL2013/050869.
International Preliminary Report on Patentability Dated May 7, 2015 From the International Bureau of WIPO Re. Application No. PCT/IL2013/050869.
International Preliminary Report on Patentability Dated Jul. 30, 2015 From the International Bureau of WIPO Re. Application No. PCT/L2014/050039.
International Preliminary Report on Patentability Dated Jul. 30, 2015 From the International Bureau of WIPO Re. Application No. PCT/L2014/050043.
International Preliminary Report on Patentability Dated Jul. 30, 2015 From the International Bureau of WIPO Re. Application No. PCT/L2014/050044.
International Search Report and the Written Opinion Dated Jul. 10, 2015 From the International Searching Authority Re. Application No. PCT/IL2014/050923.
International Search Report and the Written Opinion Dated May 16, 2014 From the International Searching Authority Re. Application No. PCT/IL2014/050043.
International Search Report and the Written Opinion Dated May 16, 2014 From the International Searching Authority Re. Application No. PCT/IL2014/050044.
International Search Report and the Written Opinion Dated May 23, 2014 From the International Searching Authority Re. Application No. PCT/IL2013/050869.
International Search Report and the Written Opinion Dated May 28, 2014 From the International Searching Authority Re. Application No. PCT/IL2014/050039.
Third-Party Submission Under 37 CFR 1.290 Dated Oct. 19, 2015 From the US Patent and Trademark Office Re. U.S. Appl. No. 14/040,688.
Andriotis et al. "A New Method of Three-Dimensional Coronary Artery Reconstruction From X-Ray Angiography: Validation Against a Virtual Phantom and Multislice Computed Tomography", Catheterization and Cardiovascular Interventions, 71(1): 28-43, Jan. 1, 2008.
Barratt et al. "Reconstruction and Qantification of the Carotid Artery Bifurcation From 3-D Ultrasound Images", IEEE Transactions on Medical Imaging, XP011112233, 23(5): 567-583, May 1, 2004.
Bullitt et al. "Determining Malignancy of Brain Tumors by Analysis of Vessel Shape", Medical Image Computing and Computer-Assisted Intervention, MICCAI 2004 Conference Proceedings, Lecture Notes in Computer Science, LNCS, 3217: 645-653, 2004.
Caiati et al. "Detection, Location, and Severity Assessment of Left Anterior Descending Coronary Artery Stenoses by Means of Contrast-Enhanced Transthoracic Harmonic Echo Doppler", European Heart Journal, 30: 1797-1806, 2009.
Caiati et al. "New Noninvasive Method for Coronary Flow Reserve Assessment: Contrast-Enhanced Transthoracic Second Harmonic Echo Doppler", Circulation, 99: 771-778, 1999.
Frangi et al. "Multiscale Vessel and Enhancement Filtering", Medical Image Computing and Computer-Assisted Intervention, MICCA'98, Lecture Notes in Computer Science, 1496: 130-137, 1998.
Fusejima "Noninvasive Measurement of Coronary Artery Blood Flow Using Combined Two-Dimensional and Doppler Echocardiography", Journal of the American College of Cardiology, JACC, 10(5): 1024-1031, Nov. 1987.
Hawkes et al. "Validation of Volume Blood Flow Measurements Using Three-Dimensional Distance-Concentration Functions Derived From Digital X-Ray Angiograms", Investigative Radiology, 29(4): 434-442, Apr. 1994.
Hoffmann et al. "Determination of Instantaneous and Average Blood Flow Rates From Digital Angiograms of Vessel Phantoms Using Distance-Density Curves", Investigative Radiology, 26(3): 207-212, Mar. 1991.
Holdsworth et al. "Quantitative Angiographic Blood-Flow Measurement Using Pulsed Intra-Arterial Injection", Medical Physics, 26(10): 2168-2175, Oct. 1999.
Janssen et al. "New Approaches for the Assessment of Vessle Sizes in Quantitative (Cardio-)Vascular X-Ray Analysis", International Journal of Cardiovascular Imaging, 26: 259-271, 2010.
Kappetein et al. "Current Percutaneous Coronary Intervention and Coronay Artery Bypass Grafting Practices for Three-Vessel and Left Main Coronary Artery Disease. Insights From the SYNTAX Run-In Phase", European Journal of Cardio-Thoracic Surgery, 29: 486-491, Aug. 18, 2010.
Kirkeeide "Coronary Obstructions, Morphology and Physiologic Significance", Quantitative Coronary Arteriography, Chap.11: 229-244, 1991.
Lethen et al. "Validation of Noninvasive Assessment of Coronary Flow Velocity Reserve in the Right Coronary Artery. A Comparison of Transthoracic Echocardiographic Results With Intracoronary Doppler Flow Wire Measurments", European Heart Journal, 24: 1567-1575, 2003.
Mcimoun et al. "Non-Invasive Assessment of Coronary Flow and Coronary Flow Reserve by Transthoracic Doppler Echocardiography: A Magic Tool for the Real World", European Journal of Echocardiography, 9: 449-457, 2008.
Molloi et al. "Quantification of Fractional Flow Reserve Using Angiographic Image Data", World Congress on Medical Physics and Biomedical Engineering, Munich, Germany, Sep. 7-12, 2009, IFMBE Proceedings, 25/2: 901-904, 2009.
Ng "Novel QCA Methodologies and Angiographic Scores", The International Journal of Cardiovascular Imaging, XP002718798, 27(2): 157-165, Feb. 20, 2011.

(56) References Cited

OTHER PUBLICATIONS

Pellot et al. "A 3D Reconstruction of Vascular Structures From Two X-Ray Angiograms Using an Adapted Simulated Annealing Algorithm", IEEE Transactions on Medical Imaging, 13(1): 48-60, Mar. 1994.
Pinho et al. "Assessment and Stenting of Tracheal Stenosis Using Deformable Shape Models", Medical Image Analysis, XP028364939, 15(2): 250-266, Dec. 2, 2010.
Seifalian et al. "A New Algorithm for Deriving Pulsatile Blood Flow Waveforms Tested Using Simulated Dynamic Angiographic Data", Neuroradiology, 31: 263-269, 1989.
Seifalian et al. "Blood Flow Measurments Using 3D Distance Concentration Functions Derived From Digital X-Ray Angiograms", Cardiovascular Imaging, Chap.33: 425-442, 1996.
Seifalian et al. "Validation of a Quantitative Radiographic Technique to Estimate Pulsatile Blood Flow Waveforms Using Digital Subtraction Angiographic Data", Journal of Biomedical Engineering, 13(3): 225-233, May 1991.
Shpilfoygel et al. "Comparison of Methods for Instantaneous Angiographic Blood Flow Measurement", Medical Physics, 26(6): 862-871, Jun. 1999.
Siogkas et al. "Quantification of the Effect of Percutaneous Coronary Angioplasty on a Stenosed Right Coronary Artery", 2010 10th IEEE International Conference on Infromation Technology and Applications in Biomedicine, ITAB 2010, Crofu, Greece, Nov. 3-5, 2010, p. 1-4, Nov. 2010. Abstract.
Slomka et al. "Fully Automated Wall Motion and Thickening Scoring System for Myocardial Perfusion SPECT: Method Development and Validation in Large Population", Journal of Nuclear Cardiology, XP002718797, 19(2): 291-302, Jan. 26, 2012.
Sprague et al. "Coronary X-Ray Angiographic Reconstruction and Image Orientation", Medical Physics, 33(3): 707-718, Mar. 2006.
Takarada et al. "An Angiographic Technique for Coronary Fractional Flow Reserve Measurement: In Vivo Validation", International Journal of Cardiovascular Imaging, International Journal of Cardiovascular Imaging, Published Online, p. 1-10, Aug. 31, 2012.
Tomasello et al. "Quantitative Coronary Angiography in the Interventional Cardiology", Advances in the Diagnosis of Coronary Atherosclerosis, Chap. 14: 255-272, Nov. 2011.
Tuinenburg et al. "Dedicated Bifurcation Analysis: Basic Principles", International Journal of Cardiovascular Imaging, 27: 167-174, 2011.
Voci et al. "Coronary Flow: A New Asset for the Echo Lab?", European Heart Journal, 25: 1867-1879, 2004.
Weickert "Anisotropic Diffusion in Image Processing", ECMI, Published by Teubner. Stuttgart, Germany, 184 P., 2008.
Weickert et al. "A Scheme for Coherence-Enhancing Diffusion Filtering With Optimized Rotation Invariance", Computer Vision, Graphics, and Pattern Recognition Group, CVGPR Group, Technical Report, Computer Science Series, 4/2000: 1-20, Feb. 2000.
Weickert et al. "A Scheme for Coherence-Enhancing Diffusion Filtering With Optimized Rotation Invariance", Journal of Visual Communication and Image Representation, 13(1-2): 103-118, Mar. 2002. & Computer Vision, Graphics, and Pattern Recognition Group, CVGPR, Computer Science Series, Technical Report 4/2000, Feb. 2000.
Wong et al. "Determination of Fractional Flow Reserve (FFR) Based on Scaling Laws: A Simulation Study", Physics in Medicine and Biology, 53: 3995-4011, 2008.
Wong et al. "Quantification of Fractional Flow Reserve Based on Angiographic Image Data", International Journal of Cardiovascular Imaging, XP035012993, 28(1): 13-22, Published Online Jan. 7, 2011. Abstract, Section 'Angiographic Based FFR'.
Youssef et al. "Role of Computed Tomography Coronary Angiography in the Detection of Vulnerable Plaque, Where Docs It Stand Among Others?", Angiology, 1(2): 1000111-1-1000111-8, 2013.
Notification of Office Action and Search Report Dated Mar. 7, 2017 From the State Intellectual Property Office of the People's Republic of China Re. Application No. 201480014756.X. (6 Pages).
Translation of Notification of Office Action Dated Mar. 7, 2017 From the State Intellectual Property Office of the People's Republic of China Re. Application No. 201480014756.X. (4 Pages).
Official Action Dated Dec. 23, 2016 From the US Patent and Trademark Office Re. U.S. Appl. No. 14/437,205. (54 pages).

\* cited by examiner

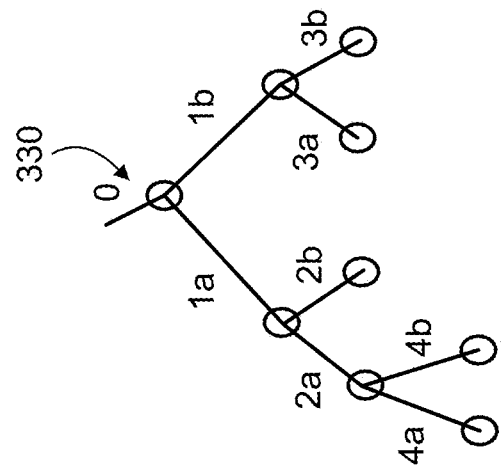
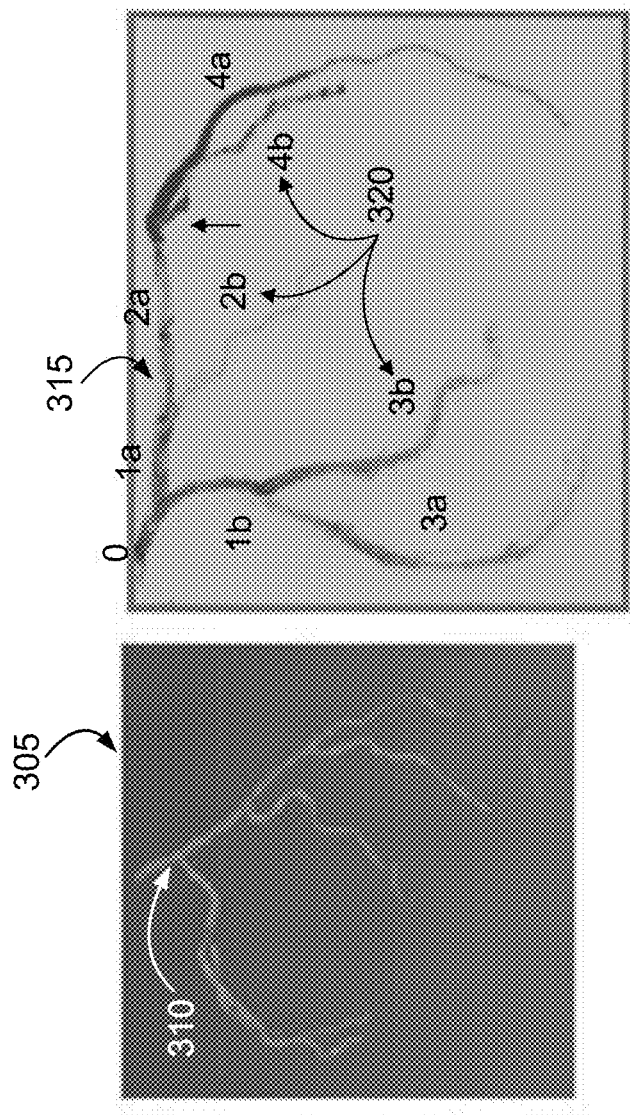
FIG. 3A  FIG. 3B  FIG. 3C

CREATING A VASCULAR TREE MODEL

RELATED APPLICATIONS

This application is a National Phase of PCT Patent Application No. PCT/IL2014/050044 having International filing date of Jan. 15, 2014, which is a Continuation-in-Part (CIP) of PCT Patent Application No. PCT/IL2013/050869 having International filing date of Oct. 24, 2013, which claims the benefit of priority under 35 USC §119(e) of U.S. Provisional Patent Application No. 61/717,732 filed on Oct. 24, 2012. PCT Patent Application No. PCT/IL2014/050044 is also a Continuation-in-Part (CIP) of U.S. patent application Ser. No. 14/040,688 filed on Sep. 29, 2013, which claims the benefit of priority under 35 USC §119(e) of U.S. Provisional Patent Application No. 61/752,526 filed on Jan. 15, 2013. The contents of the above applications are all incorporated by reference as if fully set forth herein in their entirety.

PCT Patent Application No. PCT/IL2014/050044 comprises one of three co-filed PCT Patent Applications, namely Nos. PCT/IL2014/050039, PCT/IL2014/050043 and PCT/IL2014/050044, all having International filing, dates of Jan 15, 2014.

FIELD AND BACKGROUND OF THE INVENTION

The present invention, in some embodiments thereof, relates to vascular modeling, and, more particularly, but not exclusively, to the use of a vascular model for producing indices relating to vascular function and diagnosis in real time—for example, during a catheterized imaging procedure.

Arterial stenosis is one of the most serious forms of arterial disease. In clinical practice, stenosis severity is estimated by using either simple geometrical parameter, such as determining the percent diameter of a stenosis, or by measuring hemodynamically based parameters, such as the pressure-based myocardial Fractional Flow Reserve (FFR). FFR is an invasive measurement of the functional significance of coronary stenoses. The FFR measurement technique involves insertion of a 0.014" guidewire equipped with a miniature pressure transducer located across the arterial stenosis. It represents the ratio between the maximal blood flow in the area of stenosis and the maximal blood flow in the same territory without stenosis. Earlier studies showed that FFR<0.75 is an accurate predictor of ischemia and deferral of percutaneous coronary intervention for lesions with FFR≥0.75 appeared to be safe.

An FFR cut-off value of 0.8 is typically used in clinical practice to guide revascularization, supported by long-term outcome data. Typically, an FFR value in a range of 0.75-0.8 is considered a 'grey zone' having uncertain clinical significance.

Modeling vascular flow and assessing vascular flow is described, for example, in U.S. Patent Application Publication No. 2012/0059246 of Taylor, to a "Method And System For Patient-Specific Modeling Of Blood Flow", which describes embodiments which include a system for determining cardiovascular information for a patient. The system may include at least one computer system configured to receive patient-specific data regarding a geometry of at least a portion of an anatomical structure of the patient. The portion of the anatomical structure may include at least a portion of the patient's aorta and at least a portion of a plurality of coronary arteries emanating from the portion of the aorta. The at least one computer system may also be configured to create a three-dimensional model representing the portion of the anatomical structure based on the patient-specific data, create a physics-based model relating to a blood flow characteristic within the portion of the anatomical structure, and determine a fractional flow reserve within the portion of the anatomical structure based on the three-dimensional model and the physics-based model. "Method And System For Patient-Specific Modeling Of Blood Flow", which describes embodiments which include a system for determining cardiovascular information for a patient. The system may include at least one computer system configured to receive patient-specific data regarding a geometry of at least a portion of an anatomical structure of the patient. The portion of the anatomical structure may include at least a portion of the patient's aorta and at least a portion of a plurality of coronary arteries emanating from the portion of the aorta. The at least one computer system may also be configured to create a three-dimensional model representing the portion of the anatomical structure based on the patient-specific data, create a physics-based model relating to a blood flow characteristic within the portion of the anatomical structure, and determine a fractional flow reserve within the portion of the anatomical structure based on the three-dimensional model and the physics-based model.

Additional background art includes:

U.S. Published Patent Application No. 2012/053918 of Taylor;

U.S. Published Patent Application No. 2012/0072190 of Sharma et al.;

U.S. Published Patent Application No. 2012/0053921 of Taylor;

U.S. Published Patent Application No. 2010/0220917 of Steinberg et al.;

U.S. Published Patent Application No. 2010/0160764 of Steinberg et al.;

U.S. Published Patent Application No. 2012/0072190 of Sharma et al.;

U.S. Published Patent Application No. 2012/0230565 of Steinberg et al.;

U.S. Published Patent Application No. 2012/0150048 of Kang et al.;

U.S. Published Patent Application No. 2013/0226003 of Edic et al.;

U.S. Published Patent Application No. 2013/0060133 of Kassab et al.;

U.S. Published Patent Application No. 2013/0324842 of Mittal et al.;

U.S. Published Patent Application No. 2012/0177275 of Suri and Jasjit;

U.S. Pat. No. 6,236,878 to Taylor et al.;

U.S. Pat. No. 8,311,750 to Taylor;

U.S. Pat. No. 7,657,299 to Hizenga et al.;

U.S. Pat. No. 8,090,164 to Bullitt et al.;

U.S. Pat. No. 8,554,490 to Tang et al.;

U.S. Pat. No. 7,738,626 to Weese et al.;

U.S. Pat. No. 8,548,778 to Hart et al.;

an article titled: "Determination of fractional flow reserve (FFR) based on scaling laws: a simulation study" by Jerry T. Wong and Sabee Molloi, published in Phys. Med. Biol. 53 (2008) 3995-4011;

an article titled: "A Scheme for Coherence-Enhancing Diffusion Filtering with Optimized Rotation Invariance", by Weickert, published in Journal of Visual Communication and Image Representation; Volume 13, Issues 1-2, March 2002, Pages 103-118 (2002);

a thesis in a book titled "Anisotropic Diffusion in Image Processing", by J. Weickert, published by B. G. Teubner (Stuttgart) in 1998;

an article titled: "Multiscale vessel enhancement filtering", by A. F Frangi, W. J. Niessen, K. L. Vincken, M. A. Viergever, published in Medical Image Computing and Computer-Assisted Intervention—MICCA '98;

an article titled: "Determination of fractional flow reserve (FFR) based on scaling laws: a simulation study", by Jerry T Wong and Sabee Molloi, published in Phys. Med. Biol. 53 (2008) 3995-4011;

an article titled: "Quantification of Fractional Flow Reserve Using Angiographic Image Data", by S. Molloi, J. T. Wong, D. A. Chalyan, and H. Le, published in O. Dössel and W. C. Schlegel (Eds.): WC 2009, IFMBE Proceedings 25/II, pp. 901-904, 2009;

an article titled: "Quantification of fractional flow reserve based on angiographic image data", by Jerry T. Wong, Huy Le, William M. Suh, David A. Chalyan, Toufan Mehraien, Morton J. Kern, Ghassan S. Kassab, and Sabee Molloi, published in Int J Cardiovasc Imaging (2012) 28:13-22;

an article titled: "An angiographic technique for coronary fractional flow reserve measurement: in vivo validation", by Shigeho Takarada, Zhang Zhang and Sabee Molloi, published online on 31 Aug. 2012 in Int J Cardiovasc Imaging;

an article titled: "A new algorithm for deriving pulsatile blood flow waveforms tested using stimulated dynamic angiographic data", by A. M. Seifalian, D. J. Hawkes, A. C. Colchester, and K. E. Hobbs, published in Neuroradiology, vol. 31, 263-269, 1989;

an article titled: "Validation of a quantitative radiographic technique to estimate pulsatile blood flow waveforms using digital subtraction angiographic data", by A. M. Seifalian, D. J. Hawkes, C. R. Hardingham, A. C. Colchester, and J. E Reidy, published in J. Biomed. Eng., vol. 13, no. 3, pp. 225-233, May 1991;

an article titled: "Validation of volume blood flow measurements using three dimensional distance-concentration functions derived from digital X-ray angiograms", by D. J. Hawkes, A. M. Seifalian, A. C. Colchester, N. Iqbal, C. R. Hardingham, C. E Bladin, and K. E. Hobbs, published in Invest. Radiol, vol. 29, no. 4, pp. 434-442, April 1994;

an article titled: "Blood flow measurements using 3D distance-concentration functions derived from digital X-ray angiograms", by A. M. Seifalian, D. J. Hawkes, C. Bladin, A. C. E Colchester, and K. E. F. Hobbs, published in Cardiovascular Imaging, J. H. C. Reiber and E. E. van der Wall, Eds. Norwell, Mass., The Netherlands: Kluwer Academic, 1996, pp. 425-442;

an article titled: "Determination of instantaneous and average blood flow rates from digital angiograms of vessel phantoms using distance-density curves", by K. R. Hoffmann, K. Doi, and L. E. Fencil, published in Invest. Radiol, vol. 26, no. 3, pp. 207212, March 1991;

an article titled: "Comparison of methods for instantaneous angiographic blood flow measurement", by S. D. Shpilfoygel, R. Jahan, R. A. Close, G. R. Duckwiler, and D. J. Valentino, published in Med. Phys., vol. 26, no. 6, pp. 862-871, June 1999;

an article titled: "Quantitative angiographic blood flow measurement using pulsed intra-arterial injection", by D. W. Holdsworth, M. Drangova, and A. Fenster, published in Med. Phys., vol. 26, no. 10, pp. 2168-2175, October 1999;

an article titled: "Dedicated bifurcation analysis: basic principles", by Joan C. Tuinenburg, Gerhard Koning, Andrei Rares, Johannes P. Janssen, Alexandra J. Lansky, Johan H. C. Reiber, published in Int J Cardiovasc Imaging (2011) 27:167-174;

an article titled: "Quantitative Coronary Angiography in the Interventional Cardiology", by Salvatore Davide Tomasello, Luca Costanzo and Alfredo Ruggero Galassi, published in Advances in the Diagnosis of Coronary Atherosclerosis;

an article titled: "New approaches for the assessment of vessel sizes in quantitative (cardio-)vascular X-ray analysis", by Johannes P. Janssen, Andrei Rares, Joan C. Tuinenburg, Gerhard Koning, Alexandra J. Lansky, Johan H. C. Reiber, published in Int J Cardiovasc Imaging (2010) 26:259-271;

an article titled: "Coronary obstructions, morphology and physiologic significance Quantitative Coronary Arteriography" by Kirkeeide R L. ed. Reiber J H C and Serruys P W, published by The Netherlands: Kluwer, 1991, pp 229-244;

an article titled: "Coronary x-ray angiographic reconstruction and image orientation", by Kevin Sprague, Maria Drangova, Glen Lehmann, Piotr Slomka, David Levin, Benjamin Chow and Robert deKemp, published in Med Phys, 2006 March; 33(3):707-718;

an article titled: "A New Method of Three-dimensional Coronary Artery Reconstruction From X-Ray Angiography: Validation Against a Virtual Phantom and Multislice Computed Tomography", by Adamantios Andriotis, Ali Zifan, Manolis Gavaises, Panos Liatsis, Ioannis Pantos, Andreas Theodorakakos, Efstathios P. Efstathopoulos, and Demosthenes Katritsis, published in Catheter Cardiovasc Interv, 2008, January 1; 71(1):28-43;

an article titled: "Noninvasive Measurement of Coronary Artery Blood Flow Using Combined Two-Dimensional and Doppler Echocardiography", by Kenji Fusejima, M D, published in JACC Vol. 10, No. 5, November 1987: 1024-31;

an article titled: "New Noninvasive Method for Coronary Flow Reserve Assessment: Contrast-Enhanced Transthoracic Second Harmonic Echo Doppler", by Carlo Caiati, Cristiana Montaldo, Norma Zedda, Alessandro Bina and Sabino Iliceto, published in Circulation, by the American Heart Association, 1999; 99:771-778;

an article titled: "Validation of noninvasive assessment of coronary flow velocity reserve in the right coronary artery—A comparison of transthoracic echocardiographic results with intracoronary Doppler flow wire measurements", by Harald Lethena, Hans P Triesa, Stefan Kerstinga and Heinz Lambertza, published in European Heart Journal (2003) 24, 1567-1575;

an article titled: "Coronary flow: a new asset for the echo lab?" by Paolo Vocia, Francesco Pizzutoa and Francesco Romeob, published in European Heart Journal (2004) 25, 1867-1879;

an abstract titled: "Quantification of the effect of Percutaneous Coronary Angioplasty on a stenosed Right Coronary Artery" by Siogkas et al., published in Information Technology and Applications in Biomedicine (ITAB), 2010 10th IEEE International Conference on a review paper titled: "Non-invasive assessment of coronary flow and coronary flow reserve by transthoracic Doppler echocardiography: a magic tool for the real world", by Patrick Meimoun and Christophe Tribouilloy, published in European Journal of Echocardiography (2008) 9, 449-457;

an article titled: "Detection, location, and severity assessment of left anterior descending coronary artery stenoses by means of contrast-enhanced transthoracic harmonic echo Doppler", by Carlo Caiati, Norma Zedda, Mauro Cadeddu, Lijun Chen, Cristiana Montaldo, Sabino Iliceto, Mario Erminio Lepera and Stefano Favale, published in European Heart Journal (2009) 30, 1797-1806; and an abstract titled "Determining malignancy of brain tumors by analysis of vessel shape" by Bullitt et al., published in Medical Image Computing and Computer-Assisted Intervention-MICCAI 2004.

The disclosures of all references mentioned above and throughout the present specification, as well as the disclosures of all references mentioned in those references, are hereby incorporated herein by reference.

SUMMARY OF THE INVENTION

According to an aspect of some embodiments of the present invention, there is provided a method for vascular assessment comprising: receiving a first vascular model of a cardiac vasculature; determining at least one characteristic based on the first vascular model representing flow through a stenotic segment of the vasculature; generating a second vascular model, comprising elements corresponding to the first vascular model, and at least one modification including a difference in at least one characteristic of flow; and calculating a flow index comparing the first and the second model.

According to some embodiments of the invention, the difference in at least one characteristic of flow comprises a difference between at least one characteristic of flow through a stenotic segment, and a characteristic of flow in a corresponding segment of the second model.

According to some embodiments of the invention, the vascular model is calculated based on a plurality of 2-D angiographic images.

According to some embodiments of the invention, the angiographic images are of sufficient resolution to allow determination of vascular width within 10%, to a vessel segment following an at least third branch point from a main human coronary artery.

According to some embodiments of the invention, the flow index comprises a prediction of flow increase achievable by an intervention to remove stenosis from the stenotic segment.

According to some embodiments of the invention, the comparative flow index is calculated based on a ratio of corresponding flow characteristics of the first and second vascular models.

According to some embodiments of the invention, the comparative flow index is calculated based on a ratio of corresponding flow characteristics of the stenotic and astenotic segments.

According to some embodiments of the invention, the method comprises reporting the comparative flow index as a single number per stenosis.

According to some embodiments of the invention, the at least one characteristic of flow comprises a flow rate.

According to some embodiments of the invention, the comparative flow index comprises an index representing a Fractional Flow Reserve index comprising a ratio of the maximal flow through a stenotic vessel, to the maximal flow through the stenotic vessel with the stenosis removed.

According to some embodiments of the invention, the comparative flow index is used in determining a recommendation for revascularization.

According to some embodiments of the invention, the comparative flow index comprises a value indicating a capacity for restoring flow by removal of a stenosis.

According to some embodiments of the invention, the first and the second vascular models comprise connected branches of vascular segment data, each branch being associated with a corresponding vascular resistance to flow.

According to some embodiments of the invention, the vascular model does not include a radially detailed 3-D description of the vascular wall.

According to some embodiments of the invention, the second vascular model is a normal model, comprising a relatively enlarged-diameter vessel replacing a stenotic vessel in the first vascular model.

According to some embodiments of the invention, the second vascular model is a normal model, comprising a normalized vessel obtained by normalizing a stenotic vessel based on properties of a neighboring astenotic vessel.

According to some embodiments of the invention, the at least one characteristic of flow is calculated based on properties of a plurality of vascular segments in flowing connection with the stenotic segment.

According to some embodiments of the invention, the characteristic of flow comprises resistance to fluid flow.

According to some embodiments of the invention, the method comprises: identifying in the first vascular model a stenosed vessel and a crown of vascular branches downstream of the stenosed vessel, and calculating the resistance to fluid flow in the crown; wherein the flow index is calculated based on a volume of the crown, and based on a contribution of the stenosed vessel to the resistance to fluid flow.

According to some embodiments of the invention, the first vascular model comprises a representation of vascular positions in a three-dimensional space.

According to some embodiments of the invention, each vascular model corresponds to a portion of the vasculature which is between two consecutive bifurcations of the vasculature.

According to some embodiments of the invention, each vascular model corresponds to a portion of the vasculature which includes a bifurcation of the vasculature.

According to some embodiments of the invention, each vascular model corresponds to a portion of the vasculature which extends at least one bifurcation of the vasculature beyond the stenotic segment.

According to some embodiments of the invention, each vascular model corresponds to a portion of the vasculature which extends at least three bifurcations of the vasculature beyond the stenotic segment.

According to some embodiments of the invention, the vascular model comprises paths along vascular segments, each of the paths being mapped along its extent to positions in the plurality of 2-D images.

According to some embodiments of the invention, the method comprises acquiring images of the cardiac vasculature, and constructing a first vascular model thereof.

According to some embodiments of the invention, each vascular model corresponds to a portion of the vasculature which extends distally as far as resolution of the images allows determination of vascular width within 10% of the correct value.

According to some embodiments of the invention, the vascular model is of a vasculature which has been artificially dilated during acquisition of images used to generate the model.

According to an aspect of some embodiments of the present invention, there is provided a computer software product, comprising a computer-readable medium in which program instructions are stored, which instructions, when read by a computer, cause the computer to receive a plurality of 2-D images of a subject's vasculature and execute the method for vascular assessment.

According to an aspect of some embodiments of the present invention, there is provided a system for vascular assessment comprising computer configured to:

receive the plurality of 2-D images; convert the plurality of 2-D to a first vascular model of the vasculature; determine at least one characteristic based on the first vascular model representing flow through a stenotic segment of the vasculature; generate a second vascular model, comprising elements corresponding to the first vascular model, and at least one modification including altering the at least one characteristic of flow through a stenotic segment to a characteristic of flow as if through a corresponding segment in which the effect of stenosis is reduced, and calculate a flow index comparing the first and the second model.

According to some embodiments of the invention, the computer is configured to calculate the flow index within 5 minutes of receiving the first vascular model.

According to some embodiments of the invention, the computer is configured to calculate the flow index within 5 minutes of the acquisition of the 2-D images.

According to some embodiments of the invention, the computer is located at a location remote from the imaging device.

According to an aspect of some embodiments of the present invention, there is provided a method for vascular assessment comprising: receiving a vascular model of a cardiac vasculature; determining at least a first flow characteristic based on the vascular model representing flow through a stenotic segment of the vasculature and the crown vessels to the stenotic segment; determining at least a second flow characteristic based on the vascular model representing flow through the crown vessels, without limitation of the flow by the stenotic segment; and calculating a flow index comparing the first and the second flow characteristics.

According to an aspect of some embodiments of the present invention, there is provided a method for construction of a vascular tree model comprising: receiving a plurality of 2-D angiographic images of blood vessel segments comprised in a portion of a vasculature of a subject; extracting automatically, from each of the plurality of 2-D angiographic images, a corresponding image feature set comprising 2-D feature positions of the blood vessel segments; adjusting automatically the 2-D feature positions to reduce relative position error in a common 3-D coordinate system to which each the image feature set is back-projectable; associating automatically the 2-D feature positions across the image feature sets such that image features projected from a common blood vessel segment region are associated; and determining automatically a representation of the image features based on inspection of 3-D projections determined from the associated 2-D feature positions, and selection of an optimal available 3-D projection therefrom.

According to some embodiments of the invention, the image feature set which is extracted comprises a centerline data set including 2-D centerline positions ordered along the blood vessel segments.

According to some embodiments of the invention, the determined representation is a 3-D spatial representation of blood vessel segment extent.

According to some embodiments of the invention, the determined representation is a graph representation of blood vessel segment extent.

According to some embodiments of the invention, information required for the associating automatically of 2-D image positions is entirely provided before review of the images by a human operator.

According to some embodiments of the invention, the adjusting, associating and determining are performed with elements of the centerline data set.

According to some embodiments of the invention, the adjusting comprises registration of the 2-D images in 3-D space according to parameters which bring the 2-D centerline positions into closer correspondence among their 3-D back-projections.

According to some embodiments of the invention, the image feature set which is extracted comprises a landmark data set including at least one of a group consisting of an origin of the tree model, a location of locally reduced radius in a stenosed blood vessel segment, and a bifurcation among blood vessel segments.

According to some embodiments of the invention, the image feature set which is extracted comprises a landmark data set including pixel intensity configurations which are below a predetermined threshold of self-similarity over translation.

According to some embodiments of the invention, the adjusting is performed on elements of the landmark data set; and the associating and determining are performed among elements of the centerline data set.

According to some embodiments of the invention, the adjusting comprises registration of the 2-D images in 3-D space according to parameters which bring features of the landmark data set into closer correspondence among their 3-D back-projections.

According to some embodiments of the invention, the registration of the 2-D images comprises registration of positions of elements of the centerline data set.

According to some embodiments of the invention, the method comprises estimating a metric of radial vascular width based on values of at least one of the plurality of 2-D angiographic images along lines perpendicular to the ordered 2-D centerline positions.

According to some embodiments of the invention, the estimating a metric of radial vascular width comprises finding connected routes running along either side of the 2-D centerline positions, and the connected routes comprise pixels imaging the boundary region of a vascular wall.

According to some embodiments of the invention, the boundary region of a vascular wall is determined by analysis of the intensity gradient along the perpendicular lines.

According to some embodiments of the invention, the metric of radial vascular width is calculated as a function of centerline position.

According to some embodiments of the invention, the determining comprises adjusting of the 2-D feature positions based on projection of the 3-D representation into the 2-D plane of at least one of the plurality of 2-D angiographic images.

According to some embodiments of the invention, the adjusting comprises: calculating a 3-D representation of feature positions from the 2-D feature positions of a first subset of the plurality of 2-D angiographic images; adjusting 2-D feature positions in a second subset of the plurality of 2-D angiographic images to more closely match features of the 3-D representation, as if the first 3-D representation were projected into the adjusted imaging planes of the second subset; and iterating over the calculating and the adjusting with changes to the first and second subsets, until a halt condition is met.

According to some embodiments of the invention, the halt condition is a lack of position adjusting to the 2-D feature positions above a distance threshold.

According to some embodiments of the invention, the method comprises defining a surface corresponding to a shape of the heart of the subject, and using the surface as a constraint for the associating of the feature positions.

According to some embodiments of the invention, the images are acquired upon injection of a contrast agent to the vasculature, and the method further comprises: determining temporal characteristics of the movement of the contrast agent through the vasculature; constraining the feature positions based on the temporal characteristics.

According to some embodiments of the invention, the portion of the vasculature comprises coronary arteries.

According to some embodiments of the invention, the capturing of the plurality of 2D angiographic images is effected by a plurality of imaging devices to capture the plurality of 2D angiographic images.

According to some embodiments of the invention, the capturing of the plurality of 2D angiographic images comprises synchronizing the plurality of imaging devices to capture the plurality of images substantially at a same phase during a heart beat cycle.

According to an aspect of some embodiments of the present invention, there is provided a computer software product, comprising a computer-readable medium in which program instructions are stored, which instructions, when read by a computer, cause the computer to receive a plurality of 2D angiographic images of a portion of a vasculature and execute the method for construction of a vascular tree model.

According to an aspect of some embodiments of the present invention, there is provided a system for vascular assessment comprising: a computer logically connected to an angiographic imaging device for capturing a plurality of 2-D images of a portion of vasculature of a subject, configured to: accept the plurality of 2-D angiographic images from the plurality of angiographic imaging devices; extract, from each of the plurality of 2-D angiographic images, an image feature data set comprising 2-D feature positions of the blood vessel segments; adjust the 2-D feature positions to minimize relative position error in a 3-D coordinate system common to the feature positions; find correspondences of the 2-D feature positions among the image feature data sets such that 2-D feature positions projected from a common blood vessel segment region to different images are associated; and determine a 3-D representation of the 2-D feature positions based on inspection of 3-D projections determined from the associated 2-D feature positions.

According to some embodiments of the invention, the image feature set which the system is configured to extract comprises a centerline data set including 2-D centerline positions ordered along the blood vessel segments.

According to some embodiments of the invention, the system is configured to use the positions of elements of the centerline data set as the 2-D feature positions.

According to some embodiments of the invention, the system is configured to adjust the 2-D feature positions based on registration of the 2-D images in 3-D space according to parameters which bring the 2-D centerline positions into closer correspondence among their 3-D back-projections.

According to some embodiments of the invention, the measurements of radial vascular width comprise distances between connected routes running along either side of the 2-D centerline positions, and the connected routes comprise pixels imaging the boundary region of a vascular wall.

According to some embodiments of the invention, the image transformation-based adjustment is iteratively performable for at least a second selection of images for the first and second sets of images.

According to some embodiments of the invention, the portion of the vasculature comprises a tree of coronary arteries to at least a third branch point from the main coronary artery.

According to an aspect of some embodiments of the present invention, there is provided a method of construction of a vascular tree model comprising: receiving 2-D images of a vascular tree, each associated with a corresponding image plane position; automatically identifying vascular features of the 2-D images; identifying homologous vascular features among the images by: geometrically projecting rays from the vascular features within the image plane positions, and passing through a common image target space, and associating features having intersecting rays as homologous.

According to some embodiments of the invention, intersection of rays comprises passing within a predefined distance from one another.

According to some embodiments of the invention, the image plane positions are iteratively updated to reduce error in ray intersections, and the identifying of homologous vascular features is repeated thereafter.

According to an aspect of some embodiments of the present invention, there is provided a method of construction of a vascular tree model comprising iteratively back-projecting rays from features in a plurality of 2-D images to a common 3-D space, determining errors in the intersections of rays from features common among the plurality of 2-D images, adjusting the 2-D images, and repeating the back-projecting, determining, and adjusting at least a first additional time.

According to an aspect of some embodiments of the present invention, there is provided a model of a portion of a vasculature, wherein elements of the model are associated with a plurality of location descriptions selected from among the group consisting of: the coordinate space of a plurality of 2-D angiographic images, the coordinate space of a common 3-D space, and a vascular graph space having 1-D extents branched from connected nodes.

According to an aspect of some embodiments of the present invention, there is provided a method for vascular assessment comprising: receiving a plurality of 2-D angiographic images of a portion of a vasculature of a subject; producing, within 20 minutes of the receiving, and by automatic processing of the images, a first 3-D vascular tree model over a portion of the vasculature comprising a stenotic heart artery; and determining automatically, based on the vascular tree model, an index quantifying a capacity for restoration of flow by opening of a stenosis.

According to some embodiments of the invention, the indication of a capacity for restoration of flow by opening of a stenosis comprises calculations based on change of a vascular width.

According to some embodiments of the invention, the automatic processing is performed within ten thousand trillion computational operations.

According to some embodiments of the invention, the automatic processing comprises formation of a model which does not include a radially detailed 3-D representation of a vascular wall.

According to some embodiments of the invention, the determining automatically and the automatic processing comprise formation of a model which does not include dynamic flow modeling.

According to some embodiments of the invention, the determining automatically comprises linear modeling of vascular flow characteristics.

According to some embodiments of the invention, the vascular tree model represents vascular width as a function of vascular extent.

According to some embodiments of the invention, vascular extent comprises distance along a vascular segment located at a nodal position on the vascular tree model.

According to some embodiments of the invention, the first 3-D vascular tree model comprises at least 3 branch nodes between vascular segments.

According to some embodiments of the invention, the first 3-D vascular tree model comprises vascular centerlines and vascular widths therealong.

According to some embodiments of the invention, the first 3-D vessel tree is produced within 5 minutes.

According to some embodiments of the invention, the method comprises calculating an FFR characteristic for at least one vascular segment of the vessel tree.

According to some embodiments of the invention, calculating the FFR characteristic comprises producing a second vascular tree model based on the first model, with a difference that vascular width is represented as larger in the second model, and comparing the first and second vascular tree models.

According to some embodiments of the invention, the comparing comprises obtaining a ratio of flow modeled in the first and second vascular tree models for the at least one vascular segment.

According to some embodiments of the invention, the FFR characteristic is calculated within 1 minute of producing the first 3-D vascular tree model.

According to some embodiments of the invention, the FFR characteristic is calculated within 10 seconds of producing the first and the second 3-D vascular tree models.

According to some embodiments of the invention, the FFR characteristic is a predictor of a pressure measurement-determined FFR index with a sensitivity of at least 95%.

According to some embodiments of the invention, the method comprises producing a projection of a portion of the first 3-D vessel tree into a 2-D coordinate reference frame shared by at least one of the plurality of 2-D angiographic images.

According to some embodiments of the invention, the at least one image is transformed from an original coordinate reference frame into a coordinate reference frame which is defined relative to the 3-D coordinate reference frame of the 3-D vessel tree.

According to some embodiments of the invention, the subject is vascularly catheterized during imaging that produces the received plurality of 2-D angiographic images, and remains catheterized during the receiving of images, and producing of a first 3-D vascular tree model.

According to some embodiments of the invention, the method comprises: imaging the subject to produce a second plurality of 2-D angiographic images after a first producing of a first vascular tree model; a second receiving of images, the images comprising the second plurality of images; and a second producing of a first 3-D vascular tree model; wherein the subject remains vascularly catheterized.

According to some embodiments of the invention, the producing occurs interactively with an ongoing catheterization procedure of the subject.

According to some embodiments of the invention, the calculating of an FFR characteristic occurs interactively with an ongoing catheterization procedure of the subject.

According to an aspect of some embodiments of the present invention, there is provided a system for vascular assessment comprising: a computer logically connected to an angiographic imaging device for capturing a plurality of 2-D images of a portion of vasculature of a subject, and configured to calculate a vascular tree model therefrom within 5 minutes; wherein an index of vascular function which indicates a capacity for restoration of flow by opening of a stenosis is determinable based on the vascular tree model within another minute.

According to some embodiments of the invention, determination based on the vascular tree model comprises generation of a second vascular tree model derived from the vascular tree model by widening a modeled vascular width in the region of a stenosis.

In some embodiments of the invention, one or more models of a patient's vascular system are produced.

In some embodiments, a first model is produced from actual data collected from images of the patient's vascular system. Optionally, the actual data includes a portion of the vascular system which includes at least one blood vessel with stenosis. In these embodiments, the first model describes a portion of the vasculature system which includes at least one blood vessel with stenosis. This model is interchangeably referred to as a stenotic model. Optionally, the actual data includes a portion of the vascular system which includes at least one blood vessel with stenosis and a crown. In these embodiments the stenotic model also includes information pertaining to the shape and/or volume of the crown, and information pertaining to blood flow and/or resistance to blood flow in the crown.

In some embodiments the first model is used for calculating an index indicative of vascular function. Preferably, the index is also indicative of potential effect of revascularization. For example, the index can be calculated based on a volume of a crown in the model and on a contribution of a stenosed vessel to the resistance to blood flow in the crown.

In some embodiments of the present invention a second model is produced from the actual data, changed so that one or more stenoses present in the patient's vascular system are modeled as if they had been revascularized.

In some embodiments the first model and the second model are compared, and the index indicative of the potential effect of revascularization is produced, based on comparing physical characteristics in the first model and in the second model.

In some embodiments the index is a Fractional Flow Reserve (FFR), as known in the art.

In some embodiments the index is some other measure which potentially correlates to efficacy of performing revascularization of one or more vessels, optionally at locations of stenosis.

According to an aspect of some embodiments of the present invention there is provided a method for vascular assessment. The method comprises, receiving a plurality of 2D angiographic images of a portion of a vasculature of a subject; and using a computer for processing the images and producing, within less than 60 minutes, a first vessel tree over a portion of the vasculature.

According to some embodiments of the invention the vasculature has therein at least a catheter other than an angiographic catheter, and wherein the images are processed and the tree is produced while the catheter is in the vasculature.

According to some embodiments of the invention the method comprises using the vascular model for calculating an index indicative of vascular function.

According to some embodiments of the invention the index is indicative of the need for revascularization.

According to some embodiments of the invention the calculation is within less than 60 minutes.

According to an aspect of some embodiments of the present invention there is provided a method of analyzing angiographic images. The method comprises: receiving a plurality of 2D angiographic images of a portion vasculature of a subject; and using a computer for processing the images to produce a tree model of the vasculature.

According to an aspect of some embodiments of the present invention there is provided a method of treating a vasculature. The method comprises: capturing a plurality of 2D angiographic images of a vascular system of a subject being immobilized on a treatment surface; and, while the subject remains immobilized: processing the images and producing a vessel tree over the vascular system; identifying a constricted blood vessel in the tree; and inflating a stent at a site of the vasculature corresponding to the constricted blood vessel in the tree.

According to some embodiments of the invention the plurality of 2D angiographic images comprise at least three 2D angiographic images, wherein the tree model is a 3D tree model.

According to some embodiments of the invention the method comprises identifying in the first vessel tree a stenosed vessel and a crown of the stenosed vessel, and calculating a resistance to fluid flow in the crown; wherein the index is calculated based on a volume of the crown, and on a contribution of the stenosed vessel to the resistance to fluid flow.

According to some embodiments of the invention the vessel tree comprises data pertaining to location, orientation and diameter of vessels at a plurality of points within the portion of the vasculature.

According to some embodiments of the invention the method comprises processing the images to produce a second three-dimensional vessel tree over the vasculature, the second vessel tree corresponding to the first vessel tree in which a stenotic vessel is replaced with an inflated vessel; wherein the calculation of the index is based on the first tree and the second tree.

According to some embodiments of the invention the method comprises processing the images to produce a second three-dimensional vessel tree over the vasculature, the second vessel tree corresponding to a portion of the vascular system which does not include a stenosis and which is geometrically similar to the first vessel tree; wherein the calculation of the index is based on the first tree and the second tree.

According to some embodiments of the invention the method comprises obtaining a Fractional Flow Ratio (FFR) based on the index.

According to some embodiments of the invention the method comprises determining, based on the index, a ratio between maximal blood flow in an area of a stenosis and a maximal blood flow in a same area without stenosis.

According to some embodiments of the invention the method comprises minimally invasively treating a stenosed vessel.

According to some embodiments of the invention the treatment is executed less than one hour from the calculation of the index.

According to some embodiments of the invention the method comprises storing the tree in a computer readable medium.

According to some embodiments of the invention the method comprises transmitting the tree to a remote computer.

According to some embodiments of the invention the invention the method comprises capturing the 2D angiographic images.

According to some embodiments of the invention the capturing the plurality of 2D angiographic images is effected by a plurality of imaging devices to capture the plurality of 2D angiographic images.

According to some embodiments of the invention the capturing the plurality of 2D angiographic images comprises synchronizing the plurality of imaging devices to capture the plurality of images substantially at a same phase during a heart beat cycle.

According to some embodiments of the invention the synchronizing is according to the subject's ECG signal.

According to some embodiments of the invention the method comprises: detecting corresponding image features in each of N angiographic images, where N is an integer greater than 1; calculating image correction parameters based on the corresponding image features; and based on the correction parameters, registering N−1 angiographic images to geometrically correspond to an angiographic image other than the N−1 angiographic images.

According to some embodiments of the invention the method comprises defining a surface corresponding to a shape of the heart of the subject, and using the surface as a constraint for the detection of the corresponding image features.

According to some embodiments of the invention the method comprises compensating for breath and patient movement.

According to an aspect of some embodiments of the present invention there is provided a computer software product. The computer software product comprises a computer-readable medium in which program instructions are stored, which instructions, when read by a computer, cause the computer to receive a plurality of 2D angiographic images of a subject's vascular system and execute the method as delineated above and optionally as further detailed below.

According to an aspect of some embodiments of the present invention there is provided a system for vascular assessment. The system comprises: a plurality of imaging devices configured for capturing a plurality of 2D angiographic images of a vascular system of a subject; and a computer configured for receiving the plurality of 2D images and executing the method the method as delineated above and optionally as further detailed below.

According to an aspect of some embodiments of the present invention there is provided a system for vascular assessment comprising: a computer functionally connected to a plurality of angiographic imaging devices for capturing a plurality of 2D images of a portion of vasculature of a subject, configured to: accept data from the plurality of angiographic imaging devices; and process the images to produce a tree model of the vasculature, wherein the tree model comprises geometric measurements of the vasculature at one or more locations along a vessel of at least one branch of the vasculature.

According to some embodiments of the invention the system comprises a synchronization unit configured to provide the plurality of angiographic imaging devices with a synchronization signal for synchronizing the capturing of the plurality of 2D images of the vasculature.

According to some embodiments of the invention the computer is configured to accept a subject ECG signal, and to select, based on the ECG signal, 2D images corresponding to substantially a same phase during a heart beat cycle.

According to some embodiments of the invention the system comprises an image registration unit configured for: detecting corresponding image features in each of N angiographic images, where N is an integer greater than 1; calculating image correction parameters based on the corresponding image features; and based on the correction parameters, registering N−1 angiographic images to geometrically correspond to an angiographic image other than the N−1 angiographic images.

According to some embodiments of the invention the computer is configured for defining a surface corresponding to a shape of the heart of the subject, and using the surface as a constraint for the detection of the corresponding image features.

According to some embodiments of the invention the computer is configured for compensating for breath and patient movement.

According to some embodiments of the invention the compensating comprises iteratively repeating the detection of the corresponding image features each time for a different subset of angiographic images, and updating the image correction parameters responsively to the repeated detection of the corresponding image features.

According to some embodiments of the invention N is greater than 2. According to some embodiments of the invention N is greater than 3.

According to some embodiments of the invention the corresponding image features comprise at least one of a group consisting of an origin of the tree model, a location of minimal radius in a stenosed vessel, and a bifurcation of a vessel.

According to some embodiments of the invention the tree model comprises data pertaining to location, orientation and diameter of vessels at a plurality of points within the portion of the vasculature.

According to some embodiments of the invention tree model comprising measurements of the vasculature at one or more locations along at least one branch of the vasculature.

According to some embodiments of the invention the geometric measurements of the vasculature are at one or more locations along a centerline of at least one branch of the vasculature.

According to some embodiments of the invention the tree model comprises data pertaining to blood flow characteristics in at one or more of the plurality of points.

According to some embodiments of the invention the portion of the vasculature comprises the heart arteries.

According to an aspect of some embodiments of the present invention there is provided a method for vascular assessment comprising: receiving a plurality of 2D angiographic images of a portion of a vasculature of a subject, and processing the images to produce a stenotic model over the vasculature, the stenotic model having measurements of the vasculature at one or more locations along vessels of the vasculature; obtaining a flow characteristic of the stenotic model; and calculating an index indicative of vascular function, based, at least in part, on the flow characteristic in the stenotic model.

According to some embodiments of the invention the flow characteristic of the stenotic model comprises resistance to fluid flow.

According to some embodiments of the invention the invention the method comprises identifying in the first stenotic model a stenosed vessel and a crown of the stenosed vessel, and calculating the resistance to fluid flow in the crown; wherein the index is calculated based on a volume of the crown, and on a contribution of the stenosed vessel to the resistance to fluid flow.

According to some embodiments of the invention the flow characteristic of the stenotic model comprises fluid flow.

According to some embodiments of the invention the stenotic model is a three-dimensional vessel tree.

According to some embodiments of the invention the vessel tree comprises data pertaining to location, orientation and diameter of vessels at a plurality of points within the portion of the vasculature.

According to some embodiments of the invention the processing comprises: extending the stenotic model by one bifurcation; calculating a new flow characteristic in the extended stenotic model; updating the index responsively to the new flow characteristic and according to a predetermined criterion; and iteratively repeating the extending, the calculating and the updating.

According to some embodiments of the invention the method comprises processing the images to produce a second model over the vasculature, and obtaining a flow characteristic of the second model; wherein the calculation of the index is based on the flow characteristic in the stenotic model and on the flow characteristic in the second model.

According to some embodiments of the invention the method the second model is a normal model, comprising an inflated vessel replacing a stenotic vessel in the stenotic model.

According to some embodiments of the invention the stenotic model is a three-dimensional vessel tree and the second model is a second three-dimensional vessel tree.

According to some embodiments of the invention each of the models corresponds to a portion of the vasculature which is between two consecutive bifurcations of the vasculature and which includes a stenosis.

According to some embodiments of the invention each of the models corresponds to a portion of the vasculature which includes a bifurcation of the vasculature.

According to some embodiments of the invention each of the models corresponds to a portion of the vasculature which includes a stenosis and which extends at least one bifurcation of the vasculature beyond the stenosis.

According to some embodiments of the invention the each of the models corresponds to a portion of the vasculature which includes a stenosis and which extends at least three bifurcations of the vasculature beyond the stenosis.

According to some embodiments of the invention the method wherein each of the models corresponds to a portion of the vasculature which includes a stenosis and which extends distally as far as resolution of the images allows.

According to some embodiments of the invention the stenotic model corresponds to a portion of the vasculature which includes a stenosis, and the second model corresponds to a portion of the vasculature which does not include a stenosis and which is geometrically similar to the stenotic model.

According to some embodiments of the invention the processing comprises: extending each of the models by one bifurcation; calculating a new flow characteristic in each extended model; updating the index responsively to the new flow characteristics and according to a predetermined criterion; and iteratively repeating the extending, the calculating and the updating.

According to some embodiments of the invention the index is calculated based on a ratio of the flow characteristic in the stenotic model to the flow characteristic in the second model.

According to some embodiments of the invention the index is indicative of the need for revascularization.

According to an aspect of some embodiments of the present invention there is provided a method for vascular assessment including producing a stenotic model of a subject's vascular system, the stenotic model including measurements of the subject's vascular system at one or more locations along a vessel centerline of the subject's vascular system, obtaining a flow characteristic of the stenotic model, producing a second model, of a similar extent of the subject's vascular system as the stenotic model, obtaining the flow characteristic of the second model, and calculating an index indicative of the need for revascularization, based on the flow characteristic in the stenotic model and on the flow characteristic in the second model.

According to some embodiments of the invention, the second model is a normal model, including an inflated vessel replacing a stenotic vessel in the stenotic model.

According to some embodiments of the invention, the vascular system includes the subject's heart arteries.

According to some embodiments of the invention, the producing a stenotic model of a subject's vascular system includes using a plurality of angiographic imaging devices for capturing a plurality of 2D images of the subject's vascular system, and producing the stenotic model based on the plurality of 2D images.

According to some embodiments of the invention, the flow characteristic includes fluid flow.

According to some embodiments of the invention, the obtaining the flow characteristic of the stenotic model includes measuring fluid flow in the subject's vascular system at the one or more locations in the extent of the subject's vascular system included in the stenotic model, and the obtaining the flow characteristic of the second model includes calculating fluid flow in the subject's vascular system at the one or more locations in the extent of the subject's vascular system included in the second model, based, at least in part, on correcting the fluid flow of the stenotic model to account for an inflated vessel.

According to some embodiments of the invention, the flow characteristic includes resistance to fluid flow.

According to some embodiments of the invention, the obtaining the flow characteristic of the stenotic model includes calculating a resistance to flow based, at least in part, on the subject vascular system cross sectional area at the one or more locations in the extent of the subject's vascular system included in the stenotic model, and obtaining the flow characteristic of the second model includes calculating the resistance to flow based, at least in part, on the subject vascular system inflated cross sectional area at the one or more locations in the extent of the subject's vascular system included in the second model.

According to some embodiments of the invention, the extent of each one of the stenotic model and the second model includes a segment of the vascular system, between two consecutive bifurcations of the vascular system, which includes a stenosis.

According to some embodiments of the invention, the extent of each one of the stenotic model and the second model includes a segment of the vascular system which includes a bifurcation of the vascular system.

According to some embodiments of the invention, each one of the stenotic model and the second model include an extent of the vascular system which includes a stenosis and extends at least one bifurcation of the vascular system beyond the stenosis.

According to some embodiments of the invention, each one of the stenotic model and the second model include an extent of the vascular system which includes a stenosis and an inflated stenosis respectively and extends at least three bifurcations of the vascular system beyond the stenosis.

According to some embodiments of the invention, each one of the stenotic model and the second model include an extent of the vascular system which includes a stenosis and extends distally as far as resolution of an imaging modality allows.

According to some embodiments of the invention, each one of the stenotic model and the second model include an extent of the vascular system which includes a stenosis and extends distally at least one bifurcation of the vascular system beyond the stenosis, and further including storing the flow characteristic of the stenotic model as a previous flow characteristic of the stenotic model and storing the flow characteristic of the second model as a previous flow characteristic of the second model, extending the extent of the stenotic model and the second model by one more bifurcation, calculating a new flow characteristic in the stenotic model and calculating a new flow characteristic in the second model, deciding whether to calculate the index indicative of the need for revascularization as follows: if the new flow characteristic of the stenotic model differs from the previous characteristic of the stenotic model by less than a first specific difference, and the new flow characteristic of the second model differs from the previous characteristic of the second model by less than a second specific difference, then calculating the index indicative of the need for revascularization, else repeating the storing, the extending, the calculating, and the deciding.

According to some embodiments of the invention, the stenotic model includes an extent of the vascular system which includes a stenosis, the second model includes an extent of the vascular system which does not include a stenosis and which is geometrically similar to the first model.

According to some embodiments of the invention, the index is calculated as a ratio of the flow characteristic in the stenotic model to the flow characteristic in the second model.

According to some embodiments of the invention, the calculated index is used to determine a Fractional Flow Ratio (FFR).

According to some embodiments of the invention, the calculated index is used to determine a ratio between maximal blood flow in an area of stenosis and a maximal blood flow in a same area without stenosis.

According to some embodiments of the invention, the producing a stenotic model, the obtaining a flow characteristic of the stenotic model, the producing a second model, the obtaining the flow characteristic of the second model, and the calculating an index, are all performed during a diagnostic catheterization, before a catheter used for the diagnostic catheterization is withdrawn from the subject's body.

According to an aspect of some embodiments of the present invention there is provided a method for vascular assessment including capturing a plurality of 2D angiographic images of a subject's vascular system, producing a tree model of the subject's vascular system, the tree model including geometric measurements of the subject's vascular system at one or more locations along a vessel centerline of at least one branch of the subject's vascular system, using at least some of the plurality of captured 2D angiographic images, and producing a model of a flow characteristic of the first tree model.

According to some embodiments of the invention, the vascular system includes the subject's heart arteries.

According to some embodiments of the invention, the capturing a plurality of 2D angiographic images includes using a plurality of imaging devices to capture the plurality of 2D angiographic images.

According to some embodiments of the invention, the capturing a plurality of 2D angiographic images includes synchronizing the plurality of imaging devices to capture the plurality of images at a same moment.

According to some embodiments of the invention, the synchronizing uses the subject's ECG signal.

According to some embodiments of the invention, the synchronizing includes detecting corresponding image features in at least a first 2D angiographic image and a second 2D angiographic image of the plurality of 2D angiographic images, calculating image correction parameters based on the corresponding image features, and registering at least the second 2D angiographic image to geometrically correspond to the first 2D angiographic image, wherein the corresponding image features include at least one of a group consisting of an origin of the tree model, a location of minimal radius in a stenosed vessel, and a bifurcation of a vessel.

According to an aspect of some embodiments of the present invention there is provided a system for vascular assessment including a computer functionally connected a plurality of angiographic imaging devices for capturing a plurality of 2D images of a patient's vascular system, configured to accept data from the plurality of angiographic imaging devices, produce a tree model of the subject's vascular system, wherein the tree model includes geometric measurements of the subject's vascular system at one or more locations along a vessel centerline of at least one branch of the subject's vascular system, using at least some of the plurality of captured 2D images, and produce a model of flow characteristics of the tree model.

According to some embodiments of the invention, the vascular system includes the subject's heart arteries.

According to some embodiments of the invention, further including a synchronization unit configured to provide the plurality of angiographic imaging devices with a synchronization signal for synchronizing the capturing of the plurality of 2D images of the subject's vascular system.

According to some embodiments of the invention, further including a synchronization unit configured to accept a subject ECG signal, and to select 2D images from the data from the plurality of angiographic imaging devices at a same cardiac phase in the 2D images.

According to some embodiments of the invention, further including an image registration unit configured to detect corresponding image features in at least a first 2D image and a second 2D image from the data from the plurality of angiographic imaging devices, to calculate image correction parameters based on the corresponding image features, and to register at least the second 2D image to geometrically correspond to the first 2D image, wherein the corresponding image features include at least one of a group consisting of an origin of the tree model, a location of minimal radius in a stenosed vessel, and a bifurcation of a vessel.

According to an aspect of some embodiments of the present invention there is provided a method for vascular assessment including producing a stenotic model of a subject's vascular system, the stenotic model including geometric measurements of the subject's vascular system at one or more locations along a vessel centerline of the subject's vascular system, including an extent of the vascular system which includes a stenosis and extends at least one bifurcation of the vascular system beyond the stenosis, obtaining a flow characteristic of the stenotic model, producing a second model, of a similar extent of the subject's vascular system as the stenotic model, obtaining the flow characteristic of the second model, and calculating an index indicative of the need for revascularization, based on the flow characteristic in the stenotic model and on the flow characteristic in the second model, and further including storing the flow characteristic of the stenotic model as a previous flow characteristic of the stenotic model and storing the flow characteristic of the second model as a previous flow characteristic of the second model, extending the extent of the stenotic model and the second model by one more bifurcation, calculating a new flow characteristic in the stenotic model and calculating a new flow characteristic in the second model, deciding whether to calculate the index indicative of the need for revascularization as follows: if the new flow characteristic of the stenotic model differs from the previous characteristic of the stenotic model by less than a first specific difference, and the new flow characteristic of the second model differs from the previous characteristic of the second model by less than a second specific difference, then calculating the index indicative of the need for revascularization, else repeating the storing, the extending, the calculating, and the deciding.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon Implementation of the method and/or system of embodiments of the invention can involve performing or completing selected tasks manually, automatically, or a combination thereof.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions.

Optionally, the data processor includes a volatile memory for storing instructions and/or data and/or a non-volatile storage, for example, a magnetic hard-disk and/or removable media, for storing instructions and/or data. Optionally, a network connection provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIG. 3A is an image of a coronary vessel tree model, produced according to some exemplary embodiments of the invention;

FIG. 3B is an image of a coronary vessel tree model of FIG. 3A, with tree branch tags added according to some exemplary embodiments of the invention;

FIG. 3C is a simplified illustration of a tree model of a coronary vessel tree, produced according to some exemplary embodiments of the invention;

DESCRIPTION OF SPECIFIC EMBODIMENTS OF THE INVENTION

Figure 1:
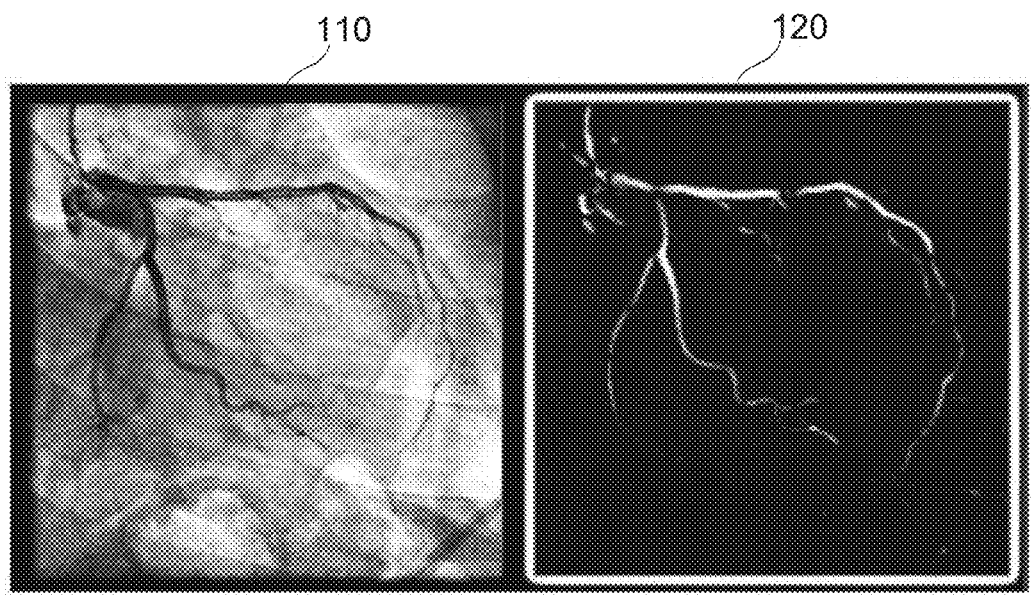
FIG. 1 depicts an original image and a Frangi-filter processed image, processed according to some exemplary embodiments of the invention.

The present invention, in some embodiments thereof, relates to vascular modeling, and, more particularly, but not exclusively, to the use of a vascular model for producing indices relating to vascular function and diagnosis in real time—for example, during a catheterized imaging procedure.

A broad aspect of some embodiments of the current invention relates to calculation of a fractional flow reserve (FFR) index based on an imaging of a portion of a vascular system.

An aspect of some embodiments of the invention relates to calculation of a model of vascular flow in a subject. In some embodiments, the portion of the vascular system which is imaged is coronary vasculature. In some embodiments, the vasculature is arterial. In some embodiments, vascular flow is modeled based on vascular diameter in 3-D reconstruction of a vascular tree. Optionally, vascular resistance is determined based on vascular diameter. Optionally, vascular resistance is calculated for a stenotic vessel, and for its vascular crown (vessels downstream of the stenotic vessel). In some embodiments, the FFR is calculated from a general 3-D reconstruction of a vascular tree, for example, of a vascular tree reconstruction from a CT scan. In some embodiments, reconstruction is performed de novo, for example, from 2-D angiographic image data. Optionally, a provided vascular tree is suited to the specific requirements of FFR calculation, for example, by reduction to a graph representation of vascular width as a function of vascular extent.

An aspect of some embodiments of the invention relates to calculation of FFR based on differences in flow between a vascular model of a potentially stenotic vasculature, and a different vascular model derived from and/or homologous to the stenotic vasculature model. In some embodiments, changes to create an astenotic version of the vascular model comprise determinations of wall opening (widening) in stenotic regions based on reference width measurements obtained in one or more other portions of the vasculature. In some embodiments, reference width measurements are obtained from vascular portions on either side of a stenosis. In some embodiments, reference width measurements are obtained from a naturally astenotic vessel at a similar branch order to a stenotic segment.

In some embodiments of the invention, the FFR index comprises a ratio of flow in model comprising a potentially stenotic vascular segment to a model wherein said segment is replaced by a lower flow-resistance segment, and/or the resistance to flow due to said segment is removed. A potential advantage of this ratio determination is that the index comprises an expression of the effect of a potential therapeutic treatment to a vasculature, for example, an opening of a vascular region by percutaneous coronary intervention (PCI) such as stent implantation. Another potential advantage of this ratio that it measures a parameter (fractional flow reserve) which, though well-accepted as providing an indication of a need for revascularization, is commonly determined in the art by invasive pressure measurements requiring direct access to both sides of stenotic lesion.

A broad aspect of some embodiments of the current invention relates to generation of a vascular tree model.

An aspect of some embodiments of the invention relates to construction of a tree model of a portion of a mammalian vasculature, based on automatic matching of features homologous among multiple vascular images. In some embodiments of the invention, the tree model comprises vascular segment centerlines. Optionally, the homologous matching is among vascular segment centerlines and/or portions thereof. In some embodiments, the modeled spatial relationship among vascular segment centerlines comprises association of segment ends at branch nodes.

A potential advantage of using vascular segment centerlines, and/or other features readily identifiable from vascular segment data in an image, is that they provide a rich "metafeature" which can be subjected to ray intersection tests by back-projecting rays from pairs (or a larger plurality) of individual images into a 3-D space based on the imaging configuration. In some embodiments, precise ray intersections are unnecessary; intersections within a volume are sufficient to establish homology. While isolated features are potentially useful for such intersection-based homology identifications, it should be noted that the extended character of paths along vascular segments (for example) allows the use, in some embodiments, of correlation and/or constraint techniques for further refinement of initial, potentially tentative homology identifications. Ray intersections thus, in some embodiments, take the place of manual identification of homologous features in different vascular projections.

In some embodiments of the invention, the modeled vasculature comprises vasculature of a heart (cardiac vasculature), and specifically, of a coronary artery and its branches. In some embodiments, the tree model comprises 3-D position information for the cardiac vasculature.

An aspect of some embodiments of the invention relates to position (and, in particular, 3-D spatial position) in a model of cardiac vasculature being based on and/or derived through coordinates defined by features of the vasculature itself. In some embodiments, the same vascular features (for example, vascular centerlines) both define the 3-D space of the model, and additionally comprise the backbone of the model itself.

Optionally, centerlines are represented according to both their 3-D positions in space, and as positions in a graph space defined by to a vascular tree comprising connected segments of centerlines at nodes. In some embodiments, a vascular segment comprises data associated with a blood vessel path (for example, a vascular centerline) connecting two branch nodes.

In some embodiments of the invention, a "consensus" 3-D space defined by matching among vascular feature positions is a result of tree model construction.

A potential advantage of this vascular-centered modeling approach relates to the heart (to which the vasculature is mechanically coupled) being in continual motion. In some embodiments, a vasculature model is built up from a series of 2-D images taken sequentially. During a period of cardiovascular imaging and/or among imaging positions, regions of the vasculature potentially change their actual and/or calibrated positions (absolute and/or relative) in 3-D space. This is due, for example, to the beating of the heart, respiration, voluntary movements, and/or misalignments in determining image projection planes. In some embodiments, an imaging protocol is modified to correct for these motions to an extent, for example, by synchronizing the moment of imaging to a particular phase of the cardiac cycle (end of diastole, for example). Nevertheless, errors potentially remain even after such after this, due, for example, to the natural variability of the cardiac cycle, effects of different physiological cycles (such as heart and respiration) being out of phase, and limitations in the period for imaging available. Thus, potentially, there is no "natural" 3-D space common to the raw 2-D image data. Targeting a consensus space potentially allows reframing the modeling problem in terms of consistency of modeling results.

While 3-D position changes, other features of vascular position, for example, connectivity, and/or ordering of regions along the vasculature, are invariant with respect to motion artifacts. It is a potential advantage, accordingly, to use features of the vasculature itself to determine a frame of reference within which a 3-D reconstruction can be established. In some embodiments, features on which 3-D reconstruction is based comprise 2-D centerlines of vessel segments present in a plurality of images, among which homologies are established by automatic, optionally iterative methods. A potential advantage of using centerlines as the basis of 3-D modeling is that the centerlines which anchor building the model tree are also useful as 1-D coordinate systems in their own right. Thus, using centerlines as the reconstruction basis helps assure consistency and/or continuity of tree model features associated with centerline position.

In some embodiments, other features related to the vasculature are used as landmarks, for example, points of minimal vascular width, vascular branch points, and/or vascular origin. Optionally, vascular features such as centerlines are transformed alongside transformations to the landmark features (without themselves being the target of cross-image matching), before being integrated into the vascular tree model.

An aspect of some embodiments of the invention relates to the use of iterative projections and back-projections between 2-D and 3-D coordinate systems to arrive at a consensus coordinate system which relates 2-D image planes to a 3-D system of target coordinates.

In some embodiments of the invention, assignment of consensus 3-D positions to landmark vascular features (for example, vascular centerlines) projected during imaging from a single target region to a plurality of 2-D images comprises re-projection and/or re-registration of the 2-D images themselves, the better to match a "consensus" 3-D space. Optionally, re-projection assigns to a 2-D image an image plane which is different from the one originally recorded for it. Optionally, re-registration comprises non-linear distortions of the image, for example, to compensate for deformations of the heart during imaging. Optionally, the re-projection and/or re-registration are performed iteratively, for example, by defining different image groups as "target" and "matching" on different feature registration iterations. In some embodiments of the invention, a different number of images is used for defining homologous features, and for subsequent analysis of additional image features (such as vascular width) to which said homologous features are related.

An aspect of some embodiments of the invention relates to reductions in the calculation complexity of tree determination, allowing more rapid processing to reach clinical conclusions.

In some embodiments, a portion of the image data (for example, "non-feature" pixel values) are optionally maintained in 2-D representations, without a requirement for full 3-D reconstruction. In some embodiments, for example, calculation of the 3-D positions of non-landmark features such as vascular wall positions, is thereby avoided, simplified, and/or postponed. In particular, in some embodiments, vascular edges are recognized from direct processing of 2-D image data (for example, comprising inspection of image gradients perpendicular to vascular centerlines). Optionally, determined edges are projected into 3-D space (represented, for example, as one or more radii extending perpendicularly from 3-D centerline positions), without a requirement to project original image pixel data into 3-D voxel representations.

Additionally or alternatively, vascular wall positions are determined and/or processed (for example, to determine vascular resistance) within one or more "1-D" spaces defined by a frame of reference comprising position along a centerline.

Optionally, this processing is independent, for example, of any projection of wall position into a 3-D space. In some embodiments, reduction of the model to a 1-D function of centerline position reduces a complexity of further calculation, for example, determine a vascular flow characteristic.

An aspect of some embodiments of the invention relates to relationships among vascular model components having different dimensionality. In some embodiments, 1-D, 2-D and/or 3-D positions, and/or logical connectivity, and/or characteristics comprising non-positional or partially non-positional properties are related to one another by direct functions, and/or indirectly through intermediate frames of reference.

In some embodiments, for example, a vascular model comprises one or more of the following features:
  2-D images having positions in a 3-D space defined by relationships among homologous features therein;
  Vascular extents comprising one or more 1-D axes for functions of one or more vascular characteristics, for example diameter, radius, flow, flow resistance, and/or curvature;
  Vascular extents comprising one or more 1-D axes for functions of position in 3-D space;
  Connectivity among vascular extents, described as nodes relative to positions along vascular extents (for example, nodes connecting the ends of vascular segments);
  2-D images into which 1-D axes of vascular extents are mapped;
  2-D frames comprising vascular extent along one axis, and image data orthogonal to the vascular extent along a second axis.

A broad aspect of some embodiments of the current invention relates to real-time determination of a vascular tree model and/or use thereof to provide clinical diagnostic information during a period when a catheterization procedure for a subject is underway.

An aspect of some embodiments of the invention relates to taking advantage of real-time automatic vascular state determination to interact with a clinical procedure as it is underway. Real-time determination, in some embodiments, comprises determination within the time-frame of a catheterization procedure, for example 30 minutes, an hour, or a lesser, greater, or intermediate time. More particularly, real-time determination comprises a determination which is timely for affecting decisions and/or outcomes of a catheterization procedure, that begins with the images that vascular state determination is based on. For example, it is a potential advantage to select a particular portion of a vascular tree for initial calculations, where it is likely that the calculation will be completed in a sufficiently short time to affect a decision to perform a particular PCI procedure, such as implantation of a stent. For example, a 5 minute delay for calculation of FFR comprising two main vascular branches can, when a first branch appears to be of particular interest based on a cursory review of image data, potentially be reduced to a 2.5 minute delay, by selecting the first branch to be the initial target of computations. Additionally or alternatively, rapid calculation allows FFR results to be updated one or more times during the course of a catheterization procedure. For example, a first stent implantation potentially changes perfusion state at other sites sufficiently to induce autoregulatory changes in vascular width, which in turn could change the expected impact of a subsequent stent implantation. Also for example, the imaged effects of an actual stent implantation on vascular width can be compared to predicted effects, in order to verify that a desired effect on flow capacity has been achieved. In some embodiments of the invention, provision is made to allow interface control of how a vascular model and/or a vascular characteristic is calculated, to control model updates based on newly available image data, and/or to select comparison among real and/or predicted vascular state models.

An aspect of some embodiments of the invention relates to building of a vascular tree model which is suited to targeted prediction of the results of a potential clinical intervention. Optionally, the clinical intervention is a PCI procedure such as implantation of a stent. In some embodiments of the invention, targeting comprises focusing stages of vascular tree model construction such that they lead directly to a before/after result in terms of a vascular parameter which is available for clinical modification. In some embodiments, the vascular parameter is vascular width (modifiable, for example, by stent implantation). A potential advantage of focusing modeling on determining a difference between before- and after-treatment states of a vasculature is that the effects of model simplifications due to approximations of other vascular details potentially cancel out (and/or are reduced in magnitude). In particular, they are potentially reduced in importance relative to an operational concern such as: "will the change created by an intervention usefully improve the clinical situation in terms of the known effects of the variable which the intervention targets?" As one potential result, calculations which might otherwise be performed to fully model functional and/or anatomical properties of a vasculature can be omitted. Potentially, this increases the speed with which a flow index can be produced.

An aspect of some embodiments of the invention relates to the formulation of a model representation of a vasculature targets provision of a framework for structuring one or more selected, clinically relevant parameters (such as vascular width, flow resistance and flow itself). In some embodiments, the structure comprises a vascular-extent approach to modeling, in which position along blood vessel segments provides the frame of reference. Optionally, the vascular-extent frame of reference comprises a division among node-linked branches of a vascular tree. Potentially, this comprises a reduction in dimensionality which saves calculation time.

In some embodiments, a model of 3-D positions in a vascular model is formed from potentially incomplete or inaccurate initial positional information. This is achieved, for example, by annealing to a self-consistent framework by an iterative process of adjusting the positional information to achieve greater consistency among the acquired data. Adjusting comprises, for example, operations such as transforming image planes, deforming images themselves to achieve greater similarity, and/or discarding outliers which interfere with determination of a consensus. Potentially, an alternative approach which seeks to ensure fidelity of the framework to a particular real-world configuration (for example, the "real" 3-D configuration or configurations of a portion of a vasculature in space) is computationally expensive relative to the benefit gained for estimation of targeted parameters. In contrast, a framework for which the emphasis is placed on internal consistency in the service of supporting calculations relating to a target parameter can make use of a consensus-like approach to potentially reduce computational load. In particular, this approach is potentially well suited to be combined with a calculation of a change in a vascular system, as described hereinabove.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

It is noted that in example embodiments described below, the coronary vessel system, and more specifically the coronary artery system, is used. The example is not meant to limit embodiments of the invention to the coronary arteries, as embodiments of the invention potentially apply to other vessel systems, such as, for example, the vein system and the lymph system.

In some embodiments, a first model of vascular flow in a subject, based on imaging the subject's vascular system, is constructed. Typically, the first model is constructed of a vascular system which includes a problem section of the vascular system, such as a stenosis in at least part of a vessel. In some embodiments of the present invention, the first model corresponds to a portion of the vascular system which includes at least one blood vessel with stenosis. In these embodiments, the first model describes a portion of the vasculature system which includes at least one blood vessel with stenosis and a crown. In these embodiments the first model optionally includes information pertaining to the shape and/or volume of the crown, and information pertaining to blood flow and/or resistance to blood flow in the stenosed blood vessel and/or the crown.

Typically, but not necessarily, a second model is constructed. The second model optionally describes an at least partially healthier vascular system corresponding to the first model. In some embodiments the second model is constructed by changing a stenosis in the first model to be more open, as it would be if a stent were to open the stenosis; and in some embodiments the second model is constructed by choosing a section of the subject's vascular system which includes a healthy vessel similar to the problem vessel of the first model, and using it to replace a stenosed vessel.

Vascular model construction is described hereinbelow.

In some embodiments, an index indicative of the need for revascularization is calculated. This can be done based on the first model or based on a comparison between the first and the second models of the vascular flow. The index is optionally used similarly to the pressure measurement-derived FFR index, to assess whether a stenosed vessel affects flow in the vascular system to such an extent that the prognosis for improvement in the subject's condition following inflation of the stenosed vessel is higher than the likelihood for complications resulting from the inflation itself.

The terms "FFR" and "FFR index" in all their grammatical forms are used throughout the present specification and claims to stand for the above-mentioned index, and not only for the FFR index mentioned in the Background section as an invasive measurement involving insertion of a guidewire equipped with a miniature pressure transducer across the stenosis. In some instances—in particular where distinctions among specific types of FFR and FFR-like indices are discussed—a subscript is used to distinguish them, for example $FFR_{pressure}$ for FFR derived from pressure measurements, and/or $FFR_{flow}$ where FFR is expressed in terms of flow determinations.

Acquiring data for constructing a vascular model

In some embodiments, data for modeling a vascular system comprises medical imaging data.

In some embodiments of the invention, the data is from minimally invasive angiographic images, for example, X-ray images. In some embodiments, the angiographic images are two-dimensional (2-D). In some embodiments, 2-D angiographic images taken from different viewing angles are combined to produce a model including three-dimensional (3-D) data, for example, from 2, 3, 4 or more viewing angles.

In some embodiments, the data is from computerized tomography (CT) scans. It should be noted that with present-day technology, angiographic images provide a finer resolution than CT scans. Models of the vascular system constructed based on angiographic images, whether one-dimensional (1-D) tree models or full 3-D models, are potentially more accurate than models based on CT scans, and potentially provide a more accurate vascular assessment.

Speed of Results

An object in some embodiments of the present invention related to real-time use is rapid calculation of a vascular model, and of anatomical and/or functional parameters thereof, in order to provide feedback for real-time diagnostic decision making.

In some embodiments of the invention, the feedback relevant to making a decision for an intervention (for example, in a particular region, or at all) is dividable into three broad categories: "recommend to intervene", "recommend not to intervene", and "no recommendation". Optionally, feedback is presented in such a format.

Optionally, categorization itself is performed by a physician, based on a provided index, which is a number, graph, category description, and/or another output, having a number of output states which is a plurality of output states, a continuous range of output states or any number of states in between. Furthermore, in some embodiments of the invention, diagnostic feedback is related and/or easily relatable to clinical outcome, for example by producing an index which is easily related to (and potentially interchangeable with) indexes already established in the field, such as $FFR_{pressure}$, a scoring method such as the SYNTAX score, or another method of vascular assessment.

In some embodiments of the invention, vascular tree construction is optimized for the production of vascular segment pathways, for example, vascular segment centerlines. From this stage (or from the results of another process producing a vascular tree from which the positions of vascular extent are easily determined), calculations for determination of one or more diagnostically significant indexes is potentially very rapid, so long as appropriate index target is sought.

Related to the selection of an appropriate index target, another object in some embodiments of the present invention related to real-time use is the use of a flow parameter which can be calculated extremely rapidly, given a vascular tree, while still producing a diagnostic index which is accurate enough to be usable as a clinical decision making tool. One aid to obtaining such an index, in some embodiments, is the availability of a deep vascular tree (3, 4, or more branches), such that resistance to flow throughout a large extent of the vascular network can be calculated with respect to the impact on flow through a particular segment in both a stenosed (narrowed) and an astenotic (widened) state. In some embodiments, any well-defined vascular tree either constructed as described herein for X-ray angiographic images, but also as potentially available from another imaging method such as rotational angiography and/or CT angiography, potentially serves as an input for image-based FFR computation. "Well-defined" comprises, for example, having a branch depth of 3, 4 or more vascular branches. Additionally or alternatively, "Well-defined" comprises, for example, imaging resolution sufficient to model vascular width with an accuracy of within 5%, 10%, 15% or another larger, smaller, or intermediate value of true vascular width.

In some embodiments of the invention, a focus on the production of a treatment recommendation guides the choice of image analysis methods, such that rapid provision of diagnostic feedback is more readily obtained. In particular, in some embodiments, a goal is to provide an analysis of whether or not a particular revascularization intervention will restore clinically meaningful blood flow. It is a potential advantage in creating a vascular model to focus on the modeling of measurable parameters which are targeted for change in a clinical intervention, as it is due to these changes that the effects of a proposed treatment (if any) will be felt. Furthermore, such a focus optionally allows unchanging and/or equivalent parameters to be simplified and/or disregarded, at least to the extent that they do not affect the desirability of a treatment outcome. Thus, for example, potentially no modeling of dynamic flow is necessary to arrive at a diagnostic index of vascular function.

In some embodiments of the invention, a sufficient analysis to produce a useful recommendation for PCI and/or CABG (coronary artery bypass grafting) comprises analysis of one or more features which are readily determined as a local function of a 1-D parameter such as vascular segment position. For example: vascular resistance, while subject to many variables potentially treatable by a full consideration of a system's fluid dynamics, has a strong dependence on the variable of vascular diameter. Vascular diameter in turn is a target of treatment options such as stent implantation. Moreover, vascular diameter itself (and/or related metrics such as vascular radius, cross sectional area and/or cross-sectional profile), is rapidly calculable from image data along a pathway comprising a description of vascular segment position.

Moreover, a potential advantage of a vascular model optimized for centerline determination is that, for example, calculations relating to less clinically significant details, for example, vascular wall shape, are avoidable and/or postponable. In some embodiments, vascular centerlines provide the central framework of the final model. It is a potential advantage to use the same vascular centerlines (and/or approximations thereto) as features which provide landmarks during a phase of processing which constructs a 3-D coordinate system to which 2-D images from which a 3-D vascular tree will be modeled are registered. Potentially, this avoids a requirement for determination of a second feature set. Potentially, using the same feature set for both registration and the model basis avoids some calculations to overcome inconsistencies due to imaging artifacts, since the skew between registration features and model features is thereby reduced.

In some embodiments of the invention, a full processing period from the receipt of images to the availability of a diagnostically useful metric such as FFR comprises about 2-5 minutes, with the application of relatively modest computational resources (for example, a PC comprising an off-the-shelf multicore CPU and 4 mid-range GPU cards—equivalent to about 8-12 teraflops of raw computational power). On the 5 minute time scale and with this type of equipment, in some embodiments, centerline segmentation of about 200 input images comprises about a half minute of processing time, conversion to a 3-D model about 4 minutes, and remaining tasks, such as FFR calculation, about 10-30 seconds, depending on the extent of the tree which is calculated. It should be noted that further reductions in processing time are expected so long as general processing power cost per teraflop continues to decrease. Furthermore, multiprocessor and/or multicore division of processing tasks can be naturally achieved by divisions along vascular boundaries, for example by dividing work among processing resources based on spatial positions. In some embodiments of the invention, the computation to reconstruct a vascular tree and calculate a flow index comprises less than about 10,000 trillion operations. In some embodiments, the computation comprises less than about 5,000 trillion, 2,000 trillion, 1,000 trillion, 500 trillion, or an intermediate, greater, or lesser number of operations.

Another object of some embodiments of the present invention is the integration of automatic vascular parameter determination from images into the clinical work flow.

In some embodiments, the integration is interactive, in that it comprises interaction between results and/or control of automatic imaging processing and other aspects of a catheterization procedure, while the procedure is underway. For example, in some embodiments of the invention, a medical professional can determine from cursory manual inspection that one of two branches of a vascular tree is a likely first candidate for a vascular intervention such as PCI. In some embodiments of the invention, the first candidate branch is selectable such that processing to determine, for example, an FFR index for that branch completes earlier than calculations for a second branch. Potentially, this allows decision making to occur earlier and/or with a shorter interruption in the procedures being performed on a patient.

In some embodiments of the invention, tree processing is sufficiently rapid that two, three, or more imaging procedures can be performed and analyzed within the course of a single session with the patient. A single session comprises, for example, a period during which a portion of a catheter and/or guidewire remains in a portion of a vascular tree, for example, for intervention to open a stenosis therein; the time is, for example, 30 minutes to an hour, or a lesser, greater, or intermediate period of time. $FFR_{pressure}$, for example, is typically determined in conjunction with an injection of adenosine to maximally widen a patient's vasculature. The safe frequency of adenosine injection is limited, however, so a method of determining an FFR-equivalent index without such an injection provides a potential advantage. A second imaging session is potentially valuable, for example, to verify the results of a stent implantation, as is commonly performed at the level of positioning verification for current stent implantations. Potentially, vascular autoregulation after stent implantation results in changes to vascular width, such that a second imaging session can help determine if a further stent implantation has become and/or remains advisable.

In some embodiments, results of intensive phases of calculation can serve as a basis for recalculation based on further acquired images, and/or recalculation of indices. For example, a previously calculated vascular tree can serve as the basis of registration of one or more images of a post-implantation vasculature, without requiring a full image set to be re-acquired.

In some embodiments of the invention, a user interface to the computer, for example, a graphical user interface, is provided such that one or more interactive user commands are supported. Optionally, for example, one or more user commands is available to focus image processing targets to one or more selected branches of the subject's vasculature. Optionally, one or more commands to change an aspect of a vascular model (for example, to model an astenotic state of a stenotic vessel) is available. Optionally, one or more commands to select among and/or compare vascular models from a plurality of image sets (for example, image sets taken at entirely different times during procedure, and/or image sets comprising views of the heart at different heartbeat cycle phases) is available.

Features of some exemplary vascular models

In some embodiments of the invention, the vascular system model comprises a tree model; optionally a 3-D tree model. However, the spatial dimensionality of the model is optionally adjusted at different anatomical levels and/or stages of processing to suit the requirements of the application. For example, 2-D images are optionally combined to extract 3-D vascular tree information which allows identification and construction of 1-D vascular segment models. 1-D segment models in turn are logically linked, in some embodiments, according to their connectivity, with or without preserving details of their other spatial relationships. In some embodiments, spatial information is collapsed or encoded; for example, by approximating a cross-sectional region by the parameters of a circle (diameter), ellipse (major/minor axis), or other representation. In some embodiments, regions along the vascular tree comprise non-spatial information, for example, flow resistance, calculated flow volume, elasticity, and/or another dynamic or static property associated with an sampled and/or extended vascular segment region, and/or a node of the vascular tree.

In some embodiments, the tree model comprises a tree data structure having nodes linked by curvilinear segments. The nodes are associated with vascular furcations (e.g., bifurcation or trifurcations or multi-furcations), and the curvilinear segments are associated with vessel segments. A curvilinear segment of the tree is also referred to below as a branch, and the entire tree portion distal to a branch is referred to as a crown. Thus, a tree model, in some embodiments of the invention, comprises a description of the vascular system which assigns nodes of the tree to vascular furcations and branches of the tree to vessel segments of the vascular system.

In some embodiments, sample points along branches are associated with vascular diameter information. In such embodiments, the tree can be considered as being represented as a series of disks or poker chips (e.g., circular or elliptical disks) that are linked together to form a 3-D structure containing information relating to the local size, shape, branching, and other structural features at any point in the vascular tree.

In some embodiments, trifurcations and/or multi-furcations are methodically converted to a combination of bifurcations. Optionally, for example, a trifurcation is converted to two bifurcations. The term "furcation" in all its grammatical forms is used throughout the present specification and claims to mean bifurcation, trifurcation, or multi-furcation.

In some embodiments, the tree model includes property data associated with sample points along each branch in the model, and/or aggregated for the whole branch and/or for extended portions thereof. Property data includes, for example: location, orientation, cross-section, radius and/or diameter of vessels. In some embodiments, the tree model comprises flow characteristics at one or more of the points.

In some embodiments, the tree model comprises geometric data measured along vessel centerlines of a vascular system.

In some embodiments, the vascular system model comprises a 3-D model, for example a 3-D model obtainable from a CT scan, and/or constructed from a set of 2-D angiographic images taken from different angles.

In some embodiments, the vascular system model comprises 1-D modeling of vessel segments along center lines of a set of vessels of a vascular system.

In some embodiments, the tree model of the vascular system, comprises data about segments represented in 1-D which describes segment splitting into two or more segments along a vessel.

In some embodiments the model includes a collection of data along segments of the vessels, including three dimensional data associated with a 1-D collection of points; for example: data about a cross sectional area at each point, data about a 3-D direction of a segment, and/or data about an angle of bifurcation.

In some embodiments, the model of the vascular system is used to calculate a physical model of fluid flow, including physical characteristics such as pressure, flow rate, flow resistance, shear stress, and/or flow velocity.

It is noted that performing calculations for a 1-D collection of points, such as calculations of resistance to fluid flow, is potentially much more efficient than performing such calculations using a full 3-D model which includes all voxels of a vascular system.

Calculation of a Vascular Model

Figure 13:
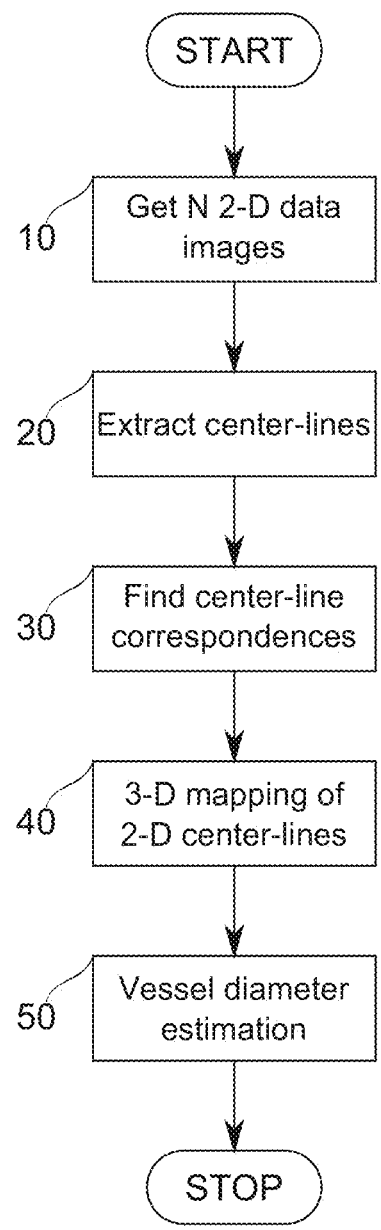
FIG. 13 is a flow chart describing an exemplary overview of stages in vascular model construction, according to some exemplary embodiments of the invention.

Reference is now made to FIG. 13, which is a flow chart describing an exemplary overview of stages in vascular model construction, according to some exemplary embodiments of the invention.

FIG. 13 serves as an overview to an exemplary vascular tree reconstruction method, which is introduced first in overview, then described in more detail hereinbelow.

At block 10, in some embodiments, images are acquired, for example, about 200 images, divided among, for example, 4 imaging devices. In some embodiments, acquired images are obtained by X-ray angiography. A potential advantage of using X-ray angiograms includes the common availability of devices for stereoscopic X-ray angiography in cath labs where diagnosis and interventional procedures are performed, according to the current state of the art. The X-ray angiographic images also have, potentially, a relatively high resolution compared to alternative imaging methods such as CT.

At block 20, in some embodiments, vascular centerlines are extracted. Vascular centerlines have several properties which make them a useful reference for other phases of vascular tree reconstruction. Properties taken advantage of in some embodiments of the current invention optionally include the following:

- Centerlines are features determinable from 2-D images, allowing their use to relate individual images to one another in 3-D.
- Vascular centerlines are, by definition, distributed throughout an imaging region of interest when the target is to reconstruct a 3-D vascular model. Thus, they serve as attractive candidates for reference points within the reconstructed imaging region.
- Vascular centerlines are automatically determinable, without prior human selection, based on image properties which are readily segmented, for example, as described hereinbelow.
- Vascular centerlines are extended features which preserve sufficient similarity among images, even images taken from different views, that their homologies are readily identifiable, for example in the 2-D images themselves, and/or by back-projection along rays into a 3-D space, where ray intersections (and/or intersections among dilated volumes based on back-projected rays) identify homologous targets found in different image projections.
- Spatial ordering of samples along centerlines is conserved among images even though the centerlines themselves are distorted due to viewing angle and/or motion artifacts. This, for example, further facilitates comparisons useful for 3-D reconstruction.
- Centerlines comprise a convenient frame of reference for organizing and/or analyzing features related to position along a blood vessel. For example, using distance along the centerline as a reference, morphological features such as diameter, and/or functional features such as flow resistance, can be expressed as functions in a simplified, 1-D space.
- Intersections of centerlines provide a convenient way to describe vascular branch points, and/or divide a vascular tree into distinct segments which are optionally treated separately from one another, and/or further simplified, for example, for purposes of the functional analysis of flow properties.

Additionally or alternatively, in some embodiments, another type of image feature is identified. Optionally, an image feature is, for example, a furcation of a vessel, or a location of minimal radius (a locally reduced radius compared to surrounding vascular regions) in a stenosed vessel. Optionally, an image feature is any configuration of image pixels having a pattern of intensities generally lacking in self-identity (below a predetermined threshold of self-identity, for example, always above a threshold of intensity difference, or always within a criterion for statistical insignificance of self-identity) over translation in any direction, for example, a corner-like bend or furcation.

At block 30, in some embodiments, correspondences between extracted vascular centerlines in individual 2-D images are found. These correspondences more generally show the relationship between the 2-D images. Additionally or alternatively, another feature commonly identifiable in a plurality of 2-D images is a basis for the finding of correspondences. It should be noted that such correspondences, in general, are not uniquely revealed by transformations determined a priori from calibration information relating to the imaging system and/or patient. A potential advantage of using centerlines for finding correspondences is that the very features of greatest interest in the vascular images (the blood vessels themselves) are the basis of the determination.

In some embodiments of the present invention, a surface corresponding to a shape of the heart of the subject is defined, for example by using the pattern of cardiac blood vessels to determine the projection of the heart surface into different 2-D image planes, and calculating a shell volume therefrom. Optionally, this surface is used as a constraint for the detection of the corresponding image features. In some embodiments, other sources of image data constraints and/or additional information are used in the course of reconstructing a vascular tree. For example, one or more knowledge-based (atlas-based) constraints can be applied, for example, by restricting recognized vascular positions to those which fall within a range of expected vascular positions and/or branch configurations. Also for example, temporal information is available in some embodiments of the invention based on the filling times of positions along the vascular tree. Filling time, in some embodiments, is used for determination and/or constraining of, for example, relative vascular position (position along the vascular tree extent). Filling time is also used, in some embodiments, to help establish homologies among vascular features in different 2-D images (same filling time should be seen in all image vantage points of homologous locations). Additionally or alternatively, filling time is used in some embodiments of the invention to constrain vascular topology.

At block 40, in some embodiments, vascular centerlines are mapped to a 3-D coordinate system. In some embodiments, mapping comprises identifying pairs of homologous centerline positions in different 2-D images which best fulfill a set of optimization criteria, for example, consistency with the constraints of epipolar geometry, and/or consistency with vascular points with 3-D positions previously determined.

At block 50, in some embodiments, blood vessel diameter is estimated. In some embodiments, vascular diameter is calculated across sample points of a selected 2-D projection, and extrapolated to the whole circumference of the blood vessel. In some embodiments, diameters across a plurality of projection angles are determined. In some embodiments, the projected view is selected from a single acquired image, optionally an image where the vessel is seen at its longest, and/or visible free of crossings. Optionally, the projected view is synthesized from two or more 2-D images.

Applications of a Vascular Tree

The computational procedure of the present embodiments potentially requires reduced computation, relative to conventional techniques which employ computational fluid dynamics simulation and analysis. It is recognized that computational fluid dynamics require substantial computation power and/or time. For example, several days of CPU time are required when fluid dynamics simulation is executed on a standard PC. While this time can be somewhat reduced using a super-computer applying parallel processing, such a computation platform is generally unavailable for such a dedicated use in medical facilities. The computational procedure of the present embodiments is not based on fluid dynamic simulations and can therefore be implemented on a computing platform based on common, off-the-shelf components and configured, for example, as a standard PC, without the need for a super-computer.

The present inventors found that a tree model according to some embodiments of the present invention can be provided within less than 60 minutes or less than 50 minutes or less than 40 minutes or less than 30 minutes or less than 20 minutes, or less than 5 minutes, or less than 2 minutes from the time at which the 2-D images are received by the computer. The time is potentially dependent on available computational resources, but the inventors have found that common off-the-shelf computational hardware (available, for example, with an aggregate computational power in the range of about 8-12 teraflops) is sufficient to reach a run time of 2-5 minutes.

This allows some present embodiments of the invention to efficiently combine between the computation and treatment, wherein the tree model is optionally produced while the subject is immobilized on a treatment surface (e.g., a bed) for the purpose of catheterization. In some embodiments of the present invention, the tree model is produced while the subject has a catheter in his or her vasculature. In some embodiments of the present invention the vasculature has at least one catheter other than an angiographic catheter, (for example, a cardiac catheter or an intracranial catheter), wherein the images are processed and the tree is produced while the catheter is in the vasculature.

Use of a calculated vascular tree is envisioned in the context of further processing and/or decision making in a clinical setting. A potential advantage of a method and/or system for rapid determination of a vascular tree is its usefulness in "real time" applications which allow automatically assisted diagnostic and/or treatment decisions to be made while an imaged patient remains immediately available—perhaps still on the catheterization table—for a further procedure.

Examples of such real time applications include vascular flow determination, and/or vascular state scoring.

FFR

In some embodiments of the present invention the model calculated from the original imaging data is treated as a "stenotic model", so-called because it potentially reflects locations of stenosis in the patients vascular (cardiovascular) system. In some embodiments, this stenotic model is used for calculating an index indicative of vascular function. The index can also be indicative of the need for revascularization. A representative example of an index suitable for the present embodiments includes, without limitation, FFR.

In some embodiments, the index is calculated based on a volume or other vascular parameter of a crown in the stenotic model and on a contribution of a stenosed vessel to the resistance to blood flow in the crown. In some embodiments, the FFR index is calculated as a ratio of flow resistance of a stenosed vessel in a vascular model which includes the stenosed vessel to flow resistance of an inflated version of the same vessel in a similar vascular model where the stenosed vessel was mathematically inflated.

In some embodiments, the index is calculated as a ratio of flow resistance of a stenosed vessel in a vascular model to flow resistance of a neighboring similar healthy vessel in the vascular model. In some embodiments, the ratio is multiplied by a constant which accounts for different geometries of the stenosed vessel and the neighboring vessel, as described below in the section titled "Producing a model of physical characteristics of a vascular system".

In some embodiments, a first tree model of a vascular system is produced, based on actual patient measurements, optionally containing a stenosis in one or more locations of the patient's vessels, and a second tree model of the patient's vascular system is produced, optionally changed so that at least one of the stenosis locations is modeled as after revascularization, and an index indicative of the need for revascularization is produced, based on comparing physical characteristics of the first model and the second model.

In some embodiments, actual pressure and/or flow measurements are used to calculate the physical characteristics in the model(s) and/or the above-mentioned index.

In some embodiments, no actual pressure and/or flow measurements are used to calculate the physical characteristics in the model(s) and/or the above-mentioned index.

It is noted that resolution of angiographic images is typically higher than resolution typically obtained by 3-D techniques such a CT. A model constructed from the higher resolution angiographic images, according to some embodiments, can be inherently higher resolution, and provide greater geometric accuracy, and/or use of geometric properties of smaller vessels than CT images, and/or calculations using branching vessels distal to a stenosis for more generations, or bifurcations, downstream from the stenosis than CT images.

Vascular State Scoring

In some embodiments of the invention, automated determination of parameters based on vascular images is used to calculate a vascular disease score. In some embodiments, the imaged blood vessels are cardiac blood vessels.

In some embodiments of the invention, a cardiac disease score is calculated according to the SYNTAX Score calculation method. In some embodiments, a cardiac disease score is calculated by a SYNTAX Score alternative, derivative and/or successor vascular state scoring tool (VSST). Alternative VSST approaches potentially include, for example, a "Functional SYNTAX Score" (integrating physiological measurements—for example, vascular flow capacity, vascular elasticity, vascular autoregulatory capacity, and/or another measure of vascular function—with a SYNTAX Score-like tool), or a "Clinical SYNTAX Score" (integrating clinical variables—for example, patient history, and/or systemic and/or organ-specific test results—with a SYNTAX Score-like tool). Examples also include the AHA classification of the coronary tree segments modified for the ARTS study, the Leaman score, the ACC/AHA lesions classification system, the total occlusion classification system, and/or the Duke and ICPS classification systems for bifurcation lesions.

In some embodiments, two-dimensional images from an angiographic procedure are converted into a three-dimensional image, and lesions within the vessel are identified and entered as VSST parameters to arrive at a quick, objective SYNTAX score during the procedure. In some embodiments, VSST parameters are determined directly from two-dimensional images. Thus, for example, a 2-D image having a determined spatial relationship to a 3-D vascular model (and optionally thereby to vascular segments identified therein) is analyzed for vascular geometry characteristics which are then linked to positions in the vascular model (and optionally identified vascular segments therein).

In some embodiments of the present invention, automatically determined values are provided as parameters to a VSST such as SYNTAX Score in real-time during a catheterization procedure, or following imaging.

Potentially, a reduced time of VSST calculation provides an advantage by allowing a patient to be kept catheterized for a possible PCI (Percutaneous Coronary Intervention) treatment while waiting for a shorter period, and/or by reducing the need for recatheterization of a patient who has been temporarily released from a procedure room pending a treatment decision. Potentially, a reduced time and/or effort of scoring leads to increased use of a VSST such as SYNTAX Score as a tool for clinical decision-making.

Producing a geometric model of a vascular system

Image Acquisition

Figure 14:
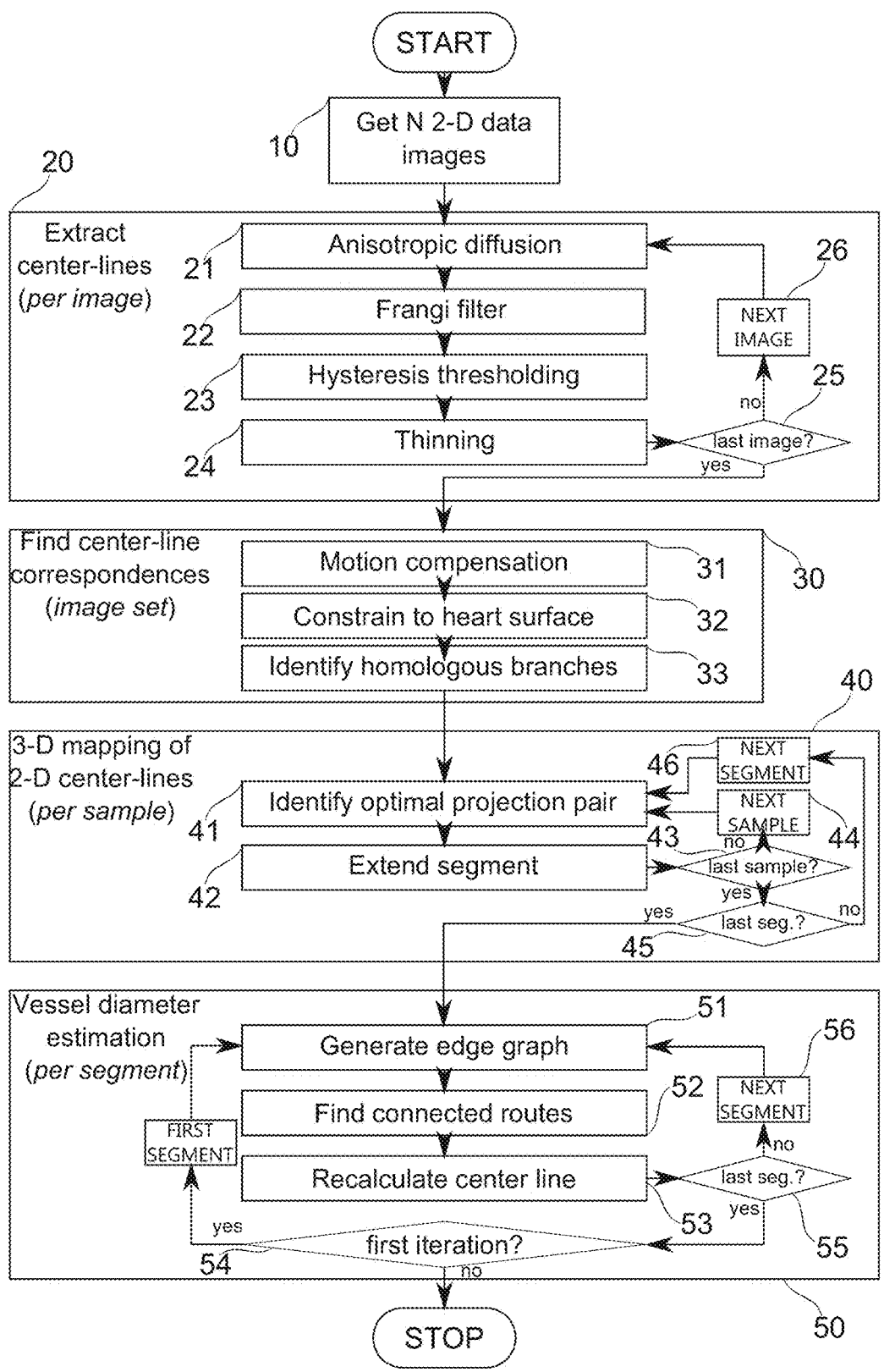
FIG. 14 is a flow chart describing an exemplary overview of details of stages in vascular model construction, according to some exemplary embodiments of the invention.

Reference is now made to FIG. 14, which is a flow chart describing an exemplary overview of details of stages in vascular model construction, according to some exemplary embodiments of the invention. Detail is also described in additional figures referenced in the course of stepping through the blocks of FIG. 14 hereinbelow.

At block 10, a plurality of 2-D data images are acquired. In some embodiments of the invention, data images are simultaneously acquired from a plurality of vantage points, for example, 2, 3, 4 or more imaging vantage points (cameras). In some embodiments, images are acquired at a frame rate of, for example, 15 Hz, 30 Hz, or another lesser, greater, or intermediate frame rate. In some embodiments, the number of frames acquired per imaging vantage point is about 50 frames (200 frames total for 4 imaging vantage points). In some embodiments, the number of frames per imaging vantage point is, for example, 10, 20, 40, 50, 60, 100, or another larger, smaller, or intermediate number. In some embodiments of the invention, the number of heartbeat cycles comprised in an imaging period is about 3-4 heartbeat cycles. In some embodiments, the number of cardiac cycles is, for example, 3-4, 3-5, 4-6, 5-10, or another range of heartbeat cycles having the same, lesser, greater, or intermediate range boundaries.

Reference is now made to FIG. 1, which depicts an original image 110 and a Frangi-filter processed image 120, processed according to some exemplary embodiments of the invention.

The original image 110 depicts a typical angiogram 2-D image.

It should be noted that when using two or more 2-D projections of a subject's vessels, for example heart vessels, it is a potential advantage for two or more 2-D projections be taken at the same time, or at least at a same phase during a heart beat cycle, so that the 2-D projections be of a same vessel shape.

Deviations between the 2-D projections might arise from cardiac, and/or respiratory and/or patient motions between the 2-D projection frames.

In some embodiments, for reduction deviations that might arise from lack of cardiac phase synchronization, an ECG output is used to choose a same cardiac phase in the 2-D projections frames.

In some embodiments, for reduction of deviations that might arise from lack of cardiac phase synchronization, an ECG output, or another heart/pulse synchronization means, such as an optical pulse monitor, is used to choose a same cardiac phase in the 2-D projections frames. Optionally, a heart synchronization output is recorded with a time scale, and a corresponding time scale is used to record when images of the vascular system are captured. In some embodiments of the invention, time of acquisition relative to a cycle of physiological movements is used to determine candidates for mutual registration. For example, image registration is optionally carried out using image data sets which comprise images taken at nearby phases of the heartbeat cycle. In some embodiments, registration is carried out multiple times across different sets of phase-adjacent data sets, so that registered landmarks are iteratively transformed in position to a common 3-D coordinate system.

In some embodiments, 2-D projection frames are selected to be at an end of the diastole phase of the cardiac cycle. In some embodiments, the temporal and/or phase order in which 2-D projection frames are acquired is used to perform registrations among images taken during adjacent movement cycle phases. In some embodiments, images registered from a first phase to a second phase are then re-registered into a third and/or further phase, such that images take at widely separated heartbeat cycle phases can be registered to one another.

In some embodiments, the heart is imaged under influence of intravenous adenosine, which potentially exaggerates a difference between normal and abnormal segments. Optionally imaging with and without adenosine potentially allows determination of the (vascular expanding) effects of adenosine itself, which in turn potentially provides information about vascular compliance and/or autoregulatory state.

Centerline Extraction

Figure 15:
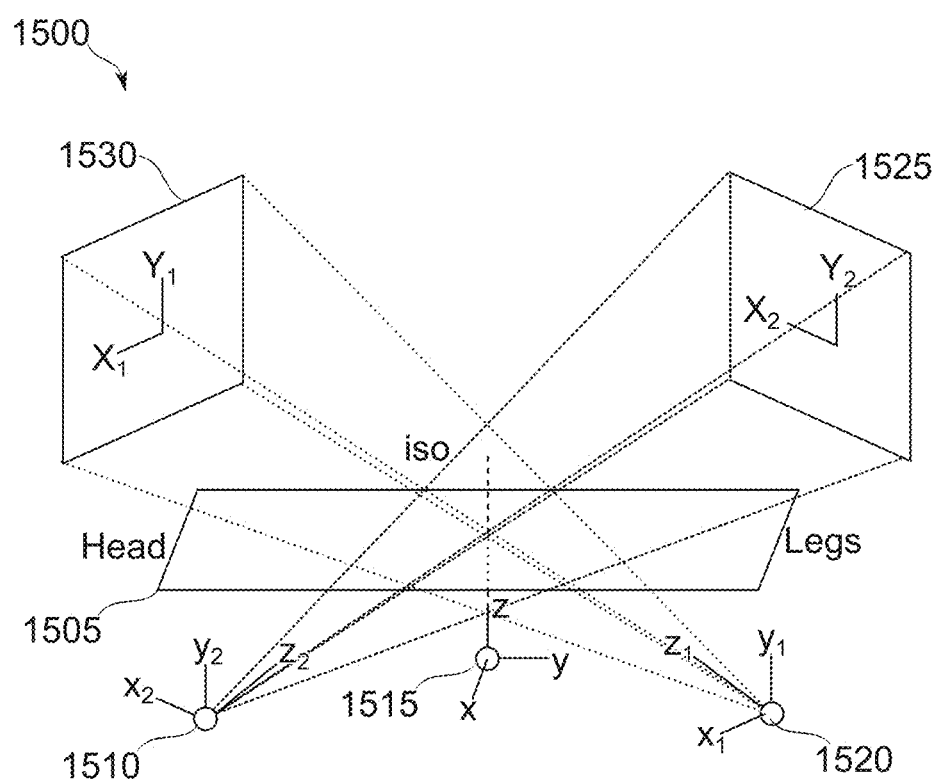
FIG. 15 depicts a schematic of an exemplary arrangement of imaging coordinates for an imaging system, according to some exemplary embodiments of the invention.

Reference is now made to FIG. 15, which depicts a schematic of an exemplary arrangement 1500 of imaging coordinates for an imaging system, according to some exemplary embodiments of the invention.

Several different spatial relationships of an imaging arrangement are used in determining the 3-D relationship of image data in a set of 2-D images.

In some embodiments, the image coordinate systems 1510, 1520 and associated imaging planes 1525, 1530 describe how images taken of the same subject at different positions relate to one another, information which is used to reconstruct 3-D information about the subject. In some embodiments of the invention, these coordinates reflect the axes of the C-arm rotations of an angiogram imaging device. In some embodiments, the coordinate plane 1515 of the subject (for example, lying on bed 1505) also used as part of a 3-D reconstruction.

Although this system configuration information is typically documented in a DICOM (image) file and/or elsewhere, it is not guaranteed to reflect the real position and orientation of the system components with sufficient accuracy and/or precision for useful reconstruction of a coronary artery tree. In particular, the bed axes are potentially misaligned with the room coordinate system, the axes of the C-arm rotations potentially do not intersect at the iso-center and/or are non-orthogonal, and/or the detector axes are potentially not aligned in plane.

At block 20—returning to FIG. 14—centerlines of a vascular tree are extracted from the acquired 2-D images. In some embodiments of the invention, image filtering by anisotropic diffusion 21 comprises a portion of the processing operations which precede centerline extraction. Anisotropic diffusion of 2d gray-scale images reduces image noise while preserving region edges—smoothing along the image edges, and removing gaps due to noise. In some embodiments, the basis of the method used is similar to that introduced by Weickert in "A Scheme for Coherence-Enhancing Diffusion Filtering with Optimized Rotation Invariance" and/or "Anisotropic Diffusion in Image Processing" (Thesis 1996).

Figure 16:
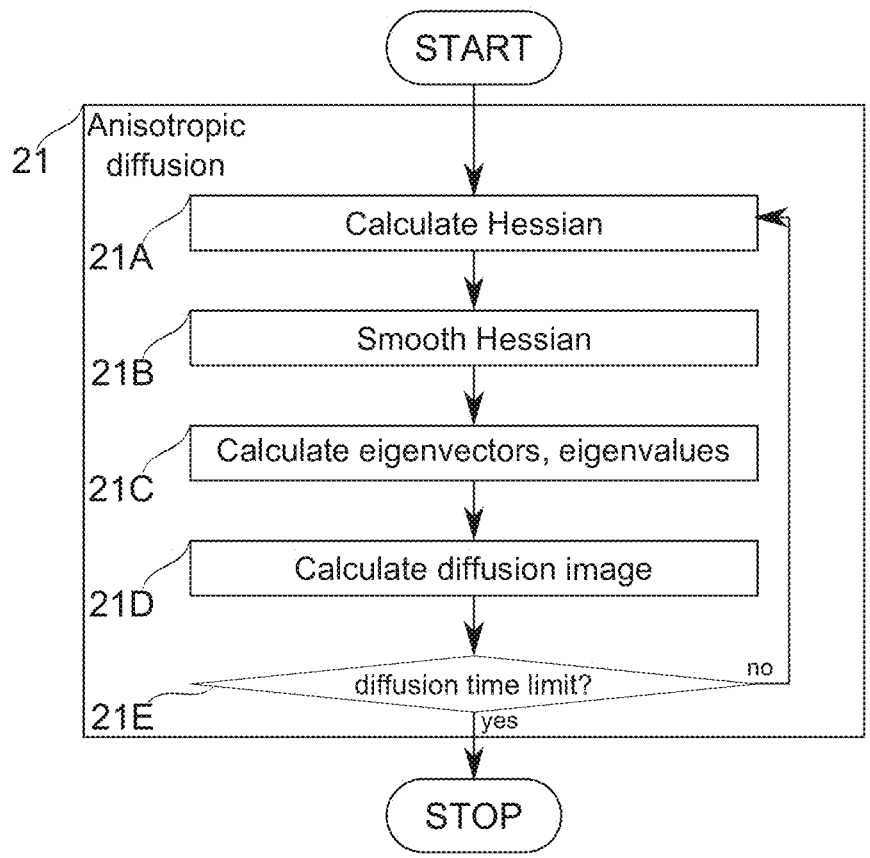
FIG. 16 is a simplified flowchart of processing operations comprised in anisotropic diffusion, according to some exemplary embodiments of the invention.

Reference is now made to FIG. 16, which is a simplified flowchart of processing operations comprised in anisotropic diffusion, according to some exemplary embodiments of the invention.

Operations are described for a single image, for some embodiments of the invention. At block 21A, the Hessian transform is calculated from every pixel of the Gaussian smoothed input image (the Hessian is related to the $2^{nd}$ derivative of the image data, and is a form of edge detection). At block 21B, the Hessian-transformed image is smoothed, for example, by a Gaussian filter. At block 21C, the eigenvectors and eigenvalues of the smoothed Hessian-transformed image are calculated. The resulting eigenvalues are in general larger where the original image comprises edges, while eigenvectors corresponding to large eigenvalues describe the direction in which the edge runs. Additionally or alternatively, another edge detection method, such as are known in the art, is used.

At block 21D, in some embodiments of the invention, a diffusion image is calculated. A finite difference scheme is used to perform the diffusion, using, in some embodiments, the eigenvectors as diffusion tensor directions.

At block 21E, in some embodiments, a determination is made if a diffusion time limit (for example, a certain number of iterations which lead to a desired level of image filtering) has been reached. If no, the flowchart returns to block 21A and continues. If yes, the flowchart ends—and flow continues within a higher-level flowchart, for example, that of FIG. 14.

At block 22, in some embodiments of the invention, a Frangi filter is applied, based on the Hessian eigenvectors, which comprises computation of the likeliness of an image region to be within a vessel. Frangi filtering is described, for example, by Frangi, et al. "Multiscale vessel enhancement filtering", Medical Image Computing and Computer-Assisted Intervention—MICCA '98. By way of a non-limiting example, the Frangi-filter processed image 120 (FIG. 1) depicts the original image 110 after image enhancement using a Frangi filter. In some embodiments, another filter is used, for example a threshold filter, or a hysteresis threshold filter, whereby pixels of an image are identified as belonging within an image region of a vessel.

At block 23, in some embodiments of the invention, the image is processed to generate a black-white figure representing vascular locations in the angiographic projection image. In some embodiments, a hysteresis threshold filter is performed on the Frangi filter output with high and low thresholds. First the algorithm detects the pixels which are (for example, with reference to image 120) brighter than the higher threshold; these are labeled as vascular pixels. In the second step, the algorithm also labels as vascular those pixels with brightness higher than the low threshold, and also connected across the image to pixels already labeled as vascular pixels.

A potential disadvantage of the Frangi-filter is the presence of bulb-like shapes at vascular junctions which interfere with accurate detection. In some embodiments, a region-grow algorithm is used to extract these regions, as an improvement on hysteresis thresholding alone. The thresholded black-white image and the gray-scale image obtained by anisotropic diffusion comprise inputs to this algorithm.

Square dilation is performed on the black-white image, and the result is subtracted from the original black-white image. The subtraction image comprises a one pixel-wide frame along which the growth of the region of vascular-labeled pixels is then examined. The values (brightnesses) of the pixels in this frame are compared locally to those of existing vascular pixels, and to the surrounding pixels. A high relative result leads to expansion. Optionally, the process repeats until no more vascular pixels are found.

At block 24, in some embodiments, a thinning convolution is applied to thin the black-white image segments down to lines which represent the vascular centerlines.

In some embodiments, blocks 21-24 are performed per image (for example, sequentially, interleaved, and/or in parallel). At block 25, assuming sequential processing, if there are more images to process, the next image is selected at block 26, and processing continues again with block 21.

Figure 2:
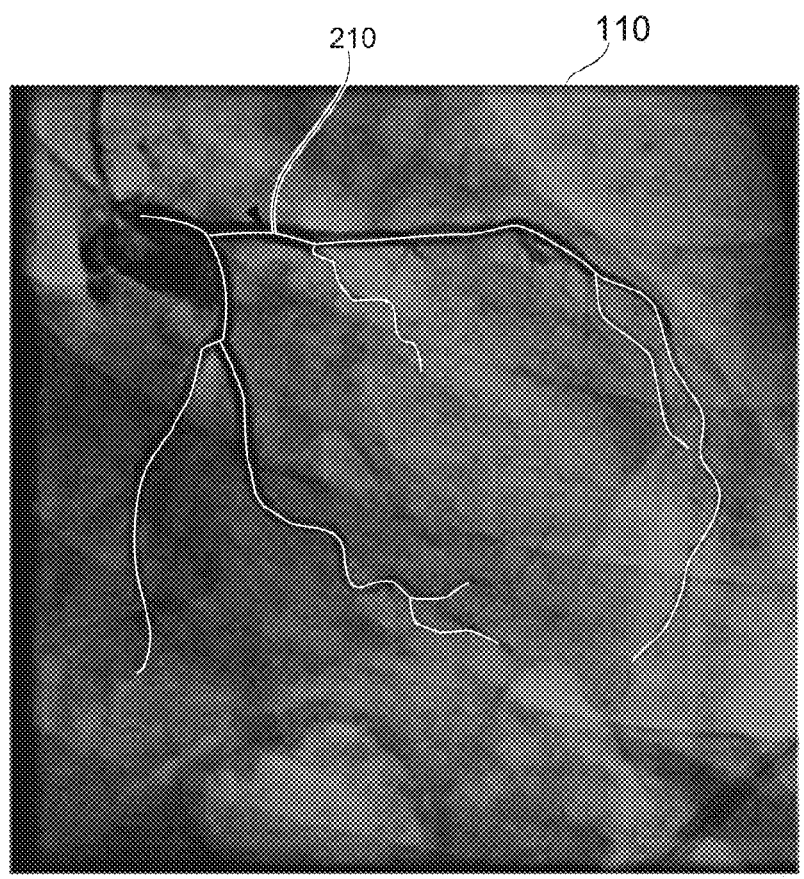
FIG. 2 depicts a light-colored center line overlaid on top of the original image of FIG. 1, according to some exemplary embodiments of the invention.

Otherwise, centerline extraction, in some embodiments of the invention, is complete. Reference is now made to FIG. 2, which depicts a 2-D tree 218 comprising light-colored vascular centerlines overlaid on top of the original image 110 of FIG. 1, according to an example embodiment of the invention.

Motion compensation

In some embodiments of the invention, processing to find centerline correspondences continues (FIG. 14) at block 30. A goal of finding centerline correspondences is to find correspondences between different 2-D images (points that image the same region of space, though potentially from different angles), such that a 3-D reconstruction of the target vasculature can be made.

At block 31, operations for motion compensation and/or imaging position artifact compensation are performed.

With ideal calibration information (each image plane perfectly identified relative to a common coordinate axis, for example), and no artifacts due to motion or other positioning errors, back-projecting a large enough number of 2-D images to 3-D space potentially yields intersecting rays (for example, rays $S_1$-$P_1$ and $S_2$-$P_2$ of FIG. 20B) uniquely defining the extents of the vascular centerline in 3-D. In practice, deviations among images originate, for example, from breathing, voluntary movements of the patient, and inaccurate and/or imprecise phase-locking of imaging exposures to the cardiac cycle. Overcoming this issue in a computationally inexpensive way is a goal, in some embodiments, of operations for motion compensation. Calibration errors potentially introduce other forms of image position artifacts.

In some embodiments of the invention, the procedure compensates for breath and/or other patient movement. Optionally, this comprises iteratively repeating the detection of the corresponding image features, each time for a different subset of angiographic images, and updating the image correction parameters responsively to the repeated detection.

Figure 17A:
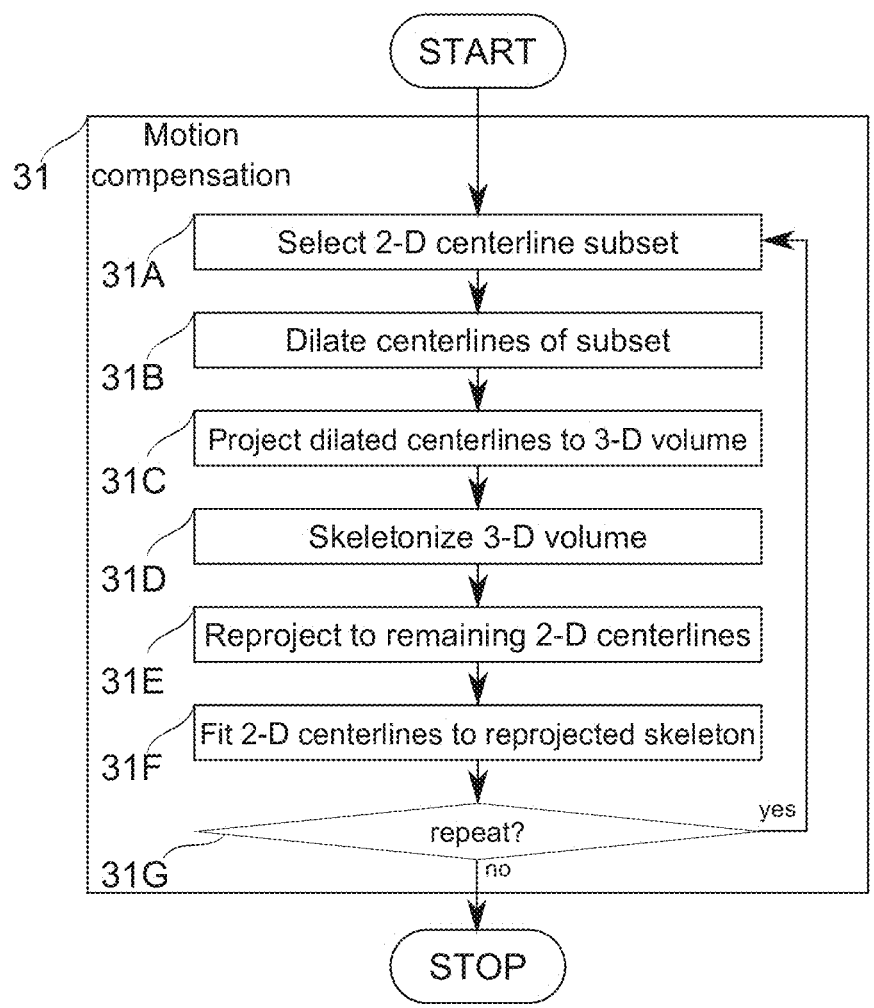
FIG. 17A is a simplified flowchart of processing operations comprised in motion compensation, according to some exemplary embodiments of the invention.

Reference is now made to FIG. 17A, which is a simplified flowchart of processing operations comprised in motion compensation, according to some exemplary embodiments of the invention.

At block 31A, in some embodiments of the invention, a subset of images (comprising a plurality) with identified 2-D centerlines is selected for processing. Centerlines are optionally dilated at block 31B, and a centerline projection back into 3-D performed at block 31C, based on the current best-known projection parameters for each image (initially these are, for example, the parameters expected based on the known calibrations of the imaging device). The resulting projected volume is skeletonized, in some embodiments, to form a "consensus centerline" at block 31D. At block 31E, the consensus centerline is projected back into the coordinate systems of 2-D images comprising those which were not used in forming the consensus centerline. At block 31F, an optimization procedure adjusts projection parameters for the 3-D centerline into each 2-D image to fit more closely centerlines found within the image itself. This adjustment is used to adjust the projection parameters associated with each image. At 31G, in some embodiments, a determination is made whether or not to repeat the procedure for a different image subset, for improvement of the overall quality of the projection fits. The determination to repeat is based, for example, on a predetermined number of iterations, a metric measuring quality of fit (such as a mean distance between closest points in centerline projections), or another criterion. If yes, the flowchart returns to block 31A and continues. If no, the flowchart ends—and flow continues within a higher-level ordering of operations, for example, that of FIG. 14.

It was found by the present inventors that such an iterative process significantly can reduce one or more of the effects of breath, patient movements, and heart phase difference.

Figure 17B:
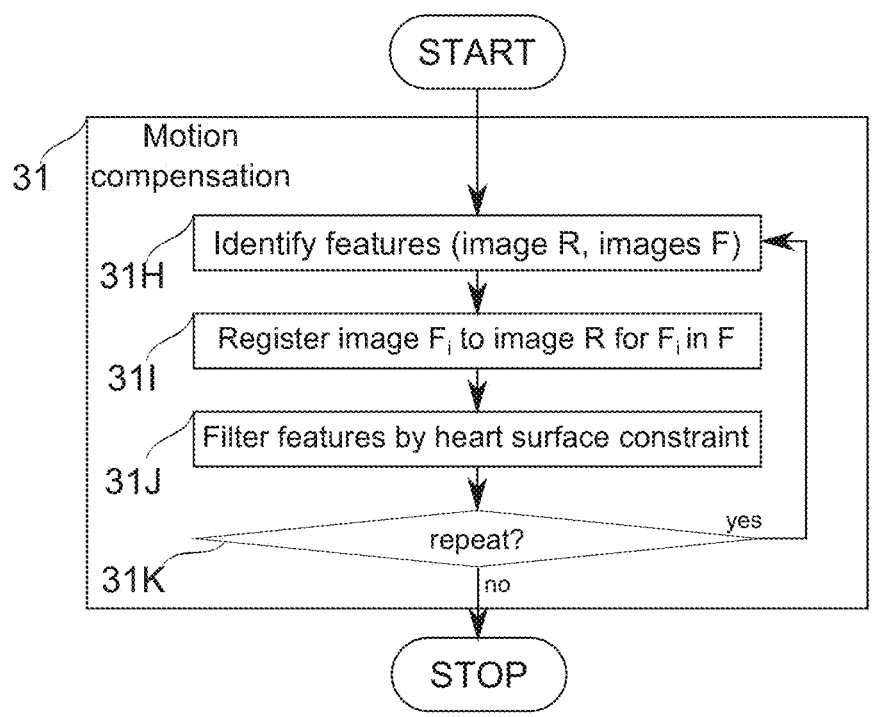
FIG. 17B is a simplified flowchart of processing operations comprised in an alternative or additional method of motion compensation, according to some exemplary embodiments of the invention.

Reference is now made to FIG. 17B, which is a simplified flowchart of processing operations comprised in an alternative or additional method of motion compensation, according to some exemplary embodiments of the invention.

In some embodiments of the invention, at block 31H, features are identified in a reference image R based on any feature detection method known in the art. Such an image feature is, for example, a furcation of a vessel, and origin of the coronary vessel tree, a location of minimal radius in a stenosed vessel, and/or any configuration of image pixels having a pattern of intensities generally lacking in self-identity over translation in any direction—for example, a corner-like bend or furcation. Similar features (putatively homologous to those of the reference image) are identified in remaining images F.

In some embodiments of the invention, at block 31I, images in F are then registered to image R. For example, the best-known projection parameters of image F are used to transform into the best-known projection plane of image R, and then optimized to obtain an improved fit, for example using epipolar geometry to calculate parameters of shift, rotation, and/or scaling. Optionally, registration comprises application of a geometric distortion function. The distortion function is, for example, a first, second, or other-order function of the two image plane coordinates. Additionally or alternatively, the distortion function comprises parameters describing the adjustment of nodal points defined within the image coordinate planes to bring them into registration.

In some embodiments, the best-known projection parameters are the same, and only the geometric distortion function is applied.

In some embodiments, operations at block 31I comprise image correction parameters calculation based on identified corresponding image features. Correction parameters typically describe, for example, translation and/or rotation of the system of coordinates of a particular image. Based on the calculated parameters, the angiographic images are registered to provide to provide mutual geometrically correspondence thereamongst. In some embodiments of the invention, several images are registered relative to one of the images. For example, when corresponding image features are identified in N images (e.g., N=2, 3, 4 or more) one of the images can be selected as a reference, while the registration is applied for the remaining N−1 angiographic images such that each of those remaining images geometrically corresponds to the single angiographic image that was selected as a reference. In some embodiments, another registration scenario, for example, pairwise registration, is performed.

At block 31J, in some embodiments, candidate feature positions of identified features which are expected to be comprised within a shell-like volume near the heart surface (in particular, vascular features) are filtered based on whether or not they do indeed fit within such a volume. Calculation of this shell-like volume is described, for example, in relation to FIGS. 18A-18C.

At block 31K, in some embodiments, a determination is made whether or not to repeat the procedure for a different image subset, for improvement of the overall quality of the projection fits. The determination to repeat is made, for example, as described for block 31G. If yes, the flowchart returns to block 31H and continues. If no, the flowchart ends—and flow continues within a higher-level ordering of operations, for example, that of FIG. 14.

Heart Surface Constraint

Figure 18A:
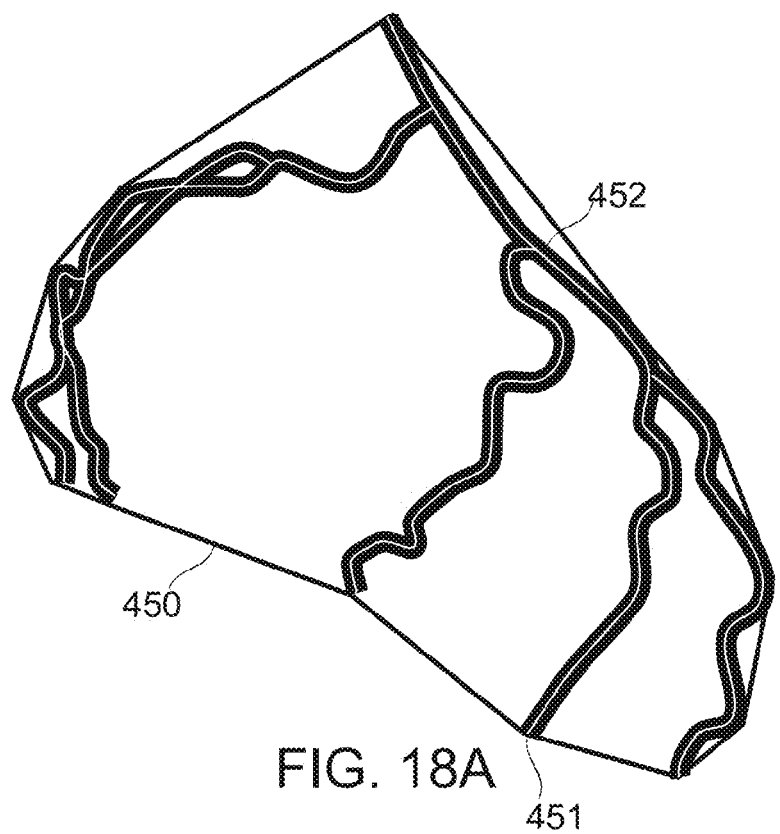
FIGS. 18A-18B illustrate aspects of the calculation of a "cardiac shell" constraint for discarding bad ray intersections from calculated correspondences among images, according to some exemplary embodiments of the invention.
Figure 18B:
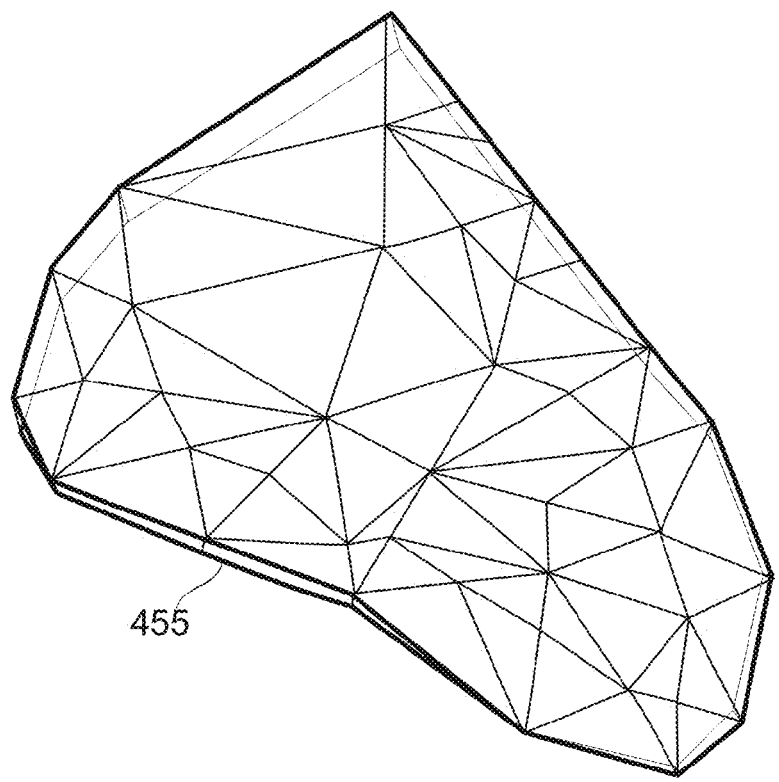

Reference is now made to FIGS. 18A-18B, which illustrate aspects of the calculation of a "cardiac shell" constraint for discarding bad ray intersections from calculated correspondences among images, according to some exemplary embodiments of the invention.

Figure 18C:
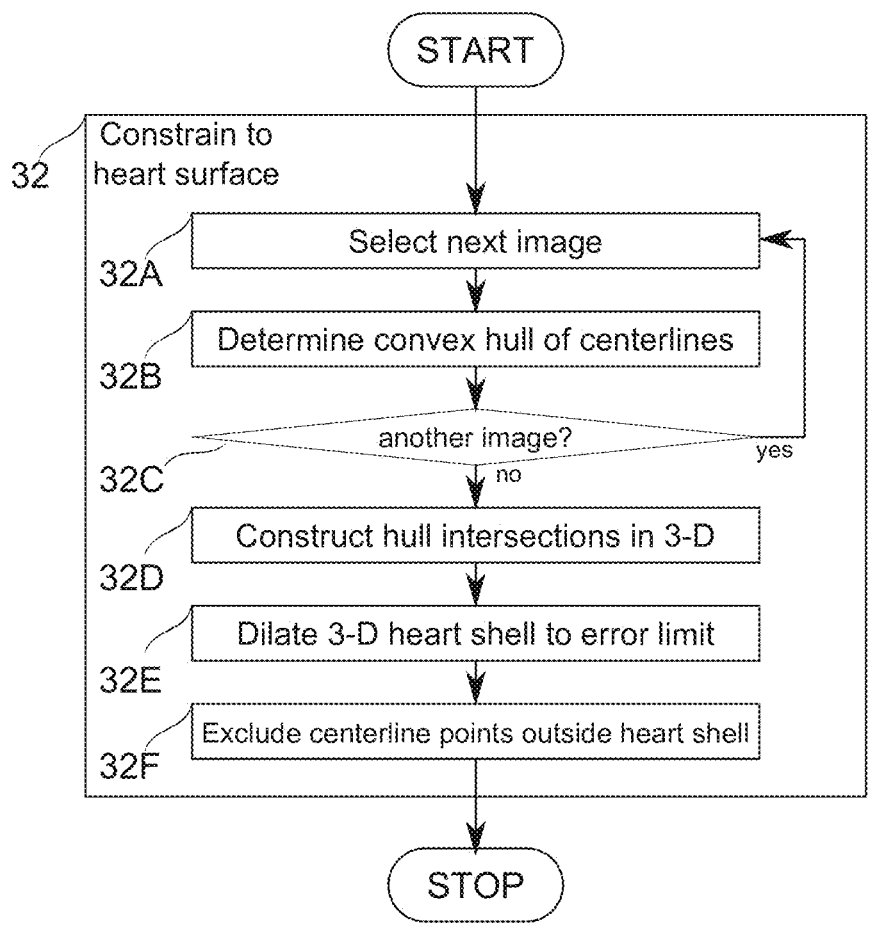
FIG. 18C is a simplified flowchart of processing operations comprised in constraining pixel correspondences to within a volume near the heart surface, according to some exemplary embodiments of the invention.

Also, reference is now made to FIG. 18C, which is a simplified flowchart of processing operations comprised in constraining pixel correspondences to within a volume near the heart surface, according to some exemplary embodiments of the invention.

In some imaging procedures, a "large enough" number of projections is potentially unavailable, such that the error in the determined position of ray intersections potentially prevents convergence to a correct output. At block 32, in some embodiments of the invention, operations to reduce the effect of this source (and/or other sources) of positional error are performed, based on a heart surface constraint.

At block 32A, according to some embodiments of the invention, an image which comprises features expected to be within the projected outline of the heart is selected. In some embodiments, the features are representations of the coronary arteries 452, which course over the heart surface. In some embodiments, previously determined vascular centerlines 451 comprise the identified features. At block 32B, in some embodiments, the convex hull 450 defined by the vascular centerlines 451 is determined. This hull grossly represents the shape of the heart (where it is covered by identified artery centerlines) as projected into the plane of the selected 2-D image. At block 32C, in some embodiments, a determination is made as to whether or not another image should be selected to determine the heart shell projection from a different angle. The number of images for which the convex hull of the heart shape is calculated is at least two, in order allow 3-D localization of the heart shell; optionally more images, and optionally all available images are used for heart shell determination. If another image is to be added, the flowchart continues at block 32A; if no, flow continues to block 32D.

At block 32D, in some embodiments, the 3-D hull position (heart shell) is determined from the various available 2-D hull projections, for example by using the best-known projection parameters for each 2-D image plane, and/or the intersections of the 3-D polyhedra. Such a surface can be defined using any technique known in the art, including, without limitation, polyhedra stitching, based on the descriptions provided herein. At block 32E, in some embodiments, the heart shell is dilated to a volume, the amount of dilation being determined, for example, as corresponding to an error limit, within which "true" vascular regions are expected to fall.

At block 32F, in some embodiments, candidate 3-D positions of vascular centerline points which fall outside the heart shell are excluded. The flowchart of FIG. 18C ends— and flow continues within a higher-level ordering of operations, for example, that of FIG. 14.

Identification of Homologies

Reference is now made to FIGS. 19A-19D, which illustrate identification of homology among vascular branches, according to some exemplary embodiments of the invention.

Figure 19A:
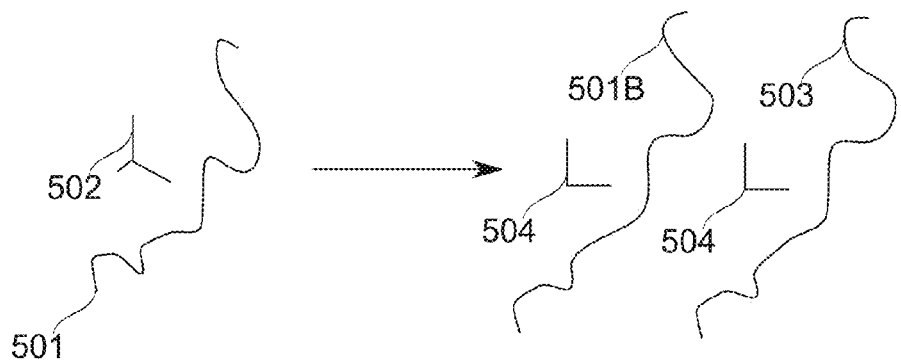
FIGS. 19A-19D illustrate identification of homology among vascular branches, according to some exemplary embodiments of the invention.
Figure 19B:
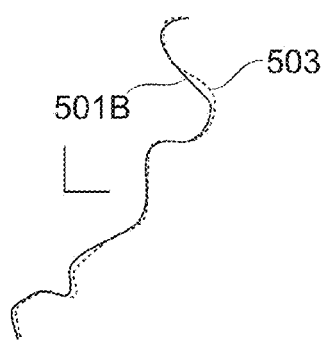
Figure 19C:
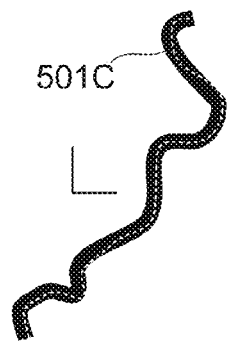
Figure 19D:
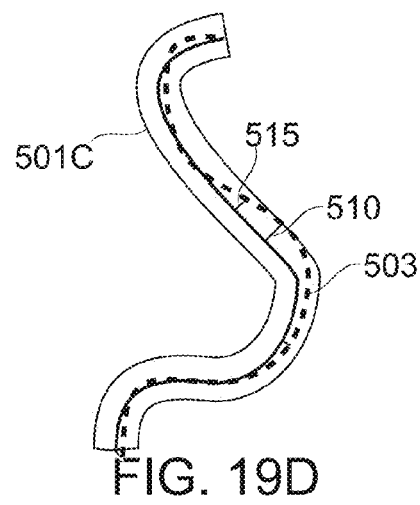
Figure 19E:
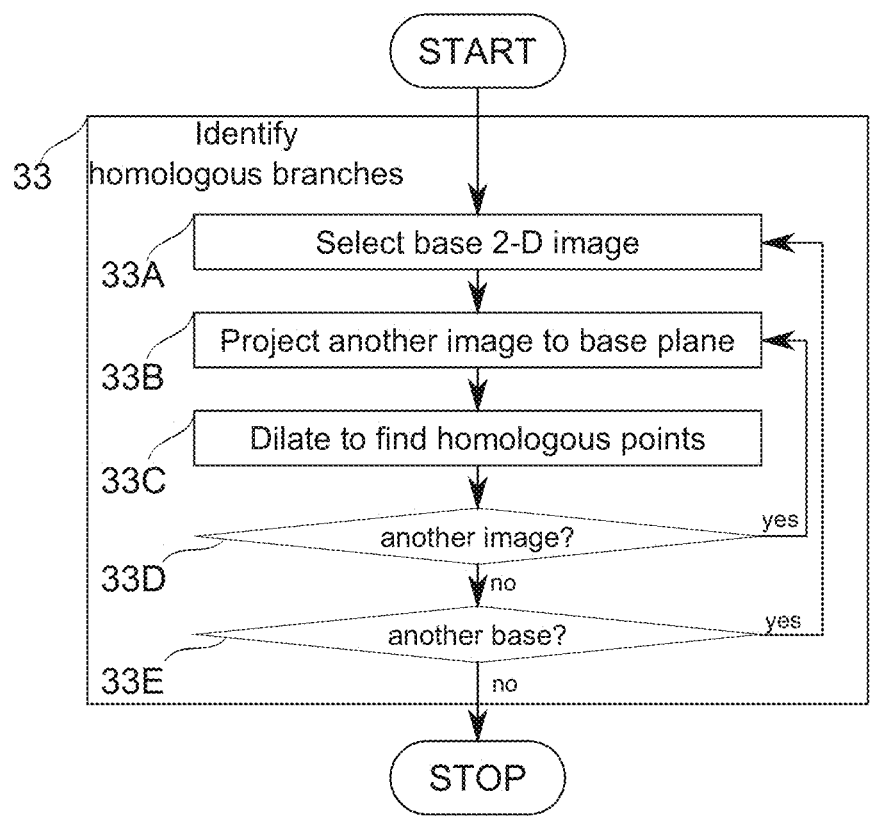
FIG. 19E is a simplified flowchart of processing operations comprised in identifying homologous regions along vascular branches, according to some exemplary embodiments of the invention.

Also, reference is now made to FIG. 19E, which is a simplified flowchart of processing operations comprised in identifying homologous regions along vascular branches, according to some exemplary embodiments of the invention.

At block 33A, in some embodiments, a base 2-D image is selected for homology determination. The initial base selection is optionally arbitrary. At block 33B, in some embodiments, the vascular centerlines in one of the remaining images is projected into the plane of the base image. For example, exemplary vascular centerline 503 of FIG. 19A is from a base image having a base coordinate system 504. Vascular centerline 501, taken from another image having a different coordinate system 502 is shown transformed into coordinate system 504 (translated in one direction for clarity in FIG. 19A) as centerline 501B. In FIG. 19B, the two centerlines are shown overlaid, illustrating their general similarity, and some artifactual differences where they diverge.

At block 33C, in some embodiments, the projected vascular centerline 501B is dynamically dilated 501C, noting where intersections with the base image vascular centerline first occurs, and continuing, for example, until all homologies have been identified. Dynamic dilation comprises, for example, gradual expansion of the centerline, for example by application of a morphological operator to pixel values of the image. In some embodiments, another method, for example, a nearest-neighbor algorithm, is used (additionally or alternatively) to determine correspondences. FIG. 19D shows examples of correspondence between vascular centerline points at either end of minimal distance lines 515 and 510.

At block 33D, in some embodiments, a determination is made as to whether another image is to be selected for dilation to the current base image. If yes, the flowchart continues at block 33B. If no, at block 33E, a determination is made as to whether another base image is to be selected. If yes, the flowchart continues at block 33A. If no, the flowchart ends—and flow continues within a higher-level ordering of operations, for example, that of FIG. 14.

It should be understood that the operations in block 30 (for example, of sub-blocks 31, 32, 33) to find centerline correspondences are operations which perform the function of finding correspondences between the different 2-D images—and more particularly, in some embodiments, between vascular centerlines in the 2-D images—which allow them to be reconstructed into a 3-D model of the vasculature. It should be understood that this function can be performed by variations on the methods described and/or by other methods familiar to one skilled in the art, based on the teachings of the present description. For example, wherever an image A is projected, mapped, or otherwise transformed to the coordinate space of an image B, it is possible in some embodiments for the transformation be reversed (transforming B instead), or for the transformation to be of both images to a common coordinate space. Also for example, features and/or locations which are nearby a feature named in describing an operation (for example, vascular boundaries in relation to vascular centerlines) are usable, in some embodiments, to perform some of the work of finding correspondences. Furthermore, operations which serve entirely to refine a result (including an intermediate result) are optional in some embodiments; additionally or alternatively, other operations to refine a result (including an intermediate result) are potentially determinable by someone skilled in the art, working based on the descriptions herein. These examples of variations are not exhaustive, but are rather indications of the breadth of the methods comprising embodiments of the present invention.

In considering even more generally the results of operations described in connection with blocks 20 and 30: progress toward at least two related but separate goals is calculated, in some embodiments, on the basis of shared intermediate results—the vascular centerlines. A first goal is finding the spatial relationships by which acquired 2-D images are related to a common, 3-D imaging region. While, in principle, a large number of possible reference features are selectable from the 2-D images as a basis of this determination, it is a potential advantage to use the centerlines of the vascular tree as the reference. In particular, determination of the vascular tree within this 3-D space is itself a second goal: thus, in some embodiments, the feature by which images are registered to one another is also the feature which serves as the skeleton of the vascular model itself. This is a potential advantage for speed of calculation, by reducing the need for separate determination of features for image registration, and vascular features as such. It is a potential advantage for the accuracy, precision, and/or consistency of the resulting vascular model, since registration among vascular features the foundation of the transformations of image data from which those same features are to be reconstructed.

3-D Mapping

At block 40, in some embodiments of the invention, 3-D mapping of 2-D centerlines is performed. In some embodiments, at block 41, 3-D mapping begins with identification of optimal projection pairs. Where several different images have been acquired, there are potentially several different (although homologous) projections of each region of a vascular centerline into 3-D space, each based on a different pair of 2-D images.

Figure 20A:
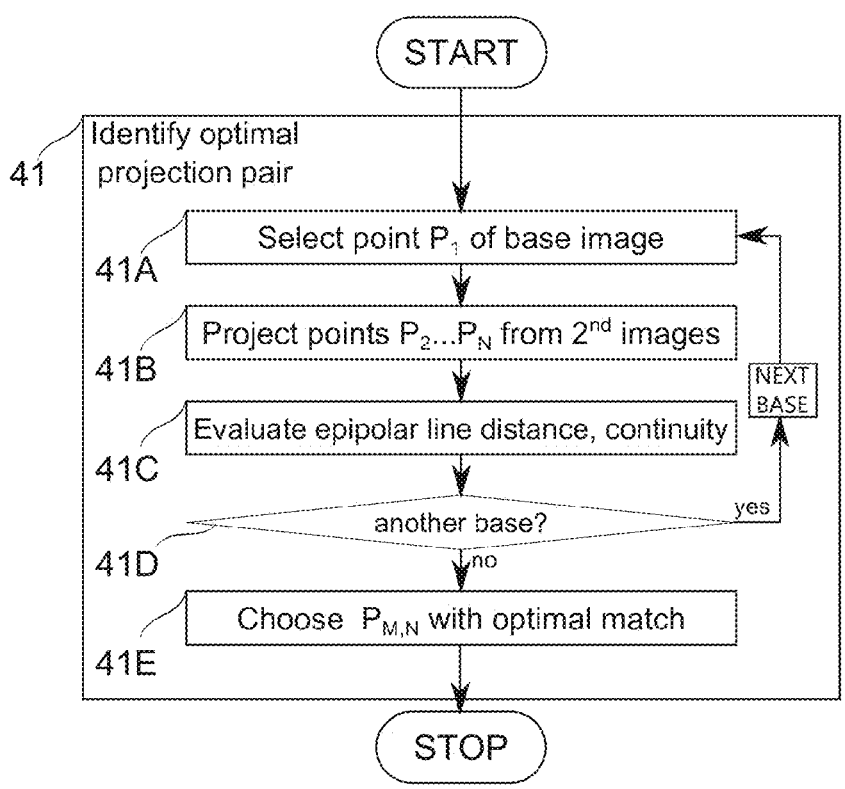
FIG. 20A is a simplified flowchart of processing operations comprised in selecting a projection pair along a vascular centerline, according to some exemplary embodiments of the invention.

Reference is now made to FIG. 20A, which is a simplified flowchart of processing operations comprised in selecting a projection pair along a vascular centerline, according to some exemplary embodiments of the invention. Entering block 41, an initial segment comprising a vascular centerline is chosen, along with an initial homologous group of centerline points along it (for example, a point from an end) in the different 2-D images.

At block 41A, in some embodiments of the invention, a point $P_1$ on a vascular centerline (corresponding to some homologous group of centerline points P) is selected from a first base image. At block 41B, in some embodiments, other points $P_2 \ldots P_N$ are selected from the homologous group P to be paired with $P_1$ to find a position in 3-D space.

Figure 20B:
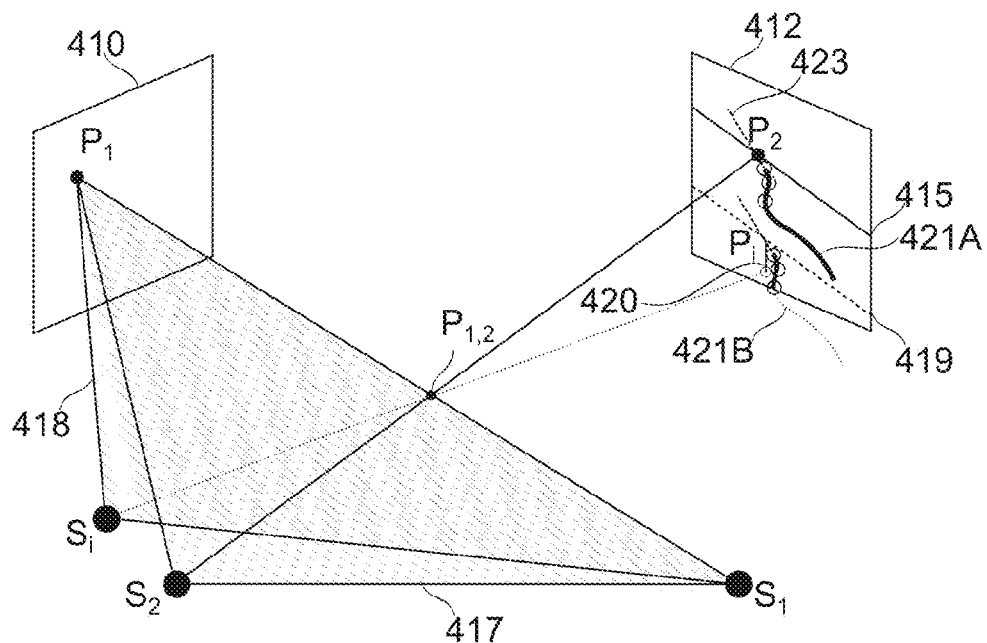
FIG. 20B is a schematic representation of epipolar determination of 3-D target locations from 2-D image locations and their geometrical relationships in space, according to some exemplary embodiments of the invention.

Reference is now made to FIG. 20B, which is a schematic representation of epipolar determination of 3-D target locations from 2-D image locations and their geometrical relationships in space, according to some exemplary embodiments of the invention.

A point $P_1$, associated with image plane 410 is matched to a point $P_2$ to determine a location $P_{1,2}$ in 3-D space, using principles of epipolar geometry. In brief: the ray passing from a source $S_1$ through a target region to point $P_1$ is on a plane 417 which is determined also by rays passing from $S_2$ to intersect it. The continuations of these rays intersect plane 412 along an epipolar line 415.

At block 41C, in some embodiments, points are evaluated for their relative suitability as the optimal available projection pair to extend a vascular centerline in 3-D space.

In some embodiments of the invention, a criterion for the optimal choice of a projection point is a distance of a projected point from its associated epipolar line. Ideally, each point $P_2 \ldots P_N$ lies on the epipolar line corresponding to the epipolar plane defined by $S_2 \ldots S_N$. However, due to imaging position artifacts—for example, those described in relation to calibration and/or motion—there may remain some error, such that a point $P_1$, previously determined to be homologous to $P_1$, lies off of its associated epipolar plane 418, and therefore a distance 420 away from its associated epipolar line 419. Optionally, the projection point closest to its associated epipolar line for a given homology group is scored as most suited as the projection point for extending the vascular centerline.

In some embodiments of the invention, one or more criteria for the optimal choice of a projection point relate to the continuity of extension that a projected point provides from projected points already determined. For example, a set of points along vascular centerline 421A, 421B can be used to determine a current direction of extension 423, and/or expected distance interval to the next extending point in 3-D space. In some embodiments, projection points which more closely match one or more of these, or another geometrical criterion, are scored as correspondingly more suitable choices.

In some embodiments, a plurality of criteria are weighted together, and a choice of an optimal projection pair made based on the weighted result.

At block 41D, it is determined whether a different base point in the homology group should be chosen. If yes, the next base point is chosen, and further projections and evaluations continue from block 41A. If no, the point having the optimal (most suited from among the available choice) score for inclusion in the 3-D vascular centerline is chosen. The flowchart of FIG. 20A ends—and flow continues within a higher-level ordering of operations, for example, that of FIG. 14.

At block 42, in some embodiments, the current vascular segment centerline is extended according to point specified by the identified optimal pair of projections.

Vascular centerline determination continues at 43, in some embodiments, where it is determined whether or not another sample (homology group) should be assessed for the current vascular centerline. If so, operations continue by selection of the next sample at block 44, continuing with re-entering block 41. If not, determination is made at block 45 whether the last vascular segment centerline has been determined. If not, the next segment is selected at 46, and processing continues at the first sample of that segment at block 41. If yes, flow continues, in some embodiments, to vessel diameter estimation at block 50.

Vessel Diameter Estimation

Figure 21:
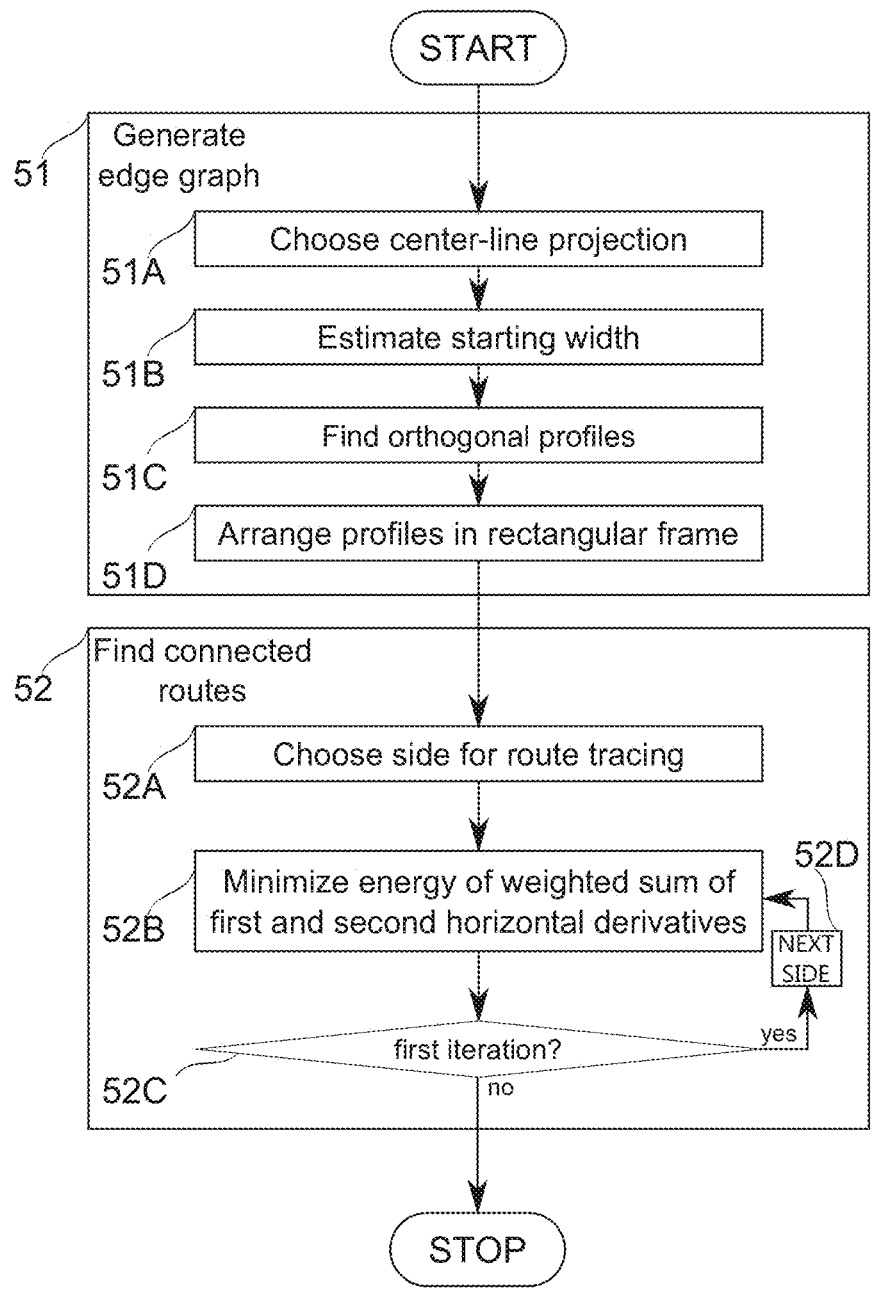
FIG. 21 is a simplified flowchart of processing operations comprised in generating an edge graph, and in finding connected routes along an edge graph, according to some exemplary embodiments of the invention.

Reference is now made to FIG. 21, which is a simplified flowchart of processing operations comprised in generating an edge graph 51, and in finding connected routes along an edge graph 52, according to some exemplary embodiments of the invention.

Entering block 51, in some embodiments, an edge graph is to be determined. At block 51A, in some embodiments, a 2-D centerline projection is chosen which is mapped to locations relative to the locations of intensity values of the 2-D imaging data.

Optionally, the projection chosen is one in which the blood vessel is projected at a maximum length. Optionally, the projection chosen is one in which the blood vessel does not cross another vessel. In some embodiments, projections are chosen according sub-regions of a 2-D centerline of a vascular segment, for example, to have maximum length and/or non-crossing properties within the sub-region. In some embodiments of the invention, images from orthogonal projections (and/or projections having another defined angular relationship) are selected.

At block 51B, in some embodiments, a starting vascular width (a radius, for example) is estimated. The starting width is determined, for example, by generating an orthogonal profile to the center line and choosing the peak of the weighted sum of the first and second derivatives of the image intensity along the profile.

At block 51C, in some embodiments, an orthogonal profile is built for points along the centerline; for example, for points sampled at intervals approximately equivalent to the vascular starting width. The precise choice of interval is not critical: using the radius as the interval is generally appropriate to provide a sufficient resolution for diameter estimation.

At block 51D, in some embodiments, orthogonal profiles for sampled points are assembled in a rectangular frame, somewhat as though the convolutions of the 3-D centerline were straightened, bringing the orthogonal profiles through the centerline into parallel alignment.

Entering block 52, in some embodiments, connected routes along vascular edges are now found. At block 52A, in some embodiments, a first side (vascular edge) is chosen for route tracing. In some embodiments, at block 52B, a route is found along the edge at approximately the distance of the initial radius, for example, by minimizing the energy that corresponds to a weighted sum of the first and second horizontal derivatives, optionally with the aid of an algorithm of the Dijkstra algorithm family. At block 52C, if the second side has not been calculated, the flowchart branches to select the second side at block 52D, and repeat the operation of 52B.

Continuing, in some embodiments, at block 53 of FIG. 14, the centerline is reset to the middle of the two vascular walls just determined At block 55, in some embodiments, a determination is made if this is the last centerline to process. If not, in some embodiments, the next segment is selected at block 56 and processing continues at block 51. If yes, at block 54, in some embodiments, a determination is made if the procedure is to be repeated. If yes, a first segment is selected for a second iteration, and operations continue at block 51. Otherwise, the flowchart of FIG. 14 ends.

Construction of a segment-node representation of a vascular tree

Reference is now made to FIG. 3A, which is an image 305 of a coronary vessel tree model 310, produced according to an example embodiment of the invention.

Reference is now also made to FIG. 3B, which is an image of a coronary vessel tree model 315 of FIG. 3A, with tree branch tags 320 added according to an exemplary embodiment of the invention.

It is noted that the tags 320 are simply one example method for keeping track of branches in a tree model.

In some embodiments of the invention, after reconstruction of a vessel tree model, such as a coronary tree, from angiographic images, the tree model is optionally divided into branches, where a branch is defined as a section of a vessel (along the frame of reference established by the vascular centerline, for example) between bifurcations. The branches are numbered, for example, according to their generation in the tree. Branch points (nodes), in some embodiments of the invention, are determinable from points of the skeletal centerline representation which connect in more than two directions.

In some embodiments of the invention, branch topology comprises division of a vascular tree model into distinct branches along the branch structure. In some embodiments, branch topology comprises recombination of branches, for example, due collateral and/or shunting blood vessels.

Reference is now also made to FIG. 3C, which is a simplified illustration of a tree model 330 of a coronary vessel tree, produced according to an example embodiment of the invention.

For some aspects of the application of a vascular tree model to coronary artery diagnosis and/or functional modeling, it is useful to abstract away some details of spatial position in order to simplify (and, in the present case, also to illustrate) calculations of vascular tree properties.

In some embodiments, the tree model is represented by a 1-D array. For example, the 9-branch tree in FIG. 3C is represented by a 9-element array: a=[0 1 1 2 2 3 3 4 4], which lists tree nodes in a breadth-first order.

In some embodiments, during a reconstruction process, spatial location and radius of segments on each branch are sampled every small distance, for example every 1 mm, or every 0.1 mm to every 5 mm In some embodiments, tree branches, corresponding to vessel segments between modeled bifurcations, correspond to vessel segments of a length of 1 mm, 5 mm, 10 mm, 20 mm, 50 mm, and even longer.

In some embodiments, sampling every small distance increases the accuracy of a geometric model of the vessels, thereby increasing accuracy of flow characteristics calculated based on the geometric measurements.

In some embodiments, the tree model is a reduced tree, limited to a single segment of a vessel, between two consecutive bifurcations of the vascular system. In some embodiments, the reduction is to a region of a bifurcation, optionally comprising a stenosis.

Measuring flow from time intensity curves in angiographic sequences

In some embodiments, a physical model of fluid flow in the coronary vessel tree calculated, including physical characteristics such as pressure and/or flow rate, and/or flow resistance, and/or shear stress, and/or flow velocity.

In an example embodiment, a techniques based on the analysis of concentration-distance-time curves is used. The techniques perform well in conditions of pulsatile flow. An example concentration-distance-time curve technique is the concentration-distance curve matching algorithm.

Using the above-mentioned technique, a concentration of contrast material, such as iodine, present at a particular distance along a vessel segment, is found by integrating pixel intensities in angiogram(s) across a vessel lumen perpendicular to the centerline. An optimal shift is found in a distance axis between consecutive concentration-distance curves. A blood flow velocity is then calculated by dividing the shift by the time interval between the curves. Several variations of the above technique have been reported in the following references, the contents of which are hereby incorporated herein by reference: The four above-mentioned articles by Seifalian et al; the above-mentioned article titled: "Determination of instantaneous and average blood flow rates from digital angiograms of vessel phantoms using distance-density curves", by Hoffmann et al; the above-mentioned article titled: "Comparison of methods for instantaneous angiographic blood flow measurement", by Shpilfoygel et al; and the article titled: "Quantitative angiographic blood flow measurement using pulsed intra-arterial injection", by Holdsworth et al.

Measuring flow using other modalities

In some embodiments flow is calculated from ultrasound measurements. Several variations of the above mentioned ultrasound technique have been reported in above-mentioned references, the contents of which are hereby incorporated herein by reference: the above-mentioned article titled: "Noninvasive Measurement of Coronary Artery Blood Flow Using Combined Two-Dimensional and Doppler Echocardiography", by Kenji Fusejima; the article titled: "New Noninvasive Method for Coronary Flow Reserve Assessment: Contrast-Enhanced Transthoracic Second Harmonic Echo Doppler", by Carlo Caiati et al; the article titled: "Validation of noninvasive assessment of coronary flow velocity reserve in the right coronary artery—A comparison of transthoracic echocardiographic results with intracoronary Doppler flow wire measurements", by Harald Lethena et al; the article titled: "Coronary flow: a new asset for the echo lab?" by Paolo Vocia et al; the review paper titled: "Non-invasive assessment of coronary flow and coronary flow reserve by transthoracic Doppler echocardiography: a magic tool for the real world", by Patrick Meimoun et al; and the article titled: "Detection, location, and severity assessment of left anterior descending coronary artery stenoses by means of contrast-enhanced transthoracic harmonic echo Doppler", by Carlo Caiati et al.

In some embodiments, other modalities of measuring flow in the coronary vessel tree are used. Example modalities include MRI flow measurement and SPECT (Single-photon emission computed tomography), or gamma camera, flow measurement.

It is noted that in some embodiments a vascular flow model is constructed without using flow measurements or pressure measurements, based on geometrical measurement taken from images of the vascular system.

It is noted that in some embodiments flow measurements are used to verify flow characteristics calculated based on a model constructed based on the geometric measurements.

It is noted that in some embodiments pressure measurements are used to verify flow characteristics calculated based on a model constructed based on the geometric measurements.

An example embodiment of producing a model in which stenoses are modeled as if they had been revascularized— stenosis inflation In some embodiments an estimation is made of a structure of a sick vessel as if the vessel has been revascularized to a healthy structure. Such a structure is termed an inflated structure—as if a stenosed vessel has been revascularized back to normal diameter.

In some embodiments a technique is used as described in the following references, the contents of which are hereby incorporated herein by reference: the article titled "Dedicated bifurcation analysis: basic principles", by Tuinenburg et al; the article titled "Quantitative Coronary Angiography in the Interventional Cardiology", by Tomasello et al; and the article titled "New approaches for the assessment of vessel sizes in quantitative (cardio-)vascular X-ray analysis", by Janssen et al.

A stenosis inflation procedure is optionally implemented for each one of the 2-D projections separately. In some cases a stenosis may occur in a region nearby to a bifurcation and in some cases the stenosis may occur along a vessel. The stenosis inflation procedure in the two cases is now described separately.

If the stenosis is not located at a bifurcation region, it is enough to assess flow in the sick vessel. Coronary vessel segments proximal and distal to the stenosis are relatively free of disease and are referred to as reference segments. An algorithm optionally calculates a coronary edge by interpolating the coronary vessel segments considered free from illness located proximally and distally to the region of stenosis with the edges of the region of the stenosis. The algorithm optionally reconstructs a reference coronary segment that is as if free from disease.

In some embodiments the technique includes calculation of a mean value of the diameters of a vessel lumen in the segment of reference located upstream and downstream to the lesion.

If the stenosis is located at a bifurcation region, two example bifurcation models are defined: a T-shape bifurcation model and a Y-shape bifurcation model.

The bifurcation model, T-shape or Y-shape, is optionally detected by analyzing arterial contours of three vessel segments connected to the bifurcation. Calculation of a flow model for an inflated healthy vessel diameter is based on calculating as if each of the three segments connected to the bifurcation has a healthy diameter. Such a calculation ensures that both a proximal and a distal main (interpolated) reference diameter are based on arterial diameters outside the bifurcation core.

A reference diameter function of a bifurcation core is optionally based on a reconstruction of a smooth transition between the proximal and the distal vessel diameters. As a result, the reference diameter of the entire main section can be displayed as one function, composed of three different straight reference lines linked together.

An example of producing a model of physical characteristics of a vascular system Some example embodiments of methods for producing a model of physical characteristics of a vascular system are now described.

An example vascular system which will be used in the rest of the description below is the coronary vascular system.

In some embodiments of the invention, in order to evaluate an FFR index in a stenosed branch of a vessel tree, a one dimensional model of the vessel tree is used to estimate the flow in the stenosed branch before and optionally also after stent implantation.

In some embodiments of the invention, in order to evaluate an FFR index in a stenosed branch of a vessel tree, a one dimensional model of the vessel tree is used to estimate the flow in the stenosed branch before and optionally also after stenosis inflation.

Based on maximal peak flow of 500 mL/min and artery diameter of 5 mm, a maximal Reynolds number of the flow is:

$$Re_{peak\_flow} = \frac{4Q_{peak\_flow}}{\pi d_{max} v} = \frac{4 \cdot 500_{mL/min}}{\pi \cdot 5_{mm} \cdot 3.5_{cP}} \approx 600 \quad \text{Equation 5.1}$$

The above calculation assumes laminar flow. In laminar flow it is assumed, for example, that blood is a Newtonian and homogenous fluid. Another assumption which optionally may be made is that flow in vessel branches is 1-D and fully developed across the cross section of the vessel.

Based on the assumptions, a pressure drop in each segment of a vessel tree is approximated according to Poiseuille formulation in straight tubes:

$$\Delta P_i = \frac{128 \mu L_i}{\pi \cdot d_i^4} Q_i = \Re_i Q_i \quad \text{Equation 5.2}$$

Where $\Re_i$ is a viscous resistance to flow of a segment of the vessel. Minor losses, due to bifurcations, constrictions and curvatures of the vessels are optionally added as additional resistances in series, according to the Darcy-Weisbach formulation:

$$\Delta p = \frac{\rho V^2}{2} \cdot \sum K_i = \frac{8 \rho Q^2}{\pi^2 d^4} \cdot \sum K_i \quad \text{Equation 5.3}$$

$$\Re(Q) = \frac{\Delta p}{Q} = \left( \frac{8 \rho}{\pi^2 d^4} \cdot \sum K_i \right) \cdot Q \quad \text{Equation 5.4}$$

where $K_i$ are corresponding loss coefficients.

Figure 4:
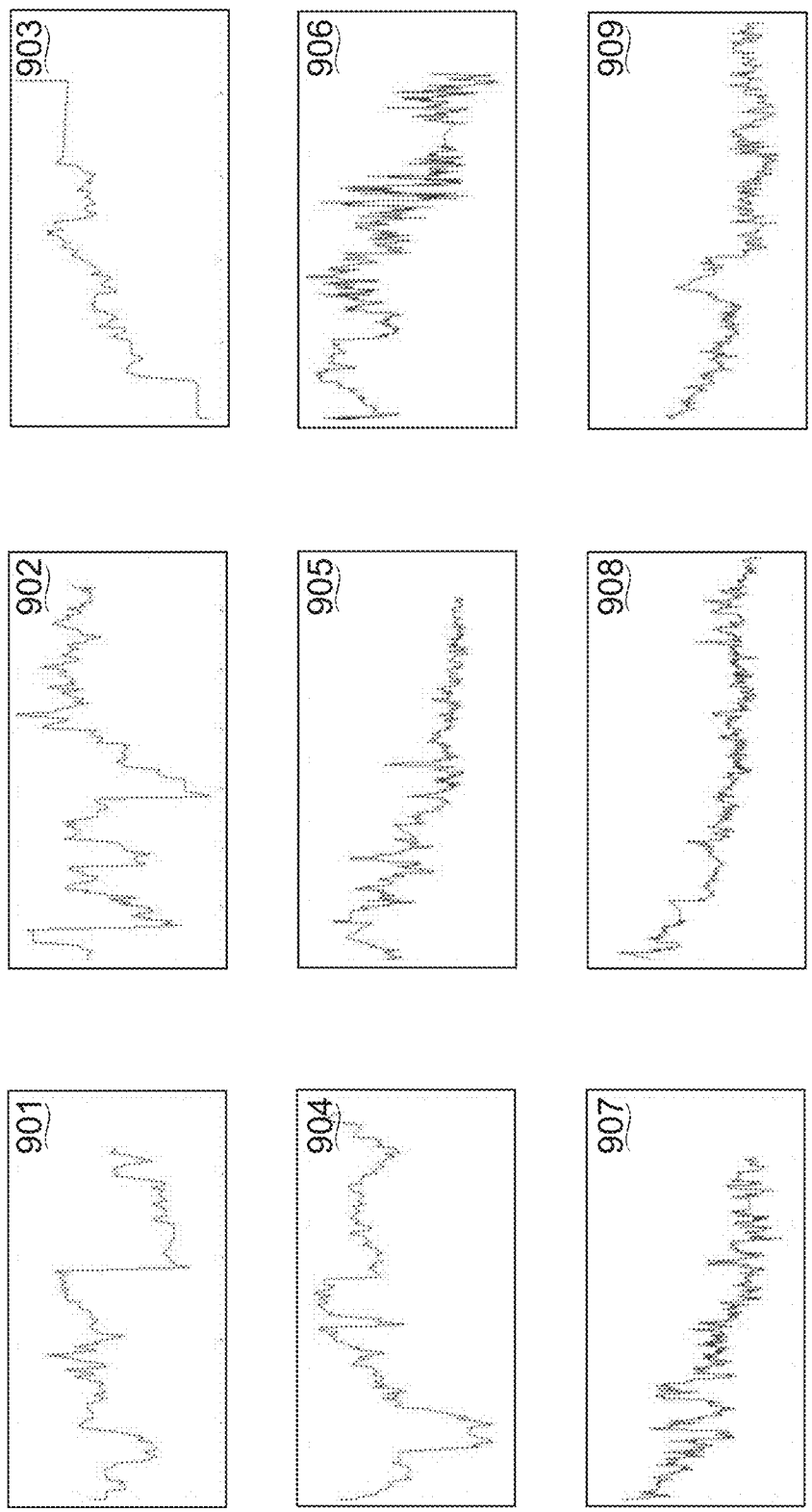
FIG. 4 is a set of nine graphical illustrations of vessel segment radii produced according to an example embodiment of the invention, along the branches of the coronary vessel tree model depicted in FIG. 3C, as a function of distance along each branch, according to some exemplary embodiments of the invention.

Reference is now made to FIG. 4, which is a set of nine graphical illustrations 901-909 of vessel segment radii produced according to an example embodiment of the invention, along the branches of the coronary vessel tree model 330 depicted in FIG. 3C, as a function of distance along each branch. Relative distance along the vessel segment is plotted in the X direction (horizontally), and relative radius is plotted in the Y direction (vertically).

The resistance of a branch to flow is calculated as the sum of the individual resistances of segments along the branch:

$$\Re_{branch} = \int_L \frac{8\mu}{\pi r^4} dl = \frac{8\mu}{\pi} \int_L \frac{dl}{r(l)^4} \quad \text{Equation 5.5}$$

or $$\Re_{branch} = \frac{8 \times 0.035_{g/cm \cdot s}}{\pi} \sum \frac{dl_i}{r_i^4} \quad \text{Equation 5.6}$$

A resistance array corresponding to the example depicted in FIG. 3C is:

$\Re_s$=[808 1923 1646 1569 53394 10543 55341 91454 58225], where the resistance to flow is in units of mmHg*s/mL.

The above resistance array is for a vessel with stenosis, as evidenced by a peak of 91454 [mmHg*s/mL] in the resistance array.

A resistance array for a tree model without stenosis is optionally calculated, based on Quantitative Coronary Angiography (QCA) methods for removing stenoses greater than 50% in area.

In some embodiments, a tree model without stenosis is optionally calculated by replacing a stenosed vessel by an inflated vessel, that is, geometric measurements of a stenosed vessel section are replaced by measurements appropriate for an inflated vessel.

In some embodiments geometric data (diameter and/or cross-sectional area) which is used for the inflated vessel is a maximum of the geometric data of the unstenosed vessel at a location just proximal to the stenosed location and at a location just distal to the stenosed location.

In some embodiments geometric data (diameter and/or cross-sectional area) which is used for the inflated vessel is a minimum of the geometric data of the unstenosed vessel at a location just proximal to the stenosed location and at a location just distal to the stenosed location.

In some embodiments geometric data (diameter and/or cross-sectional area) which is used for the inflated vessel is an average of the geometric data of the unstenosed vessel at a location just proximal to the stenosed location and at a location just distal to the stenosed location.

In some embodiments geometric data (diameter and/or cross-sectional area) which is used for the inflated vessel is calculated as a linear function of the geometric data of the unstenosed vessel between a location proximal to the stenosed location and a location distal to the stenosed location, that is, the inflated value is calculated taking into account distances of the stenosed location from the proximal location and from the distal location.

A stented, also termed inflated, resistance array for the example depicted in FIG. 4 is:

$\mathfrak{R}_{n=}$[808 1923 1646 1569 53394 10543 55341 80454 51225].

The peak resistance, which was 91454 [mmHg*s/mL], is replaced in the inflated, or stented model, by 80454 [mmHg*s/mL].

Figure 5:
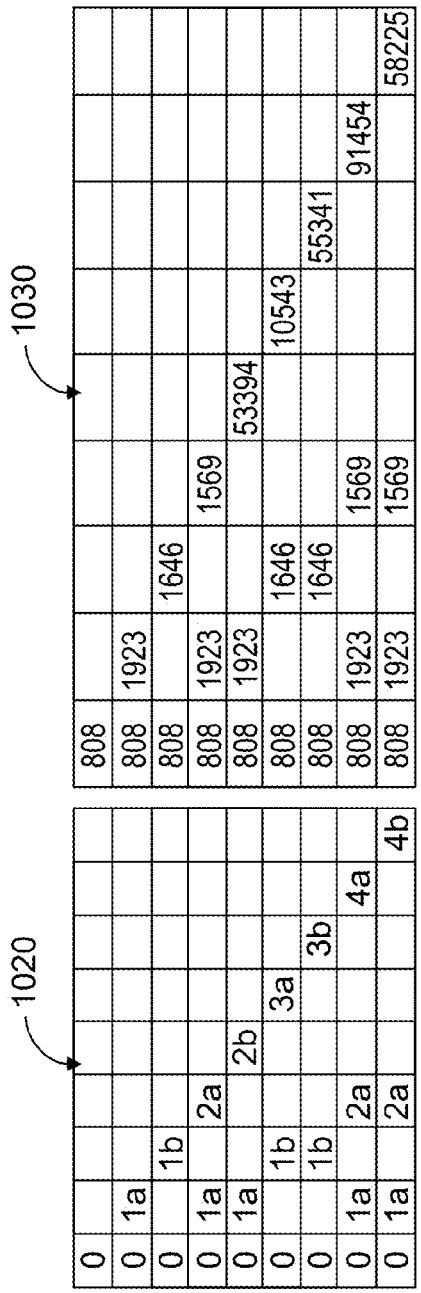
FIG. 5 depicts a coronary tree model, a combination matrix depicting tree branch tags, and a combination matrix depicting tree branch resistances, all produced according to some exemplary embodiments of the invention.

Reference is now made to FIG. 5, which depicts a coronary tree model 1010, a combination matrix 1020 depicting tree branch tags, and a combination matrix 1030 depicting tree branch resistances, all produced according to an example embodiment of the invention.

The tree model is an example tree model with nine branches, tagged with branch numbers 0, 1a, 1b, 2a, 2b, 3a, 3b, 4a and 4b.

The combination matrix 1020 includes nine rows 1021-1029, which contain data about nine stream lines, that is, nine paths through which fluid can flow through the tree model. Five of the rows 1025-1029 include data for five full stream lines, in darker text, for five paths which go a full way to outlets of the tree model. Four of the rows 1021-1024 include data for partial streamlines, in lighter text, for four paths which are not fully developed in the tree model, and do not go a full way to outlets of the tree model.

The combination matrix 1030 depicts rows for the same tree model as depicted in the combination matrix 1020, with branch resistances located in matrix cells corresponding to branch tags in the combination matrix 1020.

After calculating a resistance of each branch, stream lines are defined from the tree origin, branch 0 to each outlet. To keep track of the stream lines, branches which constitute each stream line are listed in a combination matrix, as shown for example in FIG. 5.

Figure 6:
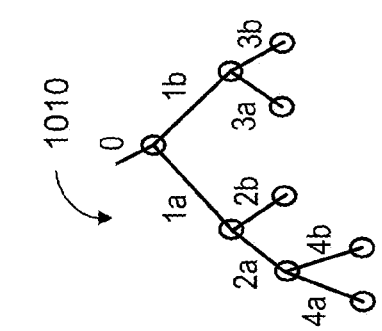
FIG. 6 depicts a tree model of a vascular system, with tags numbering outlets of the tree model, produced according to an example embodiment of the invention, the tags corresponding to stream lines, according to some exemplary embodiments of the invention.

In some embodiments, defined stream lines are also numbered, as shown in FIG. 6.

Reference is now made to FIG. 6, which depicts a tree model 1100 of a vascular system, with tags 1101-1105 numbering outlets of the tree model 1100, produced according to an example embodiment of the invention, the tags corresponding stream lines.

A pressure drop along a stream line j is calculated as a sum of pressure drops at each of its component branches (i), according to:

$$dp_j = \Sigma \mathfrak{R}_i Q_i \qquad \text{Equation 5.7}$$

when each branch has a different flow $Q_i$.

Based on a principle of mass conservation at each bifurcation, the flow rate in a mother branch is the sum of flow rates of daughter branches. For example:

$$Q_{1a} = Q_{2a} + Q_{2b} = Q_{4a} + Q_{4b} + Q_{2b} \qquad \text{Equation 5.8}$$

Thus, for example, a pressure drop along a stream line which ends at branch 4a is:

$$dp_{4a} = \mathfrak{R}_0 Q_0 + \mathfrak{R}_{1a} Q_{1a} + \mathfrak{R}_{2a} Q_{2a} + \mathfrak{R}_{4a} Q_{4a} = \qquad \text{Equation 5.9}$$
$$\mathfrak{R}_0 (Q_{4a} + Q_{4b} + Q_{2b} + Q_{3a} + Q_3) +$$
$$\mathfrak{R}_{1a}(Q_{4a} + Q_{4b} + Q_{2b}) + \mathfrak{R}_{2a}(Q_{4a} + Q_{4b}) +$$
$$\mathfrak{R}_{4a} Q_{4a} = Q_{4a}(\mathfrak{R}_0 + \mathfrak{R}_{1a} + \mathfrak{R}_{2a} + \mathfrak{R}_{4a}) +$$
$$Q_{4b}(\mathfrak{R}_0 + \mathfrak{R}_{1a} + \mathfrak{R}_{2a}) +$$
$$Q_{2b}(\mathfrak{R}_0 + \mathfrak{R}_{1a}) + Q_{3a}\mathfrak{R}_0 + Q_{3b}\mathfrak{R}_0 =$$
$$Q_4 ER_{4,4} + Q_5 ER_{4,5} + Q_1 ER_{4,1} + Q_2 ER_{4,2} + Q_3 ER_{4,3}$$

where $Q_j$ is a flow rate along stream line j, and $ER_{4,j}$ is a sum of common resistances of stream line j and stream line 4. A global expression is optionally formulated for the pressure drop along stream line j:

$$dp_j = \Sigma Q_i ER_{i,j} \qquad \text{Equation 5.10}$$

For a tree with k outlet branches, that is, for k full stream lines, a set of k linear equations are optionally used:

$$\begin{bmatrix} ER_{11} & ER_{12} & \ldots & ER_{1k} \\ ER_{21} & ER_{22} & \ldots & ER_{2k} \\ \ldots \\ ER_{k1} & ER_{k2} & \ldots & ER_{kk} \end{bmatrix} \begin{bmatrix} Q_1 \\ Q_2 \\ \ldots \\ Q_k \end{bmatrix} = \begin{bmatrix} dp_1 \\ dp_2 \\ \ldots \\ dp_k \end{bmatrix} \qquad \text{Equation 5.11}$$

$$\overline{\overline{A}} \times \overline{Q} = \overline{DP}$$

where indices 1 . . . k represent stream lines in the tree, and $Q_1 \ldots Q_k$ represent flow rates at corresponding outlet branches. The k×k matrix A consists of elements ER and is calculated from the combination matrix. For example, for the 5 stream lines tree shown in FIG. 6, the ER matrix is:

Equation 5.12

$$ER = \begin{bmatrix} \mathfrak{R}_0 + \mathfrak{R}_{1a} + \mathfrak{R}_{2b} & \mathfrak{R}_0 & \mathfrak{R}_0 & \mathfrak{R}_0 + \mathfrak{R}_{1a} & \mathfrak{R}_0 + \mathfrak{R}_{1a} \\ \mathfrak{R}_0 & \mathfrak{R}_0 + \mathfrak{R}_{1b} + \mathfrak{R}_{3a} & \mathfrak{R}_0 + \mathfrak{R}_{1b} & \mathfrak{R}_0 & \mathfrak{R}_0 \\ \mathfrak{R}_0 & \mathfrak{R}_0 + \mathfrak{R}_{1b} & \mathfrak{R}_0 + \mathfrak{R}_{1b} + \mathfrak{R}_{3b} & \mathfrak{R}_0 & \mathfrak{R}_0 \\ \mathfrak{R}_0 + \mathfrak{R}_{1a} & \mathfrak{R}_0 & \mathfrak{R}_0 & \mathfrak{R}_0 + \mathfrak{R}_{1a} + \mathfrak{R}_{2a} + \mathfrak{R}_{4a} & \mathfrak{R}_0 + \mathfrak{R}_{1a} + \mathfrak{R}_{2a} \\ \mathfrak{R}_0 + \mathfrak{R}_{1a} & \mathfrak{R}_0 & \mathfrak{R}_0 & \mathfrak{R}_0 + \mathfrak{R}_{1a} + \mathfrak{R}_{2a} & \mathfrak{R}_0 + \mathfrak{R}_{1a} + \mathfrak{R}_{2a} + \mathfrak{R}_{4b} \end{bmatrix}$$

$$ER = \begin{bmatrix} 56125 & 808 & 808 & 2731 & 2731 \\ 808 & 12997 & 2454 & 808 & 808 \\ 808 & 2454 & 57795 & 808 & 808 \\ 2731 & 808 & 808 & 95754 & 4300 \\ 2731 & 808 & 808 & 4300 & 55525 \end{bmatrix} \quad \text{Equation 5.13}$$

Figure 23:
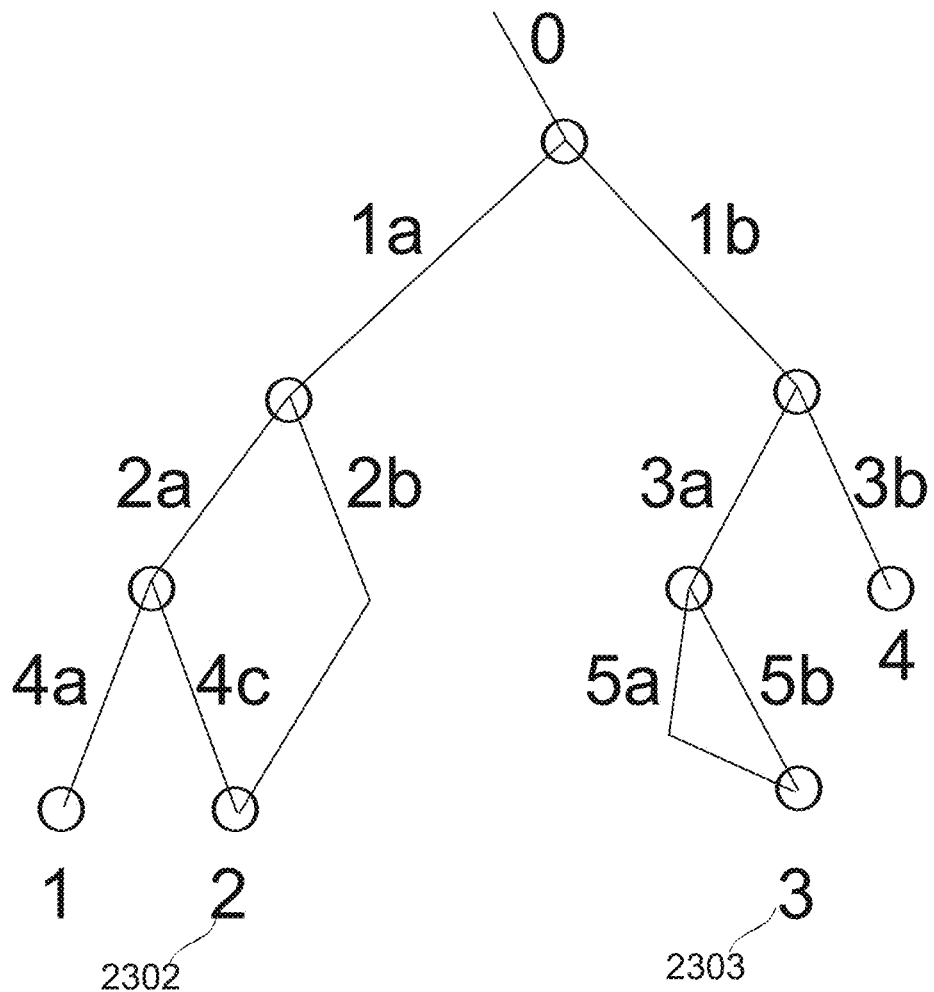
FIG. 23 shows an exemplary branching structure having recombining branches, according to some exemplary embodiments of the invention.

Reference is now made to FIG. 23, which shows an exemplary branching structure having recombining branches, according to some exemplary embodiments of the invention. In some embodiments of the invention, a provision is made for collateral and/or shunting vessels, where branches recombine in the tree.

In some embodiments of the invention, a streamline 2302, 2303 may be modeled which comprises a loop: for example, the loop comprising branch segments 2a and 4c, separating from and then recombining with branch segment 2b, or the loop comprising recombining branch segments 5a and 5b. In some embodiments of the invention, the requisite terms corresponding to the branch may be written to reflect that the vascular resistances operate in parallel. Thus, for example, the pressure drop along stream line 2302 may be written:

$$dp_{4c-2b} = \Re_0 Q_0 + \Re_{1a} Q_{1a} + \left( \frac{1}{\Re_{2a} + \Re_{4c}} + \frac{1}{\Re_{2b}} \right)^{-1} (Q_{4c} + Q_{2b}) \quad \text{Equation 5.13b}$$

In some embodiments, fluid pressure measurements are made, for example blood pressure measurements. Based on provided fluid pressure boundary conditions ($P_{in}$ and $P_{out\_i}$), a vector $\overline{DP}$ is defined, and $Q_i$ is calculated:

$$\overline{Q} = \overline{A}^{-1} \times \overline{DP} \quad \text{Equation 5.14}$$

For example, for a constant pressure drop of 70 mmHg between the origin and all the outlets, the following flow distribution between the outlets is calculated:

Q=[1.4356, 6.6946, 1.2754, 0.7999, 1.4282], where the units of flow are mL/s.

Figure 7:
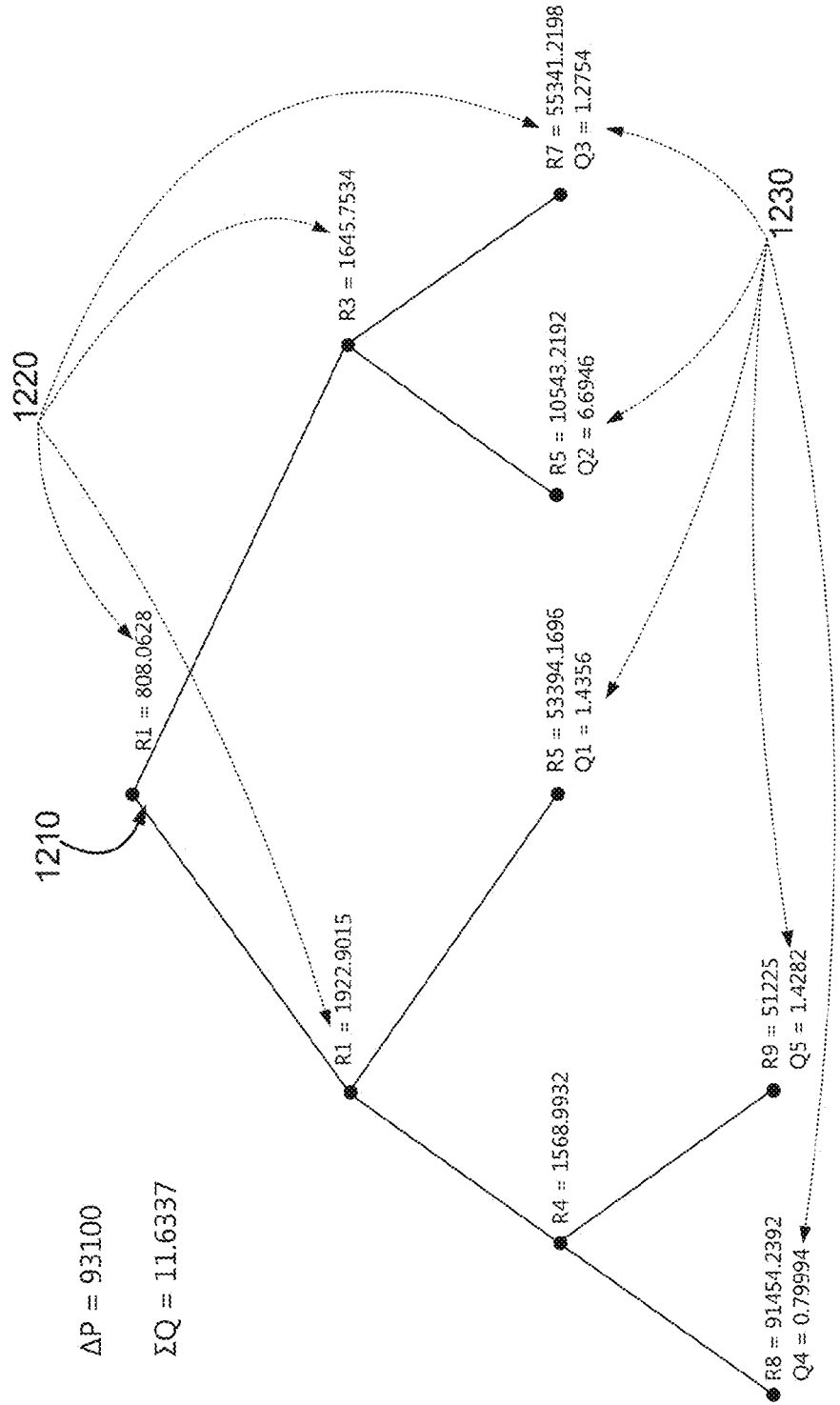
FIG. 7 is a simplified illustration of a vascular tree model produced according to an example embodiment of the invention, including branch resistances $R_i$ at each branch and a calculated flow $Q_i$ at each stream line outlet, according to some exemplary embodiments of the invention.

The result is an output of the above method, and is depicted in FIG. 7.

Reference is now made to FIG. 7, which is a simplified illustration of a vascular tree model 1210 produced according to an example embodiment of the invention, including branch resistances $\Re_i$ 1220 [mmHg*s/mL] at each branch and a calculated flow $Q_i$ 1230 [mL/s] at each stream line outlet.

In some embodiments, two models of a tree are calculated—a first model with stenoses, optionally as measured for a specific patient, and a second model without stenoses. FFR is calculated for each branch using the formula:

$$FFR = \frac{Q_S}{Q_N} \quad \text{Equation 5.15}$$

For example, for the tree described above, the FFR calculated for each one of the 9 branches is:

FFR=[1.00 1.00 1.00 1.00 1.00 1.00 1.00 0.8846 0.8874]

It should be emphasized that the above-calculated FFR, expressed directly in terms of flows $Q_S, Q_N$ ($FFR_{flow} = Q_S/Q_N$), is distinct in its determination from the pressure measurement-derived FFR ($FFR_{pressure} = P_d/P_a$), calculated based on pressure differences distal $P_d$ and proximal $P_a$ to a stenosis. Furthermore, rather than being a comparison of two variables of a fixed system state, it is a comparison of two distinct states of the system.

For $FFR_{pressure}$, a finding of a large difference in pressure measurements across a stenotic lesion (for example, $FFR_{pressure} \leq 0.75$) suggests that removing the lesion would remove a substantial resistance $\Re$ to flow, whereby blood flow, in turn, would substantially increase. "Substantially", in this case, means "enough to be medically worthwhile". This chain of reasoning relies on simplifying assumptions about remaining pressures and resistances in the vascular system different in detail from those recited hereinabove in relation to $FFR_{flow}$.

Nevertheless, the two indices are closely related in what they describe. FFR as such—although it is commonly measured by pressure differences in a fixed system state—is defined as the ratio of maximum blood flow in a stenotic artery to maximum blood flow if the same artery were normal. Thus, $FFR_{flow}$ and $FFR_{pressure}$ may be characterized as differently arrived-at indexes of the same desired information: what fraction of flow can be restored, at least in principle, by intervention at a particular region of the cardiac vasculature.

The acceptance of $FFR_{pressure}$ by the field relates also to experience and correlations with clinical outcome. There is, accordingly, a potential benefit to supplying a replacement for $FFR_{pressure}$ which describes the vascular system in terms medical professionals are accustomed to. The index which FFR provides estimates the potential for restoration of blood flow after treatment. It is a potential benefit, therefore, that $FFR_{flow}$—at least insofar as it comprises a ratio of flows—relates to the parameter of direct medical interest as closely as $FFR_{pressure}$ itself, even though it is arrived at by a different route.

Also, as for $FFR_{pressure}$, a goal of determining $FFR_{flow}$, in some embodiments of the present invention, is the guidance of medical decision making by providing a rapidly calculable, easily interpreted, index. It is potentially sufficient for a medical professional seeking diagnostic assistance to establish by a vascular index such as $FFR_{flow}$ that intervention will make a medically meaningful change in perfusion. A ratio index is exemplary of an index that compactly expresses such change. It should also be noted that by describing an index that expresses a potential for change, $FFR_{flow}$, like $FFR_{pressure}$ itself, potentially reduces the effects of errors and/or distraction in the absolute determination of vascular perfusion characteristics.

Quality of Results

Figure 24:
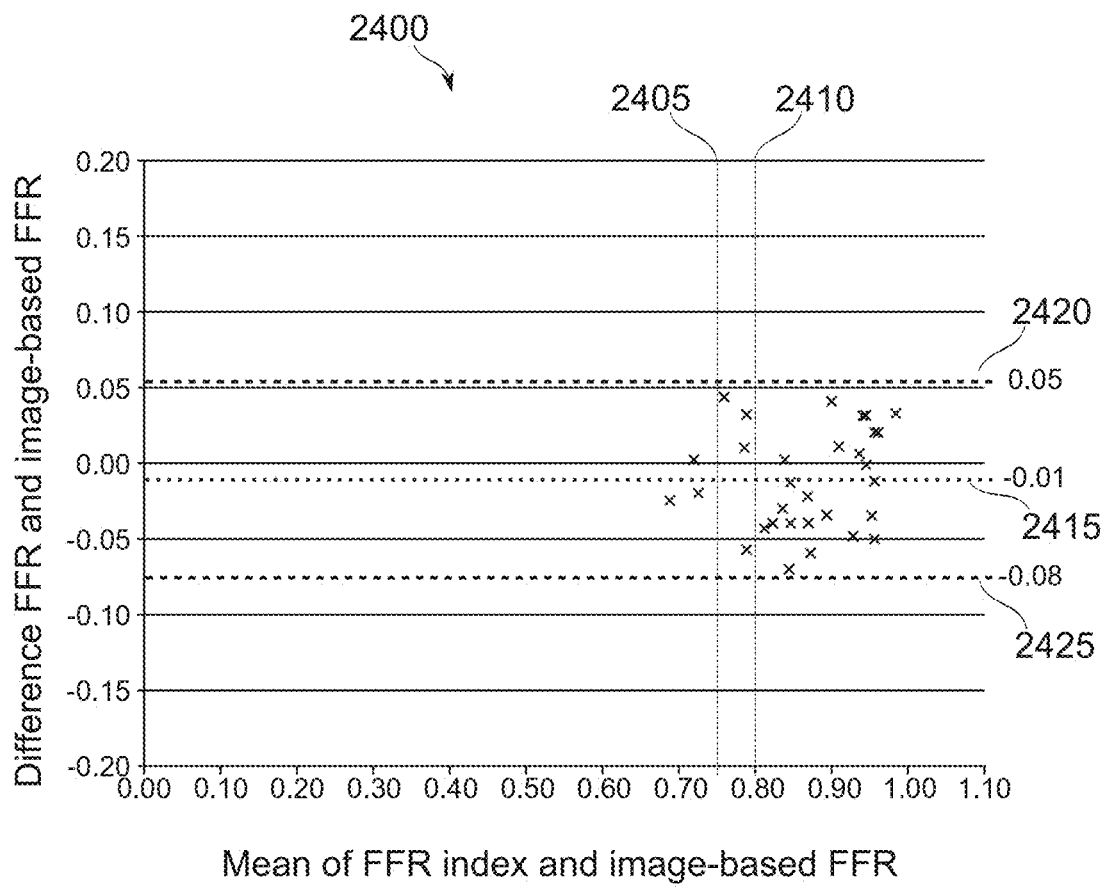
FIG. 24 is a Bland-Altman plot of the difference of FFR index and image-based FFR index as a function of their average, according to some exemplary embodiments of the invention.

Reference is now made to FIG. 24, which is a Bland-Altman plot 2400 of the difference of FFR index ($FFR_{pressure}$ and image-based FFR index ($FFR_{flow}$) as a function of their average, for some exemplary embodiments of the invention.

In the exemplary graph, the mean difference of FFR index and image-based FFR 2415 is −0.01 (N=34 lesions, from 30 patients), with the 2 standard deviation lines 2420, 2425 found at 0.05 and −0.08. Lines 2405, 2410 mark the typical cutoffs between preferably "non-treated" FFR (FFR>0.80), preferably "treated" FFR (FFR<0.75), and intermediate FFR values (0.075≤FFR≤0.80). On a linear correlation, the $R^2$ value was 0.85. Specificity was found to be 100%.

These validation results show that image-based FFR is potentially a direct substitute for FFR calculated from pressure measurement results.

In some embodiments of the invention, the relationship of FFR calculated from images to a baseline FFR (for example, FFR measured by pressure, or FFR measured by contrast flow before and after actual stent implantation) comprises a specificity of about, for example, 90%, 95%, 100%, or another intermediate or smaller specificity. An $R^2$ value describing correlation with a baseline FFR is about, for example, 0.75, 0.80, 0.85, 0.90, or another larger, smaller, or intermediate value.

Some example implementations of calculating an index

In some embodiments of the invention, image processing techniques and numerical calculations are combined for determining a physiological index (for example, $FFR_{flow}$) which is functionally equivalent to the pressure-derived Fractional Flow Reserve (FFR(pressure)). In some embodiments, functional equivalence is direct; in some embodiments, achieving functional equivalence comprises the application of further calibration factors (representing, for example, an offset to vascular width, a change in blood viscosity, or simply an equivalence factor and/or function). The integration of the above-mentioned techniques potentially enables providing a minimally invasive assessment of blood flow during a diagnostic catheterization, and provides an appropriate estimation of the functional significance of coronary lesions.

In some embodiments of the invention, a novel physiological index provides a physiological index which potentially enables evaluating the need for percutaneous coronary intervention, and supports making real-time diagnostic and interventional (treatment) decisions. The minimal-invasive method potentially prevents unnecessary risk to a patient, and/or reduces time and/or cost of angiography, hospitalization and/or follow-up.

In some embodiments, a scientific model, based on patient data, is provided, which identifies geometrical characteristics of the patient's vascular system, comprising a vascular tree thereof, or even a single vessel, and relevant hemodynamic information, equivalent in application to the present-day invasive FFR method (for example $FFR_{flow}$).

In addition, the model potentially allows examining a combination of 3D reconstruction of the vessel and a numerical flow analysis to determine functional significance for a coronary lesion.

Some embodiments of the present invention perform 1-D reconstruction of one or more coronary artery segments and/or branches during coronary angiography, and a computational/numerical flow analysis in order to evaluate the arterial pressure, flow rate and/or flow resistance therealong.

Some embodiments of the present invention perform 3-D reconstruction of one or more coronary artery segments and/or branches during coronary angiography, and a computational/numerical flow analysis in order to evaluate the arterial pressure, flow rate and/or flow resistance therealong.

In embodiments of the invention in which the vascular function index is calculated based only on the stenotic model, the resistance $\mathfrak{R}_S$ contributed by a stenosis to the total resistance of the lesion's crown is evaluated. The volume $V_{crown}$ of the crown distal to the stenosis is also calculated. An FFR index ($FFR_{resistance}$) can then be calculated as a function which decreases with $\mathfrak{R}_S$ and $V_{crown}$. A representative example of such a function includes, without limitation, $$FFR = \left(1 + \frac{\mathfrak{R}_S k V_{crown}^{3/4}}{P_a - P_0}\right)^{-1} \qquad \text{Equation 5.15a}$$

where $P_a$ is the aortic pressure, $P_0$ is the pre-capillary pressure and k is a scaling law coefficient which can be adapted to the aortic pressure.

Figure 8:
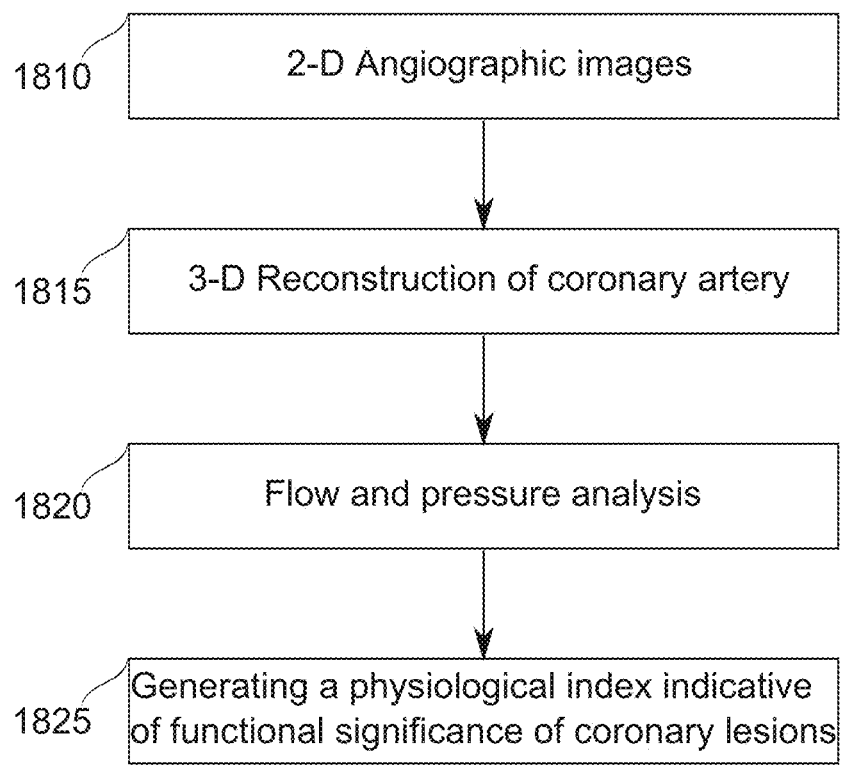
FIG. 8 is a simplified flow chart illustration of FFR index generation, according to some exemplary embodiments of the invention.

Reference is now made to FIG. 8, which is a simplified flow chart illustration of an example embodiment of the invention. This embodiment is particularly useful when a vessel function index, such as FFR is calculated based on two models of the vasculature.

FIG. 8 illustrates some portions of a method according to the example embodiment. The method includes receiving at least two 2-D angiographic images of a portion of a coronary artery of a patient (1810) and reconstructing a 3-D tree model of a coronary artery system (1815), and if there is a lesion, including the lesion.

A flow analysis of blood flow and optionally arterial pressure along a segment of interest, based on the tree model and optionally on other available hemodynamic measurements, such as aortic pressure and/or amount of injected contrast.

The example embodiment just described potentially provides a minimally-invasive physiological index indicative of functional significance of coronary lesions.

The example method is optionally performed during a coronary angiography procedure, and calculations are optionally performed during the coronary angiography procedure, such that the minimally-invasive physiological index is provided in real-time.

Figure 9:
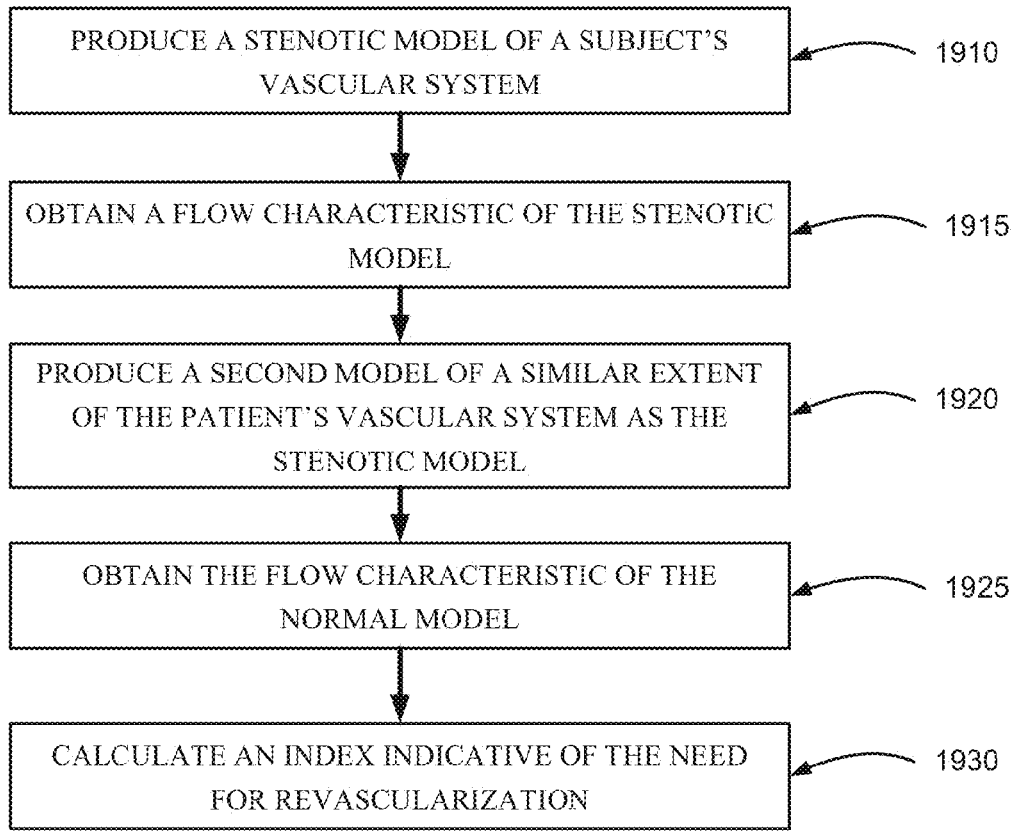
FIG. 9 is a simplified flow chart illustration of another method of FFR index generation, according to some exemplary embodiments of the invention.

Reference is now made to FIG. 9, which is a simplified flow chart illustration of another example embodiment of the invention.

FIG. 9 illustrates a method for vascular assessment which includes:

producing a stenotic model of a subject's vascular system, the stenotic model comprising geometric measurements of the subject's vascular system at one or more locations along a vessel centerline of at least one branch of the subject's vascular system (1910);

obtain a flow characteristic of the stenotic model (1915);

producing a second model of a similar extent of the patient's vascular system as the stenotic model (1920);

obtaining the flow characteristic of the normal model (1925); and calculating an index indicative of the need for revascularization, based on the flow characteristic in the stenotic model and on the flow characteristic in the normal model (1930).

Figure 10:
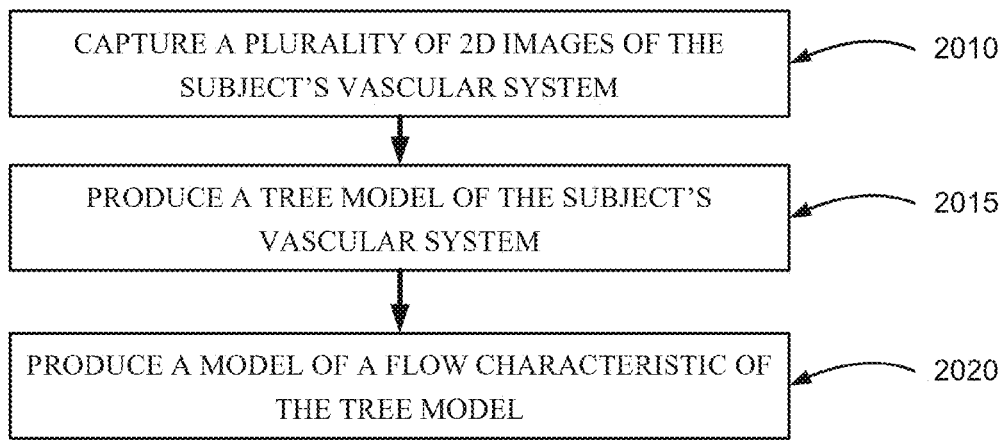
FIG. 10 is a simplified flow chart illustration of yet another method of FFR index generation, according to some exemplary embodiments of the invention.

Reference is now made to FIG. 10, which is a simplified flow chart illustration of yet another example embodiment of the invention.

FIG. 10 illustrates a method for vascular assessment which includes:

capturing a plurality of 2-D images of the subject's vascular system (2010);

producing a tree model of the subject's vascular system, the tree model comprising geometric measurements of the subject's vascular system at one or more locations along a vessel centerline of at least one branch of the subject's vascular system, using at least some of the plurality of captured 2-D images (2015); and producing a model of flow characteristics of the first tree model (2020).

Extents of the coronary tree model

In some embodiments, the extent of a first, stenosed model is just enough to include a stenosis, a section of vessel proximal to the stenosis, and a section of vessel distal to the stenosis.

In such an embodiment the extent of the first model is, in some cases, a segment of a vessel between bifurcations, including a stenosis in the segment. In some cases, especially when a stenosis is at a bifurcation, the extent includes the bifurcation, and sections of vessels proximal and distal to the stenosed bifurcation.

In some embodiments, an extent by which the first model extends proximal to the stenosis within a single segment is from as small as 1 or 2 millimeters, up to as much as 20 to 50 millimeters, and/or up to as much as the end of the segment itself.

In some embodiments, an extent by which the first model extends distal to the stenosis within a single segment is from as small as 1 or 2 millimeters, up to as much as 20 to 50 millimeters, and/or up to as much as the end of the segment itself.

In some embodiments, an extent by which the first model extends distal to the stenosis is measured by bifurcations of the vessel. In some embodiments, the first model extends distal to the stenosis by as few as 1 or 2 bifurcations, and in some embodiments by as much as 3, 4, 5, and even more bifurcations. In some embodiments the first model extends distal to the stenosis as far as resolution of the imaging process allows discerning distal portions of the vascular system.

A second model, of the same extent as the first model, is optionally produced, with the stenosis inflated as if the stenosis had been revascularized back to normal diameter.

Producing a model of physical characteristics of a vascular system

In an example implementation, given a proximal arterial pressure, $P_a$, [mmHg], flow rate through a segment of interest $Q_S$, [mL/s] is optionally derived from a concentration of iodine contrast material, based on an analysis of concentration-distance-time curves, and a geometric description of the segment of interest, including diameter d(l) [cm], and/or volume V(l) [ml] as a function of segment length.

In some embodiments, especially in case of large vessels such as the Left Anterior Descending coronary artery (LAD), blood flow can be measured for obtaining a flow model using a transthoracic echo Doppler, or other modalities such as MRI or SPECT.

For a given segment, a total resistance of the segment ($R_t$, [mmHg*s/mL]) is optionally calculated by dividing arterial pressure by flow rate:

$$R_t = \frac{P_a}{Q_s} \quad \text{Equation 5.16}$$

where $R_t$ corresponds to total resistance, $P_a$ corresponds to arterial pressure, and $Q_s$ corresponds to flow rate through the vessel segment.

From geometric description of the segment, a local resistance of the stenosis in the segment $R_s$, [mmHg*s/mL] is estimated. Estimation of $R_s$ may be made by any one or more of the following methods: using an empirical lookup table; and/or using a function such as described in the above mentioned Kirkeeide reference; and/or by a cumulative summation of Poiseuille resistances:

$$R_s = \frac{128\mu}{\pi} \int \frac{dl}{d^4} \quad \text{Equation 5.17}$$

where integration is over samples of the segment (dl), d is optionally an arterial diameter of each sample, and $\mu$ is 0.035 g·cm$^{-1}$·s$^{-1}$, optionally blood viscosity.

The segment's downstream resistance is calculated for the segment $R_n$, [mmHg*s/mL] as follows:

$$R_n = R_t - R_s \quad \text{Equation 5.18}$$

A normal flow through the segment without stenosis $Q_n$, [mL/s], is calculated for example as follows:

$$Q_n = \frac{P_a}{R_n} \quad \text{Equation 5.19}$$

where $Q_n$ is an input flow to the segment, $P_a$ is pressure proximal to the segment, and $R_n$ is resistance to flow by vessels distal to the segment.

Another form of Fractional Flow Reserve (FFR$_{contrast\text{-}flow}$) is optionally derived as a ratio between measured flow rate through the stenosed segment and normal flow rate through the segment without stenosis:

$$FFR = \frac{Q_s}{Q_n} \quad \text{Equation 5.20}$$

In some embodiments, an index indicative of the potential effect of revascularization, such as an FFR index (for example, FFR$_{contrast\text{-}flow}$), is calculated using the data described below:

proximal arterial pressure $P_a$, [mmHg] is measured;

a total inlet flow through a vessel origin, such as the coronary origin $Q_{total}$, [mL/s], is derived from a concentration of contrast material (such as iodine), optionally based on the analysis of concentration-distance-time curves. In some embodiments, especially for large vessels such as the Left Anterior Descending (LAD) coronary artery, flow is optionally recorded using a transthoracic echo Doppler and/or other modalities such as MRI and SPECT;

a subject's specific anatomy, including one or more of the following:

a geometric description of arterial diameters along vessel tree segments, for example up to 3-4 generations as a function of segment length d(l) [cm];

a geometric description of arterial lengths along the vessel tree segments ($L_i$ [cm]), for example up to 1-2 generations downstream of the segment of interest, and an accumulative crown length ($L_{crown}$ [cm]) downstream to the segment of interest: $L_{crown} = \Sigma L_i$;

a geometric description of arterial volumes along the vessel tree segments $V_i$ [ml], for example up to 1-2 generations downstream of the segment of interest, and the accumulative crown volume ($V_{crown}$ [ml]) downstream to the segment of interest: $V_{crown} = \Sigma V_i$;

a myocardial mass (LV mass) distribution for the arterial segment of interest M [ml] (in some embodiments LV mass is optionally calculated using, for example, a transthoracic echo Doppler); and a reference parameter K or function F which correlates anatomic parameters such as described above with normal flow through the segment (without stenosis) $Q_n$, [mL/s], for example:

$$Q_n = K \cdot M \text{ or } Q_n = F(M) \qquad \text{Equation 5.21}$$

Using the above data, the index indicative of the potential effect of revascularization, such as the FFR index, is optionally calculated by performing the following calculations for each vessel segment under consideration:

from the geometric parameter of the tree, such as length, volume, mass and/or diameter, a normal flow $Q_n$ in the segment is obtained;

from arterial pressure a resistance distal to the segment ($R_n$, [mmHg*s/mL]) is calculated, for example as follows: $R_n = P_d/Q_n$;

from geometry a local resistance of the stenosis in the segment $R_s$, [mmHg*s/mL] is estimated, for example using one of the following methods:

a lookup table;

an empirical function such as described in the above mentioned Kirkeeide reference; and/or a cumulative summation of Poiseuille resistances $R_s = (124\mu)/\pi\int(dl)/(d^4)$ where the integration is over samples of the segment (dl), d is an arterial diameter of each sample, and $\mu$ is 0.035 g·cm$^{-1}$·s$^{-1}$ is optionally blood viscosity;

the total resistance for the segment $R_t$ [mmHg*s/mL] is optionally calculated as: $R_t = R_n + R_s$ the flow through the stenosis segment $Q_s$ [mL/s] is optionally calculated as: $Q_s = P_d/R_t$; and the index, such as the fractional flow reserve (FFR), for the segment is optionally calculated as: $FFR = Q_s/Q_n$.

It is noted that a sanity check for the above calculation can optionally be made by checking if the accumulated flow in the tree agrees with the measured total flow as follows: $Q_{total} = \Sigma Q_i$.

In some embodiments, the extent of the first model is such that it includes a stenosis, and extends distally as far as resolution of the imaging modality which produced the vessel model allows, and/or several bifurcations, for example 3 or 4 bifurcations distally to the stenosis. In some embodiments, the number of bifurcations is limited by the resolution to which vascular width can be determined from an image. For example, cutoff of the bifurcation order is set where the vascular width is no longer determinable to within a precision of 5%, 10%, 15%, 20%, or another larger, smaller, or intermediate precision. In some embodiments, sufficient precision is unavailable due, for example, to insufficient imaging resolution in the source images. Availability of a larger number of measurable bifurcations is a potential advantage for fuller reconstruction of the detailed vascular resistance in the crown vessels of a stenosis. It should be noted that in the current state of the art, CT scans generally provide a lower resolution than X-ray angiographic imaging, leading to a lowered availability of blood vessels from which vascular resistances can be determined.

In an example implementation, a total inlet flow through a coronary origin is optionally derived from a concentration of contrast material and optionally a subject's specific anatomy.

In some embodiments, data regarding the anatomy optionally includes a geometric description of arterial diameters along vessel segments up to 3-4 bifurcations distally to a stenosis, a geometric description of arterial lengths along vessel tree segments, a geometric description of arterial volumes along the tree segments, and/or a myocardial mass (LV mass) distribution for the arterial segment of interest.

In some embodiments, data regarding the anatomy optionally includes a geometric description of arterial diameters along vessel segments as far as the imaging modality allows distally to a stenosis, a geometric description of arterial lengths along vessel tree segments, a geometric description of arterial volumes along the tree segments, and/or a myocardial mass (LV mass) distribution for the arterial segment of interest.

In some embodiments, LV mass is optionally calculated by using a transthoracic echo Doppler.

In some embodiments, a reference scaling parameter or function which correlates anatomic parameters with normal flow through a segment without stenosis is used.

In some embodiments, the extent of a first model includes a stenosed vessel, and a second model includes a similar extent of the vascular system, with a healthy vessel similar to the stenosed vessel.

An FFR index ($FFR_{2-segment}$) is optionally calculated from a ratio between the measured flow rate in a stenosed vessel, and a flow rate in a neighboring healthy vessel.

In some embodiments, the index is adjusted by a proportion between a total length of vessels in the crowns of the stenosed vessel and the healthy vessel. A crown of a vessel is hereby defined as a sub-tree branching off the vessel. The total length of a crown is optionally derived from a 3-D reconstruction of the coronary tree.

Figure 11:
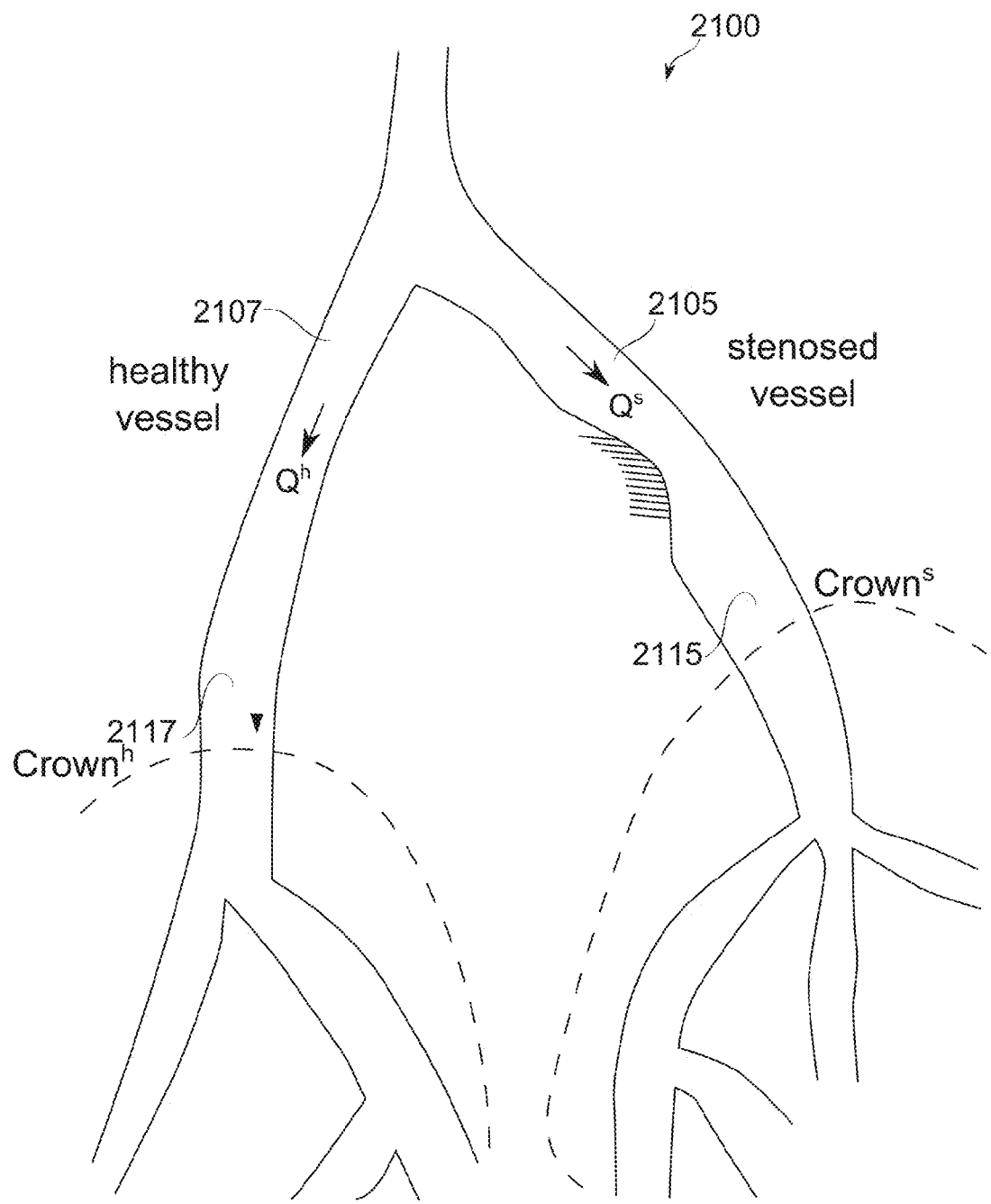
FIG. 11 is a simplified drawing of vasculature which includes a stenosed vessel and a non-stenosed vessel, as related to according to some exemplary embodiments of the invention.

Reference is now made to FIG. 11, which is a simplified drawing 2100 of vasculature which includes a stenosed vessel 2105 and a non-stenosed vessel 2107.

FIG. 11 depicts two vessels which are candidates for basing a flow characteristic comparison of the stenosed vessel 2105 and the non-stenosed vessel 2107. FIG. 11 also depicts the stenosed vessel crown 2115 and the non-stenosed vessel crown 2117.

It is noted that the two vessels in FIG. 11 seem to be especially good candidates for the comparison, since both seem to have similar diameters, and both seem to have similar crowns.

According to scaling laws, a linear relationship exists between a normal flow rate Q in an artery, and a total length of vessels in its crown. This relationship holds for both the neighboring healthy vessel, and the stenosed vessel.

For a healthy vessel:

$$Q_N^h = k \cdot L^h \qquad \text{Equation 6.1}$$

where $Q_N^h$ is a flow rate of a healthy vessel, k is a correction factor, and $L^h$ is a total length of crown vasculature of the healthy vessel.

For a stenosed vessel, similarly:

$$Q_N^s = k \cdot L^s \qquad \text{Equation 6.2}$$

where $Q_N^s$ is a flow rate of a stenosed vessel, k is a correction factor, and $L^s$ is a total length of crown vasculature of the stenosed vessel.

$FFR_{2-segment}$ is defined, in some embodiments, as a ratio between a flow rate in a stenosed artery during hyperemia, and the flow rate in the same artery in the absence of the stenosis (normal flow rate), as described by Equation 6.3 below. The above relationship yields a result for the FFR, calculated as a ratio between the measured flow rates in both vessels divided by the ratio between their respective total crown lengths.

It is noted that scaling laws also state the relationship between the normal flow rate and the total crown volume. In some embodiments, the index or FFR is optionally calculated from the above-mentioned ratio between the measured flow rates in the sick and healthy arteries, divided by a ratio between respective total crown volumes of a stenosed vessel and a normal vessel respectively, to the power of ¾.

$$FFR \equiv \frac{Q_S^s}{Q_N^s} = \frac{Q_S^s}{k \cdot L^s} = \frac{Q_S^s}{\frac{Q_N^h}{L^h} \cdot L^s} = \left(\frac{Q_S^s}{Q_N^h}\right) \cdot \frac{L^h}{L^s} \qquad \text{Equation 6.3}$$

Where $Q_N^s$ is an existing flow in a stenosed vessel, measured by any method described herein; $Q_N^h$ is an existing flow in a healthy vessel, measured by any method described herein; $L^s$ is a total crown length of the stenosed vessel; and $L^h$ is a total crown length of the healthy vessel.

The scaling laws also state a relationship between a normal flow rate and a total crown volume:

$$Q_N^h = k_v \cdot V_h^{3/4} \qquad \text{Equation 6.4}$$

where $Q_N^h$ is a flow rate of a healthy vessel, $k_v$ is a correction factor, and $V_h$ is a total volume of crown vasculature of the healthy vessel.

For a stenosed vessel, similarly:

$$Q_N^s = k_v \cdot V_s^{3/4} \qquad \text{Equation 6.5}$$

where $Q_N^s$ is a flow rate of a stenosed vessel, $k_v$ is a correction factor, and $V_h$ is a total volume of crown vasculature of the stenosed vessel.

An FFR is optionally calculated from the above-mentioned ratio between the measured flow rates in the sick and healthy vessels, divided by the ratio between the respective total crown volumes, raised to the power of ¾:

$$FFR = \left(\frac{Q_S^s}{Q_N^h}\right) \cdot \left(\frac{V_h}{V_s}\right)^{3/4} \qquad \text{Equation 6.6}$$

where $V_h$ and $V_s$ are measured, by way of a non-limiting example, by using a 3-D model of the vasculature.

An example hardware implementation

Figure 12A:
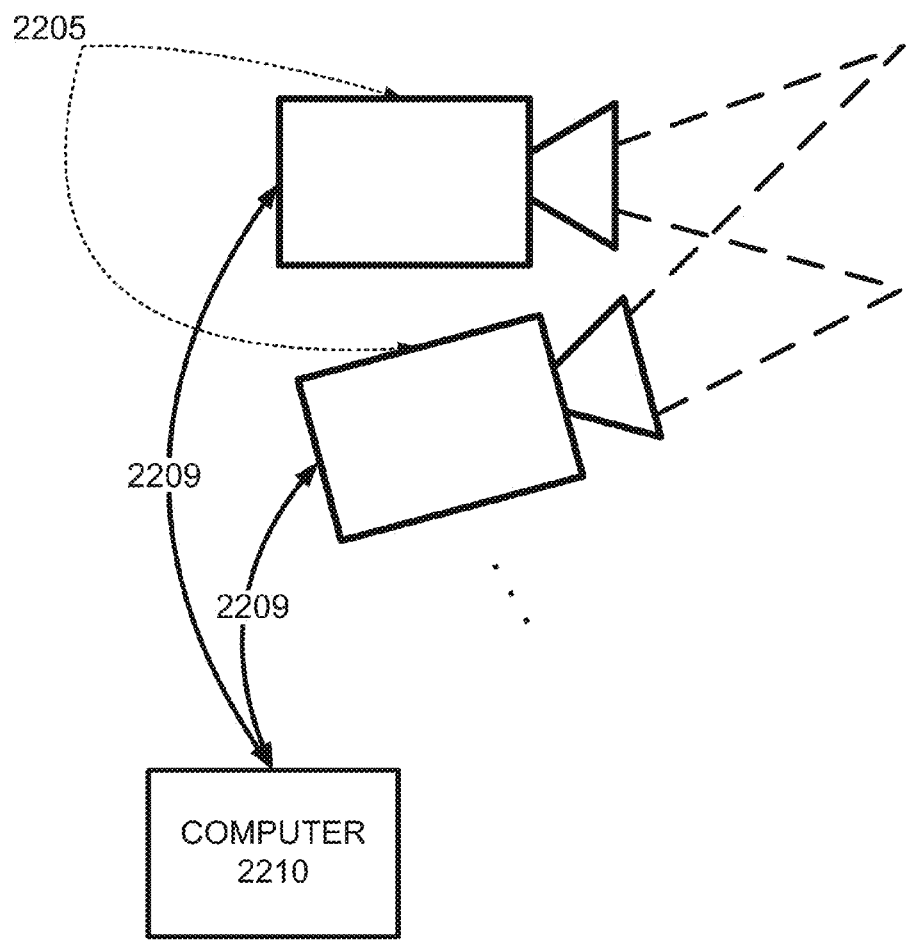
FIG. 12A is a simplified illustration of a hardware implementation of a system for vascular assessment, constructed according to some exemplary embodiments of the invention.

Reference is now made to FIG. 12A, which is a simplified illustration of a hardware implementation of a system for vascular assessment constructed according to an example embodiment of the invention.

The example system of FIG. 12A includes:

Two or more imaging devices 2205 for capturing a plurality of 2-D images of the patient's vascular system; a computer 2210 functionally connected 2209 to the two or more imaging devices 2205.

The computer 2210 is optionally configured to: accept data from the plurality of imaging devices 2205; produce a tree model of the patient's vascular system, wherein the tree model comprises geometric measurements of the patient's vascular system at one or more locations along a vessel centerline of at least one branch of the patient's vascular system, using at least some of the plurality of captured 2-D images; and produce a model of flow characteristics of the tree model.

In some embodiments a synchronization unit (not shown) is used to provide the imaging devices 2205 with a synchronization signal for synchronizing the capturing of 2-D images of the patient's vascular system.

Figure 12B:
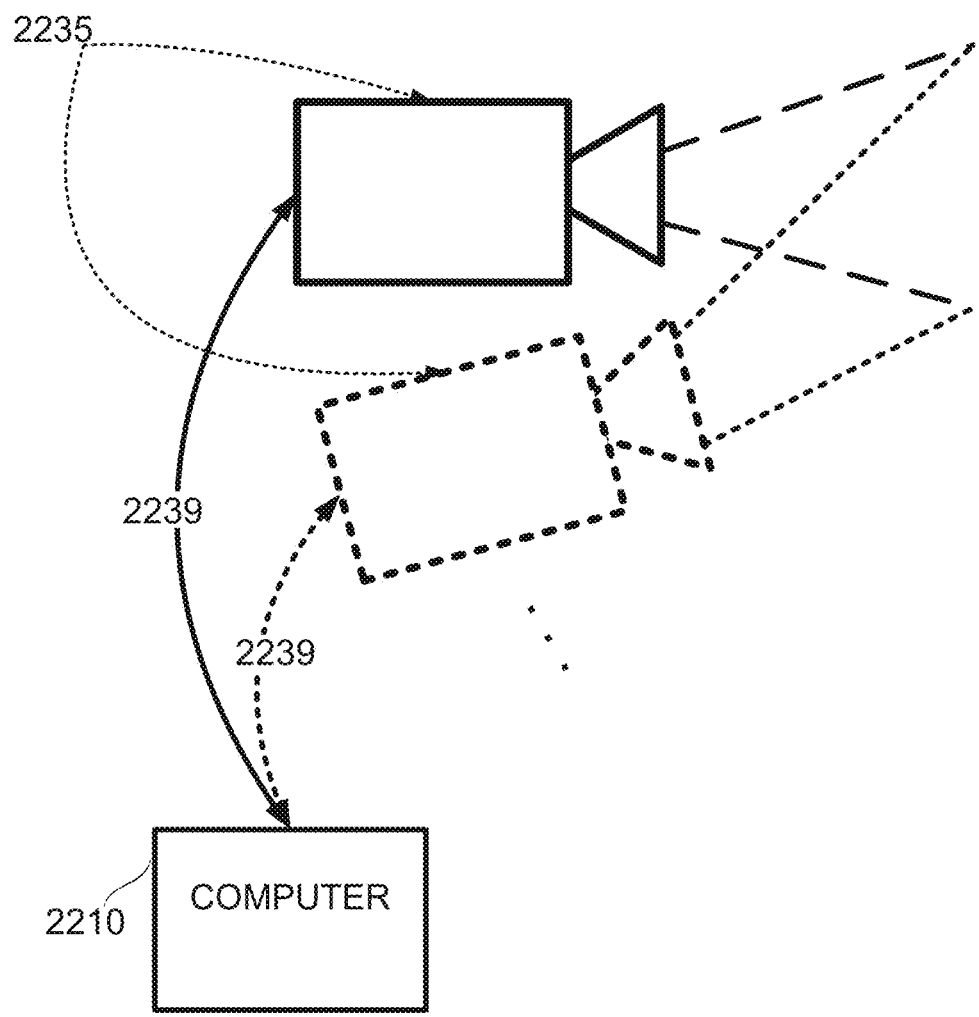
FIG. 12B is a simplified illustration of another hardware implementation of a system for vascular assessment constructed according to some exemplary embodiments of the invention.

Reference is now made to FIG. 12B, which is a simplified illustration of another hardware implementation of a system for vascular assessment constructed according to an example embodiment of the invention.

The example system of FIG. 12B includes:

One imaging device 2235 for capturing a plurality of 2-D images of the patient's vascular system and a computer 2210 functionally connected 2239 to the imaging device 2235.

In the example embodiment of FIG. 12B, the imaging device 2235 is configured to obtain the 2-D images from two or more directions with respect to the subject. The direction and location of the imaging device 2235 with respect to the subject, and/or with respect to a fixed frame of reference, are optionally recorded, to aid in producing a vessel tree model, whether 1 dimensional (1-D) or three dimensional (3-D), from 2-D Images taken by the imaging device 2235.

The computer 2210 is optionally configured to: accept data from the plurality of imaging device 2235; produce a tree model of the patient's vascular system, wherein the tree model comprises geometric measurements of the patient's vascular system at one or more locations along a vessel centerline of at least one branch of the patient's vascular system, using at least some of the plurality of captured 2-D images; and produce a model of flow characteristics of the tree model.

In some embodiments a synchronization unit (not shown) is used to provide the imaging device 2235 with a synchronization signal for synchronizing the capturing of 2-D images of the patient's vascular system, optionally at a same phase during the cardiac cycle.

In some embodiments the computer 2210 accepts a subject's ECG signal (not shown), and selects 2-D images from the imaging device 2235 according to the ECG signal, for example in order to select 2-D images at a same cardiac phase.

In some embodiments, the system of FIG. 12A or 12B includes an image registration unit which detects corresponding image features in the 2-D images; calculates image correction parameters based on the corresponding image features; and registers the 2-D images so the image features correspond geometrically.

In some embodiments the image features are optionally selected as an origin of the tree model; and/or a location of minimal radius in a stenosed vessel; and/or a bifurcation of a vessel.

Exemplary System for Vascular State Scoring

Figure 22:
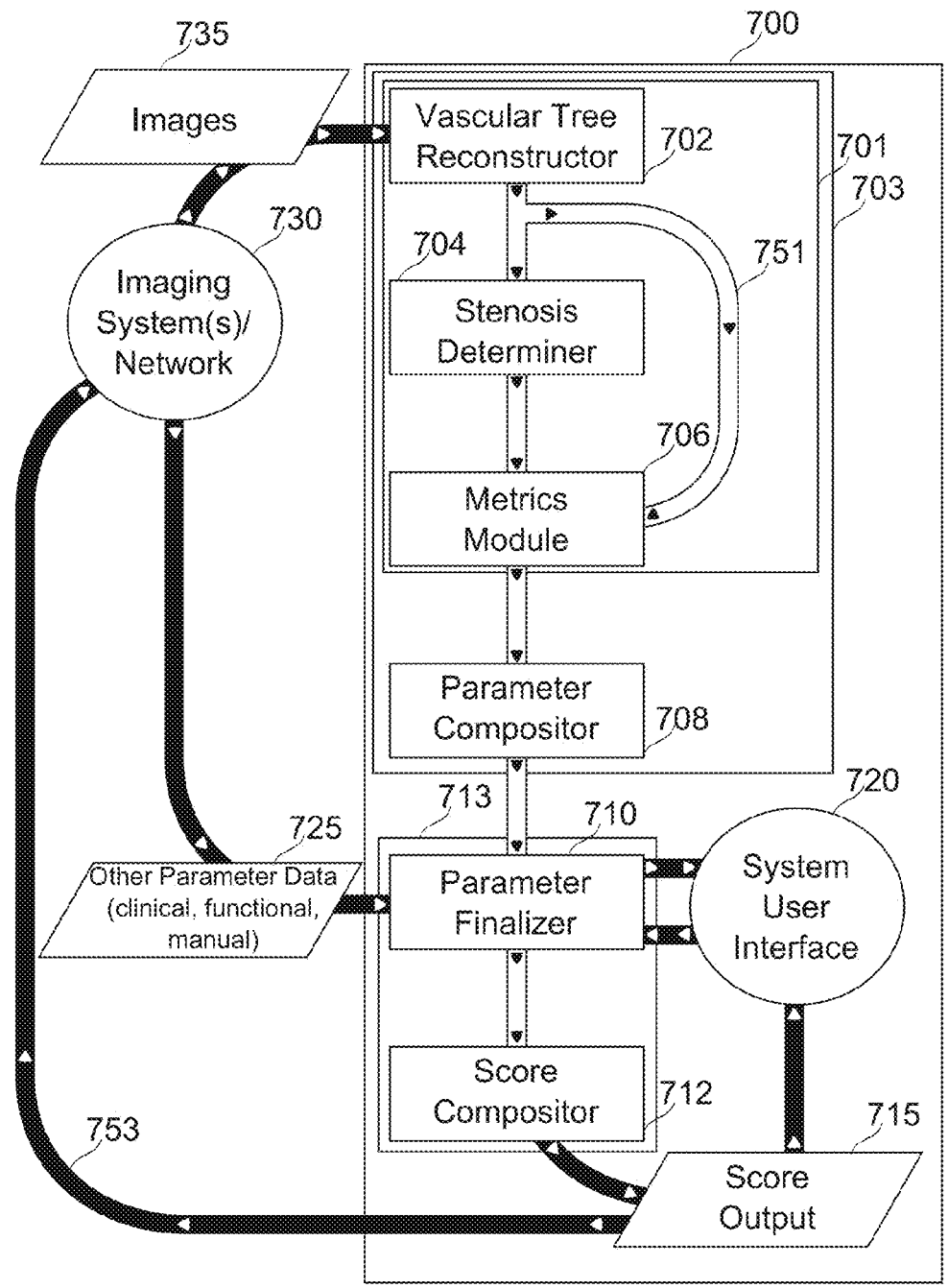
FIG. 22 is a simplified schematic of an automatic VSST scoring system, according to some exemplary embodiments of the invention.

Reference is now made to FIG. 22, which is a simplified schematic of an automatic VSST scoring system 700, according to some exemplary embodiments of the invention.

In FIG. 22, broad white pathways (for example, pathway 751) denote simplified paths of data processing through the system. Broad black pathways (for example, pathway 753) denote external data connections or connections to the system user interface 720. Black pathway data content is labeled by overlying trapezoidal blocks.

The vascular tree reconstructor 702, in some embodiments of the invention, receives image data 735 from one or more imaging systems or a system-connected network 730. Stenosis determiner 704, in some embodiments, determines the presence of stenotic vascular lesions based on the reconstructed vascular tree. In some embodiments, metrics module 706 determines additional metrics related to the disease state of the vascular tree, based on the reconstructed vascular tree and/or determined stenosis locations and other measurements.

In some embodiments, metrics extractor 701 comprises functions of vascular tree reconstructor 702, stenosis determiner 704, and/or metrics module 706. In some embodiments, metrics extractor 701 is operable to receive image data 735, and extract from it a plurality of vascular state metrics, suitable, for example, as input to parameter compositor 708.

In some embodiments, parameter compositor 708 converts determined metrics into subscore values (for example true/false values) which comprise parameters that "answer" vascular state scoring questions, and/or are otherwise are mapped to particular operations of a VSST scoring procedure.

In some embodiments, subscore extractor 703 comprises functions of vascular tree reconstructor 702, stenosis determiner 704, metrics module 706, and/or parameter compositor 708. In some embodiments, subscore extractor 703 comprises functions of metrics extractor 701. In some embodiments, subscore extractor 703 is operable to receive image data 735, and extract from it one or more VSST subscores, suitable as input for score calculator 713.

Parameter finalizer 710, in some embodiments, ensures that parameter data provided is sufficiently complete and correct to proceed to final scoring. In some embodiments, corrections to automatically determined parameters are determined at finalizer 710, optionally under operator supervision through system user interface 720. In some embodiments, lacunae in automatically provided parameter data are filled: for example, by user input from system user interface 720; or by other parameter data 725 provided, for example, from another diagnostic system or a network providing access to clinical data.

Score compositor 712, in some embodiments, composes the finalized outputs into a weighted score output 715 based on the determined parameters for the score. The score is made available, for example, over the system user interface or to networked resources 730.

In some embodiments of the invention, score calculator 713 comprises functions of the parameter finalizer 710 and/or score compositor 712. In some embodiments, score calculator 713 is operable to receive composited parameters and/or subscores (for example from parameter compositor 708 and/or subscore extractor 703), and convert them to a VSST score output 715.

In some embodiments of the invention, intermediate results of processing (for example, the reconstructed vascular tree, various metrics determined from it, and/or parameter determinations) are stored in permanent or temporary storage on storage devices (not shown) of the system 700, and/or on a network 730.

The scoring system 700 has been described in the context of modules which, in some embodiments of the invention, are implemented as programmed capabilities of a digital computer. It should be understood that the underlying system architecture may be implemented in various ways comprising embodiments of the invention; for example, as a single or multiple-process application and/or as client-server processes running on the same or on different computer hardware systems. In some embodiments of the invention, the system is implemented in code for execution by a general purpose processor. In some embodiments, part or all of the functionality of one or more modules provided by an FPGA or another dedicated hardware component such as an ASIC.

To provide one example of a client-server configuration, a subscore extractor 703 is implemented as a server process (or group of server-implemented processes) on one or more machines remote to a client computer which implements modules such as the score calculator 713 and user interface 720. It should be understood that other divisions of modules described herein (or even divisions within modules) are encompassed by some embodiments of the invention. A potential advantage of such a division may be, for example, to allow high-speed dedicated hardware to perform computationally intensive portions of the scoring, while providing an economy of scale by allowing the hardware to be shared by multiple end-users. Such a distributed architecture potentially also provides advantages for maintenance and/or distribution of new software versions.

Potential benefits of embodiments of the invention

Some example embodiments of the invention are minimally invasive, that is, they allow refraining from guidewire interrogation of the coronary artery, and therefore minimize danger to a patient, compared to an invasive FFR catheter procedure.

It is noted that an example embodiment of the invention enables measuring a reliable index during catheterization, providing a cost-effective way to potentially eliminate a need for processing angiographic data after the catheterization procedure, and/or for additional equipment during the catheterization procedure, such as a guidewire, and/or for materials involved in a catheterization procedure, such as adenosine. It is noted that another potential saving includes a saving in hospitalization costs following better treatment decisions.

An example embodiment of the invention optionally enables trying out various post-inflation vessel cross sections in various post-inflation models of the vascular system, and selecting a suitable stent for a subject based on desired flow characteristics of the post-inflation model.

An example embodiment of the invention optionally automatically identifies geometrical characteristics of a vessel, defines an outer contour of the vessel, and optionally provides relevant hemodynamic information associated with the vessel, corresponding to the present-day invasive FFR method.

An embodiment of the invention optionally generates an index indicative of a need for coronary revascularization. The minimally invasive embodiment of the invention potentially prevents unnecessary risk to patients, potentially reduces total time and cost of an angiography, hospitalization and follow-up.

A system constructed according to an example embodiment of the invention potentially enables shortening the diagnostic angiography procedure. Unnecessary coronary interventions during angiography and/or in the future are also potentially prevented. Also, a method according to an example embodiment of the invention optionally enables assessment of vascular problems in other arterial territories, such as carotid arteries, renal arteries, and diseased vessels of the limbs.

It is noted that resolution of angiographic images is typically higher than resolution typically obtained by 3-D techniques such a CT. A model constructed from the higher resolution angiographic images can be inherently higher resolution, and provide greater geometric accuracy, and/or use of geometric properties of smaller vessels than CT images, and/or calculations using branching vessels distal to a stenosis for more generations, or bifurcations, downstream from the stenosis than CT images.

A short list of potential non-invasive FFR benefits, one or more of which are provided in some embodiments of the present invention, includes:

a non-invasive method which does not endanger the patient;

a computational method without additional time or invasive equipment;

a prognostic benefit in 'borderline' lesions and in multi-vessel disease;

provides a reliable index to assess the need for coronary revascularization;

a method to assess and/or optimize revascularization procedures;

a strategy which saves cost of catheterization, hospitalization and follow-up;

preventing unnecessary coronary interventions following angiography; and a 'one-stop shop' comprehensive lesion assessment.

Another benefit of some present embodiments is the ability to produce a tree model within a short period of time. This allows calculating of indices, particularly but not necessarily, indices that are indicative of vascular function (e.g., FFR) also within a short period of time (e.g., within less than 60 minutes or less than 50 minutes or less than 40 minutes or less than 30 minutes or less than 20 minutes from the time at which the 2-D images are received by the computer). Preferably, the index is calculated while the subject is still immobilized on the treatment surface for the porpoise of catheterization. Such fast calculation of index is advantageous since it allows the physician to get the assessment for a lesion being diagnosed during the catheterization procedure, and thus enable quick decision regarding the proper treatment for that lesion. The physician can determine the necessity of treatment while being in the catheterization room, and does not have to wait for an offline analysis.

Additional advantages of fast calculation of index include reduced risk to the patient, ability to calculate the index without the need of drugs or invasive equipment, shortening of the duration of coronary diagnostic procedure, established prognostic benefit in borderline lesions, reduced costs, reduced number of unnecessary coronary interventions and reduced amount of subsequent procedures.

In this "game" of assessing the hemodynamic severity of each lesion, a non-real-time solution is often not a considered option. The physician needs to know whether to treat the lesion in the cath lab or not, and can't afford to wait for an offline analysis. CT-based solutions are also part of a different "game", since the utilization of cardiac CT scans is low compared to PCI procedures, and the resolution, both temporal and spatial, is much lower compared to angiograms.

Another point to stress, is that the on-line image-based FFR evaluation, unlike the invasive evaluation, potentially allows assessment of borderline lesions, and won't be necessarily limited to the percentage of lesions evaluated nowadays, since the risk to the patient (for example, due to guidewire traversal), and the cost will be a lot lower.

It is expected that during the life of a patent maturing from this application many relevant methods and systems for imaging a vascular system will be developed and the scope of the terms describing imaging are intended to include all such new technologies a priori.

As used herein the term "about" refers to 10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Throughout this application, various embodiments of this invention may be presented in a range format. It should be understood that the description in range format merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for construction of a vascular tree model comprising:
receiving by image processing circuitry a plurality of 2-D angiographic images showing blood vessel segments of a portion of a vasculature of a subject;
extracting automatically by the image processing circuitry, from each of said plurality of 2-D angiographic images, an image feature set comprising 2-D feature positions of said blood vessel segments; and
identifying homologous vascular branches among the 2-D angiographic images using said blood vessel segments, wherein the identifying comprises:
adjusting automatically by the image processing circuitry said 2-D feature positions to reduce relative position error in a common 3-D coordinate system to which each said image feature set is back-projectable, and
then associating automatically by the image processing circuitry image features of the image feature sets as representing homologous vascular branches, based on their projection from the planes of the 2-D angiographic images to common blood vessel segment regions in said common 3-D coordinate system.

2. The method of claim 1, wherein the image feature set which is extracted comprises a centerline data set including 2-D centerline positions ordered along said blood vessel segments.

3. The method of claim 2, wherein said adjusting and associating are performed with elements of said centerline data set.

4. The method of claim 2, wherein said adjusting comprises registration of said 2-D images in 3-D space according to parameters which bring said 2-D centerline positions into closer correspondence among their 3-D back-projections.

5. The method of claim 2, comprising estimating a metric of radial vascular width based on values of at least one of said plurality of 2-D angiographic images along lines perpendicular to said ordered 2-D centerline positions.

6. The method of claim 2, wherein said adjusting comprises adjusting of said 2-D feature positions based on projection of said common 3-D coordinate system into the 2-D plane of at least one of said plurality of 2-D angiographic images.

7. The method of claim 1, wherein information required for said associating automatically of image features is entirely provided before review of said images by a human operator.

8. The method of claim 1, further comprising defining a surface corresponding to a shape of the heart of the subject, and using said surface as a constraint for said associating of said image features.

9. The method of claim 1, wherein said images are acquired upon injection of a contrast agent to said vasculature, and further comprising:
determining temporal characteristics of the movement of said contrast agent through said vasculature; and
constraining said 2-D feature positions based on said temporal characteristics.

10. The method of claim 1, wherein said portion of said vasculature comprises coronary arteries.

11. The method of claim 1, further comprising:
inspecting projections from the blood vessel segment regions associated with the image features to the planes of 2-D angiographic images to identify image portions representing blood vessel segment regions for which a physical characteristic is to be calculated;
selecting automatically by image processing circuitry a portion of at least one of said plurality of 2-D angiographic images, the portion comprising a representation of said associated image features identified by the inspecting; and
calculating a physical characteristic of at least one of the blood vessel segments, based on the selected image portion.

12. A computer software product, comprising a computer-readable storage medium in which program instructions are stored, which instructions, when read by a computer, cause the computer to receive a plurality of 2-D angiographic images of a portion of a vasculature and execute the method according to claim 1.

13. A method for construction of a vascular tree model comprising:
receiving by image processing circuitry a plurality of 2-D angiographic images showing blood vessel segments of a portion of a vasculature of a subject;
extracting automatically by the image processing circuitry, from each of said plurality of 2-D angiographic images, an image feature set comprising 2-D feature positions of said blood vessel segments;
adjusting automatically by the image processing circuitry said 2-D feature positions to reduce relative position error in a common 3-D coordinate system to which each said image feature set is back-projectable;
wherein the adjusting comprises iteratively determining a consensus centerline in the common 3-D coordinate system for the feature sets from the plurality of 2-D angiographic images, and wherein the relative position error is calculated based on differences in positions of the projection of the consensus centerline to coordinate systems of the plurality of 2-D angiographic images from positions of the respective image feature sets of the plurality of 2-D angiographic images; and
associating automatically by the image processing circuitry image features of the image feature sets to one another based on their projection from the planes of the 2-D angiographic images to common blood vessel segment regions in said common 3-D coordinate system.

14. The method of claim 13, wherein the image feature set comprises a centerline data set including 2-D centerline positions ordered along said blood vessel segments.

15. The method of claim 14, wherein said adjusting and associating are performed with elements of said centerline data set.

16. The method of claim 14, wherein said adjusting comprises registration of said 2-D images in 3-D space according to parameters which bring said 2-D centerline positions into closer correspondence among their 3-D back-projections.

17. The method of claim 14, comprising estimating a metric of radial vascular width based on values of at least one of said plurality of 2-D angiographic images along lines perpendicular to said ordered 2-D centerline positions.

18. The method of claim 14, wherein said adjusting comprises adjusting of said 2-D feature positions based on projection of said common 3-D coordinate system into the 2-D plane of at least one of said plurality of 2-D angiographic images.

19. The method of claim 13, wherein information for said associating automatically of image features is provided before review of said 2-D angiographic images by a human operator.

20. The method of claim 13, further comprising defining a surface corresponding to a shape of the heart of the subject, and using said surface as a constraint for said associating of said image features.

21. The method of claim 13, wherein said images are acquired upon injection of a contrast agent to said vasculature, and further comprising:
  determining temporal characteristics of the movement of said contrast agent through said vasculature; and
  constraining said 2-D feature positions based on said temporal characteristics.

22. The method of claim 13, wherein said portion of said vasculature comprises coronary arteries.

23. The method of claim 13, further comprising:
  inspecting projections from the blood vessel segment regions associated with the image features to the planes of 2-D angiographic images to identify image portions representing blood vessel segment regions for which a physical characteristic is to be calculated;
  selecting automatically by image processing circuitry a portion of at least one of said plurality of 2-D angiographic images, the portion comprising a representation of said associated image features identified by the inspecting; and
  calculating a physical characteristic of at least one of the blood vessel segments, based on the selected image portion.

* * * * *